United States Patent [19]

Chakravarty et al.

[11] Patent Number: 5,391,566
[45] Date of Patent: Feb. 21, 1995

[54] BENZIMIDAZOLINONES SUBSTITUTED WITH PHENOXYPHENYLACETIC ACID DERIVATIVES

[75] Inventors: Prasun K. Chakravarty, Edison; Elizabeth M. Naylor, Scotch Plains; James R. Tata; Thomas F. Walsh, both of Westfield, all of N.J.

[73] Assignee: Merck & Co., Inc., Rahway, N.J.

[21] Appl. No.: 94,592

[22] Filed: Jul. 20, 1993

[51] Int. Cl.⁶ .................. A61K 31/415; C07D 235/26
[52] U.S. Cl. ........................... 514/387; 548/306.4; 548/305.1
[58] Field of Search .................. 548/305.1, 306.4; 514/387

[56] References Cited

U.S. PATENT DOCUMENTS

| | | | |
|---|---|---|---|
| 4,612,323 | 9/1986 | Kisida et al. | 514/394 |
| 5,082,838 | 1/1992 | Naka et al. | 514/211 |
| 5,114,918 | 5/1992 | Ishikawa et al. | 514/11 |
| 5,187,159 | 2/1993 | Greenlee et al. | 514/81 |
| 5,187,195 | 2/1993 | Oohata et al. | 514/510 |

FOREIGN PATENT DOCUMENTS

| | | |
|---|---|---|
| 0459136 | 12/1991 | European Pat. Off. . |
| 0510526A1 | 10/1992 | European Pat. Off. . |
| 0558258A1 | 9/1993 | European Pat. Off. . |
| 4364171 | 12/1992 | Japan . |
| 2259540A | of 1993 | United Kingdom . |
| WO92/15321 | 9/1992 | WIPO . |

OTHER PUBLICATIONS

Naka et al., Chemical Abstracts vol. 116 No. 13, Abstract No. 128924 (1992).

*Primary Examiner*—Mary C. Lee
*Assistant Examiner*—Jacqueline Haley
*Attorney, Agent, or Firm*—Valerie J. Camara; Mark R. Daniel; Joseph F. DiPrima

[57] ABSTRACT

Phenoxyphenylacetic acids and derivatives of the general structural formula I

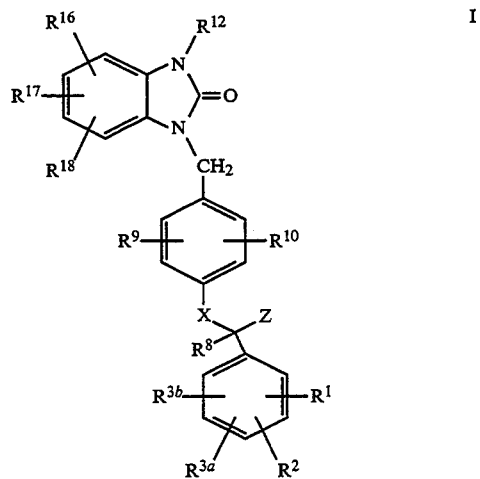

have endothelin antagonist activity and are therefore useful in treating cardiovascular disorders, such as hypertension, pulmonary hypertension, postischemic renal failure, vasospasm, cerebral and cardiac ischemia, myocardial infarction, endotoxic shock, inflammatory diseases including Raynaud's disease and asthma.

17 Claims, No Drawings

BENZIMIDAZOLINONES SUBSTITUTED WITH PHENOXYPHENYLACETIC ACID DERIVATIVES

SUMMARY OF THE INVENTION

This invention is concerned with non-peptidic endothelin receptor antagonists and their method of use. The compounds of the present invention are therapeutic agents particularly useful for the treatment of asthma, hypertension, pulmonary hypertension, arteriosclerosis, congestive heart failure, renal failure, particularly post-ischemic renal failure, cyclosporin nephrotoxicity, vasospasm, vascular restenosis, cerebral and cardiac ischemia and other ischemic states, myocardial infarction, Raynaud's disease, the vascular consequences of diabetes such as glaucoma and neuropathy, inflammatory bowel diseases, including Crohn's disease and ulcerative colitis, as well as other inflammatory diseases, or endotoxic shock caused by or associated with endothelin.

BACKGROUND OF THE INVENTION

Endothelin is a 21-amino acid peptide produced by endothelial cells. The peptide is secreted not only by endothelial cells but also by tracheal epithelial cells or from kidney cells. Endothelin (ET-1) has a potent vasoconstrictor effect. The vasoconstricting effect is caused by the binding of endothelin to its receptor on the vascular smooth muscle cells.[1-3]

Endothelin-1 (ET-1) is one of three recently identified potent vasoconstricting peptides which also includes endothelin-2 (ET-2) and endothelin-3 (ET-3) which differ from ET-1 by two and six amino acids, respectively.[4]

Increased levels of endothelin are found in the blood of patients with essential hypertension, acute myocardial infarction, pulmonary hypertension, Raynaud's disease or atherosclerosis or in the washing fluids of the respiratory tract of patients with asthma compared to normal levels.[5-8]

An experimental model of cerebral vasospasm and a second model of acute renal failure have led to the conclusion that endothelin is one of the mediators causing cerebral vasospasm following a subarachnoid hemorrhage, and renal failure.[9-10]

Endothelin was also found to control the release of many physiological substances such as renin, atrial natriuretic peptide, endothelium-derived relaxing factor (EDRF), thromboxane $A_2$,[14] prostacyclin, norepinephrine, angiotensin II and substance P.[11-16] Further, endothelin causes contraction of the smooth muscle of the gastrointestinal tract and the uterine smooth muscle.[1-7-19] Endothelin has also been shown to promote the growth of rat vascular smooth muscle cells which would suggest a possible relevance to arterial hypertrophy.[20]

Endothelin receptors are present in high concentration in the peripheral tissues and also in the central nervous system, and cerebral administration of endothelin has been shown to induce behavioral changes in animals, suggesting that endothelin may play an important role in controlling neural functions.[21]

Endotoxin has been shown to promote the release of endothelin. This finding has suggested that endothelin is an important mediator for endotoxin-induced diseases.[22-23]

A study has shown that when cyclosporin is added to a renal cell culture, endothelin secretion is increased.[24] Another study has shown that administration of cyclosporin to rats, led to a decrease in the glomerular filtration rate and an increase in the blood pressure, in association with a remarkable increase in the circulating endothelin level. This cyclosporin-induced renal failure can be suppressed by the administration of anti-endothelin antibody.[25] These studies suggest that endothelin is significantly involved in the pathogenesis of cyclosporin-induced renal disease.

A recent study in patients with congestive heart failure demonstrated a good correlation between the elevated levels of endothelin in the plasma and the severity of the disease.[26]

Substances which specifically inhibit the binding of endothelin to its receptor are believed to block the physiological effects of endothelin and would be useful in treating patients with endothelin related disorders. The present invention discloses potent non-peptidic endothelin antagonists.

Endothelin is an endogenous substance which directly or indirectly (through the controlled release of various other endogenous substances) induces sustained contraction of vascular or non-vascular smooth muscles. Its excess production or excess secretion is believed to be one of the factors responsible for hypertension, pulmonary hypertension, Raynaud's disease, bronchial asthma, acute renal failure, myocardial infarction, angina pectoris, arteriosclerosis, cerebral vasospasm and cerebral infarction.

The novel compounds of the present invention are useful as non-peptidic endothelin antagonists, and have not been disclosed in any issued patents or patent applications. Fujisawa in European Patent Application EP 457,195, Banyu in EP 436,189 and 460,679, and Takeda in Patent Cooperation Treaty International Publication No. WO 91/13089 and EP 528,312 have applications disclosing linear and cyclic peptidic compounds as endothelin antagonists. Fujisawa has also disclosed anthraquinone derivatives produced by a fermentation process using *Streptomyces* sp. No. 89009 in EP 405,421.

A Roussel-Uclaf European Patent Application (EP 498,723) disclosed a series of substituted (1,4-quinolinoxy)methylbiphenylcarboxylic acids as both endothelin antagonists and angiotensin II antagonists. Two patent applications from Hoffmann-La Roche, EP 510,526 and EP 526,708 and EP 526,708, published Oct. 28, 1992 and Feb. 10, 1993, respectively, have also appeared claiming N-(4-pyrimidinyl)benzenesulfonamides compounds with endothelin antagonist properties. A patent application from Shionogi, EP 526,642, discloses a series of triterpene derivatives with endothelin antagonist properties.

REFERENCES

1 Nature, 332, 411–415 (1988).

2 FEBS Letters, 23 1,440–444 (1988).

3 Biochem. Biophys. Res. Commun. 154, 868–875 (1988).

4 TIPS, 13, 103–108, March 1992.

5 Japan J. Hypertension 12, 79 (1989).

6 J. Vascular Medicine Biology, 2, 207 (1990).

7 J. Am. Med. Association, 264, 2868 (1990).

8 The Lancet, ii, 207 (1990) and The Lancet, ii, 747–748 (1989).

9 Japan. Soc. Cereb. Blood Flow & Metabol. 1, 73 (1989).

10 J. Clin. Invest., 83, 1762–1767 (1989).

11 Biochem. Biophys. Res. Comm. 157, 1164–1168 (1988).

12 Biochem. Biophys. Res. Comm. 155, 167–172 (1989).
13 Proc. Natl. Acad. Sci. USA, 85, 9797–9800 (1989).
14 J. Cardiovasc. Pharmacol., 13,589–592 (1989).
15 Japan. J. Hypertension 12, 76 (1989).
16 Neuroscience Letters, 102, 179–184 (1989).
17 FEBS Letters, 247, 337–340 (1989).
18 Eur. J. Pharmacol. 154, 227–228 (1988).
19 Biochem. Biophys. Res. Commun., 159, 317–323 (1989).
20 Atherosclerosis, 78, 225–228 (1989).
21 Neuroscience Letters, 97, 276–279 (1989).
22 Biochem. Biophys. Res. Commun. 161, 1220–1227 (1989).
23 Acta. Physiol. Scand., 137, 317–318 (1989).
24 Eur. J. Pharmacol., 180, 191–192 (1990).
25 Kidney Int. 37, 1487–1491 (1990).
26 Mayo Clinic Proc., 67, 719–724 (1992).

DETAILED DESCRIPTION OF THE INVENTION.

This invention is concerned with novel compounds of structural formula I:

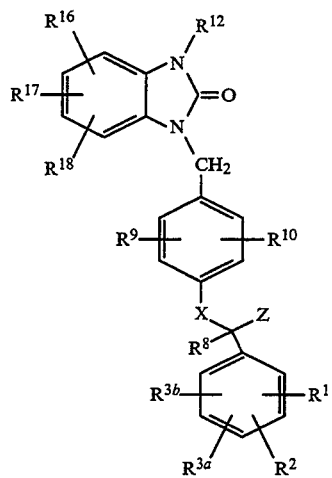

or a pharmaceutically acceptable salt thereof, wherein:
$R^1$, $R^2$, $R^{3a}$ and $R^{3b}$ are independently:
  (a) H,
  (b) F, Cl, Br, or I,
  (c) —$NO_2$,
  (d) —$NH_2$,
  (e) —NH($C_1$-$C_4$)-alkyl,
  (f) —N[($C_1$-$C_4$)-alkyl]$_2$,
  (g) —$SO_2NHR^7$,
  (h) —$CF_3$,
  (i) ($C_1$-$C_4$)-alkyl,
  (j) —$OR^7$,
  (k) —S(O)$_n$—($C_1$-$C_4$)-alkyl,
  (l) —NHCO—($C_1$-$C_4$)-alkyl,
  (m) —NHCO—O($C_1$-$C_4$)-alkyl,
  (n) —$CH_2$O—($C_1$-$C_4$)-alkyl,
  (o) —O—($CH_2$)$_m$—$OR^7$,
  (p) —$CONR^7R^{11}$, or
  (q) —$COOR^7$;
n is 0, 1 or 2;
m is 2, 3 or 4;
$R^1$ and $R^2$ on adjacent carbon atoms can be joined together to form a ring structure:

A represents:
  a) —y—C($R^4$)=C($R^5$)—,
  b) —Y—C($R^4$)=N—,
  c) —Y—N=C($R^4$)—,
  d) —Y—[C($R^6$)($R^6$)]$_s$—Y—,
  e) —y—C($R^6$)($R^6$)—C($R^6$)($R^6$)—,
  f) —C($R^4$)=C($R^5$)—Y—,
  g) —N=C($R^4$)—Y—,
  h) —C($R^6$)($R^6$)—C($R^6$)($R^6$)—Y—, or
  i) —C($R^4$)=C($R^5$)—C($R^4$)=C($R^5$)—;
s is 1 or 2;
Y is —O—, —S(O)n— and $NR^7$;
$R^4$ and $R^5$ are independently:
  (a) H,
  (b) ($C_1$-$C_6$)-alkyl or ($C_2$-$C_6$)-alkenyl each of which is unsubstituted or substituted with one or two substituents selected from the group consisting of:
    (i) —OH,
    (ii) —O—($C_1$-$C_4$)-alkyl,
    (iii) —S(O)n—($C_1$-$C_4$)-alkyl,
      —$NR^7$—($C_1$-$C_4$)-alkyl,
    (iv) —$NR^4$—($C_1$-$C_4$)-alkyl,
    (v) —$NHR^7$,
    (vi) —$COOR^7$,
    (vii) —$CONHR^7$,
    (viii) —$OCOR^{11}$, or
    (ix) —$CONR^7R^{11}$,
  (c) ($C_3$-$C_7$)-cycloalkyl,
  (d) F, Cl, Br, I,
  (e) $CF_3$,
  (f) —$COOR^7$,
  (g) —$CONR^7R^{11}$,
  (h) —$NR^7R^{11}$,
  (i) —$NR^7CONR^7R^{11}$,
  (j) —$NR^7COOR^{11}$,
  (k) —$SO_2NR^7R^{11}$,
  (l) —O—($C_1$-$C_4$)-alkyl,
  (m) —S(O)$_n$—($C_1$-$C_4$)-alkyl, or
  (n) —$NHSO_2R^{11}$;
$R^6$ is:
  (a) H,
  (b) ($C_1$-$C_4$)-alkyl unsubstituted or substituted with one of the following substituents:
    (i) —OH,
    (ii) —$NR^7R^{11}$,
    (iii) —$COOR^7$,
    (iv) —$CONHR^7$, or
    (v) —$CONR^7R^{11}$, or
  (c) F;
$R^7$ is:
  (a) H,
  (b) ($C_1$-$C_6$)-alkyl,
  (c) phenyl,
  (d) benzyl, or
  (e) ($C_3$-$C_7$)-cycloalkyl;
$R^8$ is:
  (a) H,
  (b) ($C_1$-$C_6$)-alkyl, unsubstituted or substituted with a substituent selected from the group consisting of:

(i) —phenyl,
(ii) —($C_3$–$C_7$)-cycloalkyl,
(iii) —$NR^7R^{11}$,
(iv) —morpholin-4-yl,
(v) —OH,
(vi) —$CO_2R^7$, or
(vii) —$CON(R^7)_2$,
(c) phenyl, unsubstituted or substituted with a substituent selected from the group consisting of:
(i) ($C_1$–$C_4$)-alkyl
(ii) —O—($C_1$–$C_4$)-alkyl
(iii) —$CONR^7R^{11}$,
(iv) F, Cl, Br or I, or
(v) —$COOR^7$;

$R^9$ and $R^{10}$ are independently:
(a) H,
(b) ($C_1$–$C_6$)-alkyl, unsubstituted or substituted with ($C_3$–$C_7$)-cycloalkyl,
(c) ($C_2$–$C_6$)-alkenyl,
(d) ($C_2$–$C_6$)-alkynyl,
(e) Cl, Br, F, I,
(f) ($C_1$–$C_6$)-alkoxy,
(g) when $R^9$ and $R^{10}$ are on adjacent carbons, they can be joined to form a phenyl ring,
(h) perfluoro-($C_1$–$C_6$)-alkyl,
(i) ($C_3$–$C_7$)-cycloalkyl, unsubstituted or substituted with ($C_1$–$C_6$)-alkyl,
(j) phenyl,
(k) ($C_1$–$C_6$)-alkyl—$S(O)_n$—$(CH_2)_n$—,
(l) hydroxy-($C_1$–$C_6$)-alkyl,
(m) —$CF_3$,
(n) —$CO_2R^7$,
(o) —OH,
(p) —$NR^7R^{11}$,
(q) —[($C_1$–$C_6$)-alkyl]$NR^7R^{11}$,
(r) —$NO_2$,
(s) —$(CH_2)_n$—$SO_2$—$N(R^7)_2$,
(t) —$NR^7CO$—($C_1$–$C_4$)-alkyl, or
(u) —$CON(R^7)_2$;

$R^{11}$ is
(a) ($C_1$–$C_6$)-alkyl,
(b) phenyl,
(c) —($C_1$–$C_4$)-alkyl-phenyl, or
(d) ($C_3$–$C_7$)-cycloalkyl;

$R^{12}$ is
(a) H,
(b) ($C_1$–$C_6$)-alkyl, unsubstituted or substituted with one or two substituents selected from the group consisting of:
i) —OH,
ii) —O—($C_1$–$C_4$)-alkyl,
iii) —O—($C_1$–$C_4$)-cycloalkyl,
iv) —$S(O)_n$—($C_1$–$C_4$)-alkyl,
v) —$NR^7$—($C_1$–$C_4$)-alkyl,
vi) —$NR^7R^{11}$,
vii) —$COOR^7$,
viii) —$CONHR^7$,
ix) —$OCOR^{11}$,
x) —$CONR^7R^{11}$,
xi) —$NR^7CONR^7R^{11}$,
xii) —$NR^7COOR^{11}$,
xiii) —$C(R^6)(OH)$—$C(R^6)(R^7)(OH)$, or
xiv) —$SO_2NR^7R^{11}$,
(c) ($C_3$–$C_7$)-cycloalkyl,
(d) ($C_1$–$C_4$)-perfluoroalkyl,
(e) aryl, unsubstituted or substituted with one to three substituents selected from the group consisting of:
i) F, Cl, Br, I,
ii) ($C_1$–$C_6$)-alkyl,
iii) ($C_1$–$C_6$)-alkoxy,
iv) hydroxy-($C_1$–$C_6$)-alkyl,
v) —$CF_3$,
vi) —$COOR^7$,
vii) —OH,
viii) —$NR^7R^{11}$,
ix) —$NH_2$,
x) —$NO_2$,
xi) —$CONR^7R^{11}$,
xii) two adjacent groups may be joined together to form a methylenedioxy group,
(f) aryl($C_1$–$C_2$)alkyl unsubstituted or substituted with one to three substituents selected from the group consisting of:
i) F, Cl, Br, I,
ii) ($C_1$–$C_6$)-alkyl,
iii) ($C_1$–$C_6$)-alkoxy,
iv) hydroxy-($C_1$–$C_6$)-alkyl,
v) —$CF_3$,
vi) —$COOR^7m$,
vii) —OH,
viii) —$NR^7R^{11}$,
ix) —$NH_2$,
x) —$NO_2$,
xi) —$CONR^7R^{11}$,
xii) two adjacent groups may be joined together to form a methylenedioxy group,
(g) heteroaryl, wherein heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl or carbazolyl and is unsubstituted or substituted with one or two substituents selected from the group consisting of:
i) F, Cl, Br, I,
ii) ($C_1$–$C_6$)-alkyl,
iii) ($C_1$–$C_6$)-alkoxy,
iv) —$CF_3$,
v) —$COOR^7$,
vi) —$NR^7R^{11}$,
vii) —$NH_2$,
viii) —$NO_2$,
ix) —$CONR^7R^{11}$;

X is
(a) —O—,
(b) —$S(O)n$—,
(c) —$NR^7$—,
(d) —$CH_2O$—,
(e) —$CH_2S(O)n$—,
(f) —$CH_2NR^7$—,
(g) —$OCH_2$—,
(h) —$N(R^7)CH_2$—,
(i) —$S(O)_nCH_2$—,
(j) —single bond, or
(k) —$C(R^9)_2$—, Z is:
(a) —$CO_2H$,
(b) —$CO_2R^{13}$,
(c) —CONH—(tetrazol-5-yl),
(d) —$CONHSO_2$-phenyl, wherein phenyl is unsubstituted or substituted with one or two substituents selected from the group consisting of:
i) ($C_1$–$C_4$)-alkyl,
ii) —O—($C_1$–$C_4$)-alkyl,
iii) —$CONR^7R^{11}$,
iv) F, Cl, Br or I, (v) —COOR⁷,
vi) ($C_1$-$C_4$)-perfluoroalkyl,
vii) ($C_3$-$C_7$)-cycloalkyl,
(viii) $NR^7R^{11}$,
(ix) $SO_2NR^7R^{11}$,
x) hydroxy, or
xi) 2,3-, or 3,4-methylenedioxy;
(e) —CONHSO₂-($C_1$-$C_8$)-alkyl, wherein the alkyl group is unsubstituted or substituted as defined in $R^4$(b),
(f) —CONHSO₂-($C_1$-$C_4$)-perfluoroalkyl,
(g) —CONHSO₂-($C_3$-$C_7$)-cycloalkyl,
(h) —tetrazol-5-yl,
(i) —CONHSO₂-heteroaryl, wherein heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl or carbazolyl,
(j) —SO₂NHCO-phenyl, wherein phenyl is as defined in Z(d) above,
(k) —SO₂NHCO-($C_1$-$C_8$)-alkyl, wherein the alkyl group is unsubstituted or substituted as defined in $R^4$(b),
(l) —SO₂NHCO-($C_1$-$C_4$)-perfluoroalkyl,
(m) —SO₂NHCO-heteroaryl, wherein heteroaryl is as defined in Z(h) above,
(n) —SO₂NHCON($R^{11}$)₂ wherein the $R^{11}$ groups are the same or different,
(o) —PO(OR⁷)₂, wherein the $R^7$ groups are the same or different, or
(p) —PO($R^{11}$)OR⁷;
$R^{13}$ is:
(a) ($C_1$-$C_4$)-alkyl,
(b) $CHR^{14}$—O—$COR^{15}$,
(c) $CH_2CH_2$—N[($C_1$-$C_2$)-alkyl]₂,
(d) $CH_2CH_2$—N[$CH_2CH_2$]₂O,
(e) ($CH_2CH_2O$)y—O—[($C_1$-$C_4$)-alkyl], wherein y is 1 or 2,
(f) phenyl, naphthyl, $CH_2$-phenyl or $CH_2$-naphthyl, where phenyl or naphthyl is substituted or unsubstituted with $CO_2$-($C_1$-$C_4$)-alkyl,

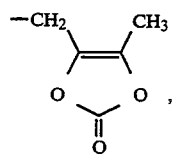  (g)

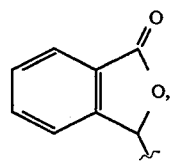  (h)

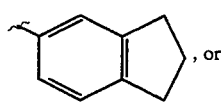  (i)

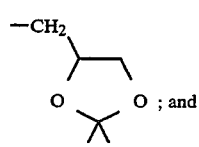  (j)

$R^{14}$ and $R^{15}$ independently are ($C_1$-$C_6$)-alkyl or phenyl,
$R^{16}$, $R^{17}$ and $R^{18}$ are independently:
(a) H,
(b) ($C_1$-$C_6$)-alkyl, unsubstituted or substituted with one or two substituents selected from the group consisting of:
i) —OH,
ii) —O—($C_1$-$C_4$)-alkyl,
iii) —$NR^7R^{11}$,
iv) —COOR⁷,
v) —$CONR^7R^{11}$,
vi) —$SO_2NR^7R^{11}$,
vii) —NH₂,
viii) —NO₂,
(c) ($C_3$-$C_7$)-cycloalkyl,
(d) ($C_1$-$C_4$)-perfluoroalkyl,
(e) F, Cl, Br, I,
(f) —OH,
(g) ($C_1$-$C_4$)-alkoxy,
(h) —COOR⁷,
(i) —$CONR^7R^{11}$,
(j) —CONHSO₂-($C_1$-$C_6$)-alkyl wherein the alkyl group is unsubstituted or substituted as defined in $R^4$(b),
(k) —CONHSO₂-phenyl wherein the phenyl group is unsubstituted or substituted as defined in Z(d),
(l) —$NR^7R^{11}$,
(m) —NH₂,
(n) —NO₂,
(o) —$NR^7COR^{11}$,
(p) —$NR^7COOR^{11}$,
(q) —$NR^7CONR^7R^{11}$,
(r) two adjacent groups may be joined together to form a methylenedioxy group,
(s) —$SO_2NR^7R^{11}$m
(t) —SO₂NHCO-($C_1$-$C_6$)-alkyl wherein the alkyl group is unsubstituted or substituted as defined in $R^4$(b),
(u) —SO₂NHCO-phenyl wherein the phenyl group is unsubstituted or substituted as defined in Z(d).

An embodiment of the invention are the compounds of structural formula II:

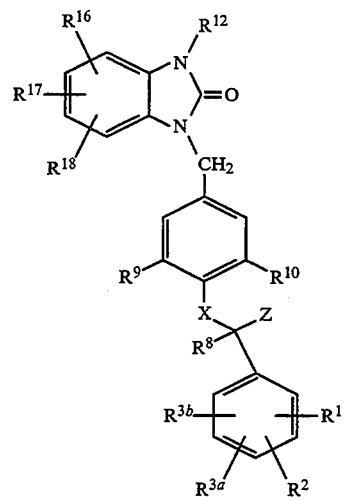

or a pharmaceutically acceptable salt thereof, wherein:
$R^1$, $R^2$, $R^{3a}$ and $R^{3b}$ are independently:
(a) H, (b) F, Cl, Br, or I,
(c) —$NO_2$,
(d) —$NH_2$,
(e) —$NH(C_1$-$C_4)$-alkyl,
(f) —$N[(C_1$-$C_4)$-alkyl$]_2$,
(g) —$SO_2NHR^7$,
(h) —$CF_3$,
(i) ($C_1$-$C_4$)-alkyl,
(j) —$OR^7$,
(k) —$S(O)n$-($C_1$-$C_4$)-alkyl,
(l) —$NHCO$-($C_1$-$C_4$)-alkyl,
(m) —$NHCO$-$O(C_1$-$C_4$)-alkyl,
(n) —$CH_2O$-($C_1$-$C_4$)-alkyl,
(o) —$O$—$(CH_2)_m$-$OR^7$,
(p) —$CONR^7R^{11}$, or
(q) —$COOR^7$;

m is 2, 3 or 4,
n is 0, 1 or 2,
$R^1$ and $R^2$ on adjacent carbon atoms can be joined together to form a ring structure:

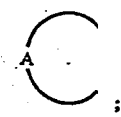

A represents:
a) —Y—$C(R^4)$=$C(R^5)$—,
b) —Y—$C(R^4)$=N—,
c) —Y—N=$C(R^4)$—,
d) —Y—$[C(R^6)(R^6)]_s$—Y—,
e) —Y—$C(R^6)(R^6)$-$C(R^6)(R^6)$—,
f) —$C(R^4)$=$C(R^5)$—Y—,
g) —N=$C(R^4)$—Y—,
h) —$C(R^6)(R^6)$-$C(R^6)(R^6)$—Y—, or
i) —$C(R^4)$=$C(R^5)$-$C(R^4)$=$C(R^5)$—;

s is 1 or 2;
Y is —O—, —$S(O)n$— and $NR^7$;
$R^4$ and $R^5$ are independently:
(a) H,
(b) ($C_1$-$C_6$)-alkyl or ($C_2$-$C_6$)-alkenyl each of which is unsubstituted or substituted with one or two substituents selected from the group consisting of:
  (i) —OH,
  (ii) —O—($C_1$-$C_4$)-alkyl,
  (iii) —$S(O)n$-($C_1$-$C_4$)-alkyl,
  (iv) —$NR^7$-($C_1$-$C_4$)-alkyl,
  (v) —$NHR^7$,
  (vi) —$COOR^7$,
  (vii) —$CONHR^7$,
  (viii) —$OCOR^{11}$, or
  (ix) —$CONR^7R^{11}$,
(c) ($C_3$-$C_7$)-cycloalkyl,
(d) F, Cl, Br, I,
(e) $CF_3$,
(f) —$COOR^7$,
(g) —$CONR^7R^{11}$,
(h) —$NR^7R^{11}$,
(i) —$NR^7CONR^7R^{11}$,
(j) —$NR^7COOR^{11}$,
(k) —$SO_2NR^7R^{11}$,
(l) —O—($C_1$-$C_4$)-alkyl,
(m) —$S(O)n$-($C_1$-$C_4$)-alkyl, or
(n) —$NHSO_2R^{11}$;

$R^6$ is:
(a) H,
(b) ($C_1$-$C_4$)-alkyl unsubstituted or substituted with one or two substituents selected from the group consisting of:
  (i) —OH,
  (ii) —$NR^7R^{11}$,
  (iii) —$COOR^7$,
  (iv) —$CONHR^7$, or
  (v) —$CONR^7R^{11}$, or
(c) F;

$R^7$ is:
(a) H,
(b) ($C_1$-$C_6$)-alkyl,
(c) phenyl,
(d) benzyl, or
(e) ($C_3$-$C_7$)-cycloalkyl;

$R^8$ is:
(a) H,
(b) ($C_1$-$C_6$)-alkyl, unsubstituted or substituted with one or two substituents selected from the group consisting of:
  (i) —phenyl,
  (ii) —($C_3$-$C_7$)-cycloalkyl,
  (iii) —$NR^7R^{11}$,
  (iv) —morpholin-4-yl,
  (v) —OH,
  (vi) —$CO_2R^7$, or
  (vii) —$CON(R^7)_2$, or
(c) phenyl;

$R^9$ and $R^{10}$ are independently:
(a) H,
(b) ($C_1$-$C_6$)-alkyl, unsubstituted or substituted with ($C_3$-$C_7$)-cycloalkyl,
(c) ($C_2$-$C_6$)-alkenyl,
(d) ($C_2$-$C_6$)-alkynyl,
(e) Cl, Br, F, I,
(f) ($C_1$-$C_6$)-alkoxy,
(g) when $R^9$ and $R^{10}$ are on adjacent carbons, they can be joined to form a phenyl ring,
(h) perfluoro-($C_1$-$C_6$)-alkyl,
(i) ($C_3$-$C_7$)-cycloalkyl, unsubstituted or substituted with ($C_1$-$C_6$)-alkyl,
(j) phenyl,
(k) ($C_1$-$C_6$)-alkyl—$S(O)n$—$(CH_2)_n$—,
(l) hydroxy-($C_1$-$C_6$)-alkyl,
(m) —$CF_3$,
(n) —$CO_2R^7$,
(o) —OH,
(p) —$NR^7R^{11}$,
(q) —$[(C_1$-$C_6)$-alkyl]$NR^7R^{11}$,
(r) —$NO_2$,
(s) —$(CH_2)_n$—$SO_2$—$N(R^7)_2$,
(t) —$NR^7CO$-($C_1$-$C_4$)-alkyl, or
(u) —$CON(R^7)_2$;

$R^{11}$ is
(a) ($C_1$-$C_6$)-alkyl,
(b) phenyl,
(c) —($C_1$-$C_4$)-alkyl-phenyl, or
(d) ($C_3$-$C_7$)-cycloalkyl;

$R^{12}$ is
(a) H,
(b) ($C_1$-$C_6$)-alkyl, unsubstituted or substituted with one or two substituents selected from the group consisting of:
  (i) —OH,
  (ii) —O—($C_1$-$C_4$)-alkyl,
  (iii) —O—($C_1$-$C_4$)-cycloalkyl,
  (iv) —$S(O)_n$—($C_1$-$C_4$)-alkyl,
  (v) —$NR^7$—($C_1$-$C_4$)-alkyl, (vi) —NR$^7$R$^{11}$,
(vii) —COOR$^7$,
(viii) —CONHR$^7$,
(ix) —OCOR$^{11}$,
(x) —CONR$^7$R$^{11}$,
(xi) —NR$^7$CONR$^7$R$^{11}$,
(xii) —NR$^7$COOR$^{11}$,
(xiii) —C(R$^6$)(OH)—C(R$^6$)(R$^7$)(OH), or
(xiv) —SO$_2$NR$^7$R$^{11}$,
(c) (C$_3$-C$_7$)-cycloalkyl,
(d) (C$_1$-C$_4$)-perfluoroalkyl,
(e) aryl, unsubstituted or substituted with one to three substituents selected from the group consisting of:
(i) F, Cl, Br, I,
(ii) (C$_1$-C$_6$)-alkyl,
(iii) (C$_1$-C$_6$)-alkoxy,
(iv) hydroxy-(C$_1$-C$_6$)-alkyl,
(v) —CF$_3$,
(vi) —COOR$^7$,
(vii) —OH,
(viii) —NR$^7$R$^{11}$,
(ix) —NH$_2$,
(x) —NO$_2$,
(xi) —CONR$^7$R$^{11}$,
(xii) two adjacent groups may be joined together to form a methylenedioxy group,
(f) aryl(C$_1$-C$_2$)alkyl unsubstituted or substituted with one to three substituents selected from the group consisting of:
(i) F, Cl, Br, I,
(ii) (C$_1$-C$_6$)-alkyl,
(iii) (C$_1$-C$_6$)-alkoxy,
(iv) hydroxy-(C$_1$-C$_6$)-alkyl,
(v) —CF$_3$,
(vi) —COOR$^7$,
(vii) —OH,
(viii) —NR$^7$R$^{11}$,
(ix) —NH$_2$,
(x) —NO$_2$,
(xi) —CONR$^7$R$^{11}$,
(xii) two adjacent groups may be joined together to form a methylenedioxy group,
(g) heteroaryl, wherein heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl or carbazolyl and is unsubstituted or substituted with one or two substituents selected from the group consisting of:
(i) F, Cl, Br, I,
(ii) (C$_1$-C$_6$)-alkyl,
(iii) (C$_1$-C$_6$)-alkoxy,
(iv) —CF$_3$,
(v) —COOR$^7$,
(vi) —NR$^7$R$^{11}$,
(vii) —NH$_2$,
(viii) —NO$_2$, or
(ix) —CONR$^7$R$^{11}$;
X is
(a)
(b) —S(O)n—,
(c) —NR$^7$—,
(d) —CH$_2$O—,
(e) —CH$_2$S(O)n—,
(f) —CH$_2$NR$^7$—,
(g) —OCH$_2$—,
(h) —N(R$^7$)CH$_2$—,
(i) —S(O)$_n$CH$_2$—,
(j) —single bond, or
(k) —C(R$^9$)$_2$—;
Z is:
(a) —CO$_2$H,
(b) —CO$_2$R$^{13}$,
(c) —CONH-(tetrazol-5-yl),
(d) —CONHSO$_2$-phenyl, wherein phenyl is unsubstituted or substituted with one or two substituents selected from the group consisting of:
i) (C$_1$-C$_4$)-alkyl,
ii) —O—(C$_1$-C$_4$)-alkyl,
iii) —CONR$^7$R$^{11}$,
iv) F, Cl, Br or I,
v) —COOR$^7$,
vi) (C$_1$-C$_4$)-perfluoroalkyl,
vii) (C$_3$-C$_7$)-cycloalkyl,
viii) NR$^7$R$^{11}$,
(ix) SO$_2$NR$^7$R$^{11}$,
x) hydroxy, or
xi) 2,3-, or 3,4-methylenedioxy,
(e) —CONHSO$_2$—(C$_1$-C$_8$)-alkyl, wherein the alkyl group is unsubstituted or substituted as defined in R$^4$(b),
(f) —CONHSO$_2$—(C$_1$-C$_4$)-perfluoroalkyl,
(g) —CONHSO$_2$—(C$_3$-C$_7$)-cycloalkyl,
(h) —tetrazol-5-yl,
(i) —CONHSO$_2$-heteroaryl, wherein heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl or carbazolyl,
(j) —SO$_2$NHCO-phenyl, wherein phenyl is as defined in Z(d) above,
(k) —SO$_2$NHCO-(C$_1$-C$_8$)-alkyl, wherein the alkyl group is unsubstituted or substituted as defined in R$^4$(b),
(l) —SO$_2$NHCO-(C$_1$-C$_4$)-perfluoroalkyl,
(m) —SO$_2$NHCO-heteroaryl, wherein heteroaryl is as defined in Z(h) above,
(n) —SO$_2$NHCON(R$^{11}$)$_2$ wherein the R$^{11}$ groups are the same or different,
(o) —PO(OR$^7$)$_2$, wherein the R$^7$ groups are the same or different, or
(p) —PO(R$^{11}$)OR$^{71}$
R$^{13}$ is:
(a) (C$_1$-C$_4$)-alkyl,
(b) CHR$^{14}$—O—COR$^{15}$,
(c) CH$_2$CH$_2$—N[(C$_1$-C$_2$)-alkyl]$_2$,
(d) CH$_2$CH$_2$—N[CH$_2$CH$_2$]$_2$O,
(e) (CH$_2$CH$_2$O)y—O—[(C$_1$-C$_4$)-alkyl], wherein y is 1 or 2,
(f) phenyl, naphthyl, CH$_2$-phenyl or CH$_2$-naphthyl, where phenyl or naphthyl is substituted or unsubstituted with CO$_2$—(C$_1$-C$_4$)-alkyl,

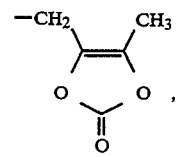 (g)

-continued

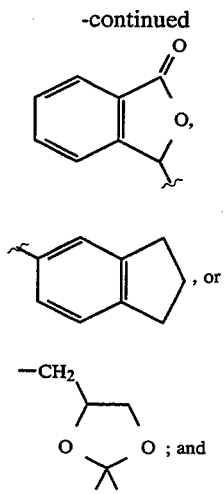

(h)

(i) , or (j) —CH₂—

R¹⁴ and R¹⁵ independently are $(C_1-C_6)$-alkyl or phenyl,

R¹⁶, R¹⁷ and R¹⁸ are independently:
(a) H,
(b) $(C_1-C_6)$-alkyl, unsubstituted or substituted with one or two substituents selected from the group consisting of:
  (i) —OH,
  (ii) —O—$(C_1-C_4)$-alkyl,
  (iii) —NR⁷R¹¹,
  (iv) —COOR⁷,
  (v) —CONR⁷R¹¹,
  (vi) —SO₂NR⁷R¹¹,
  (vii) —NH₂,
  (viii) —NO₂,
(c) $(C_3-C_7)$-cycloalkyl,
(d) $(C_1-C_4)$-perfluoroalkyl,
(e) F, Cl, Br, I,
(f) —OH,
(g) $(C_1-C_4)$-alkoxy,
(h) —COOR⁷,
(i) —CONR⁷R¹¹,
(j) —CONHSO₂—$(C_1-C_6)$-alkyl wherein the alkyl group is unsubstituted or substituted as defined in R⁴(b),
(k) —CONHSO₂-phenyl wherein the phenyl group is unsubstituted or substituted as defined in Z(d),
(l) —NR⁷R¹¹,
(m) —NH₂,
(n) —NO₂,
(o) —NR⁷COR¹¹,
(p) —NR⁷COOR¹¹,
(q) —NR⁷CONR⁷R¹¹,
(r) two adjacent groups may be joined together to form a methylenedioxy group,
(s) —SO₂NR⁷R¹¹,
(t) —SO₂NHCO—$(C_1-C_6)$-alkyl wherein the alkyl group is unsubstituted or substituted as defined in R⁴(b),
(u) —SO₂NHCO-phenyl wherein the phenyl group is unsubstituted or substituted as defined in Z(d).

A subclass of compounds of the invention are the compounds of Formula III:

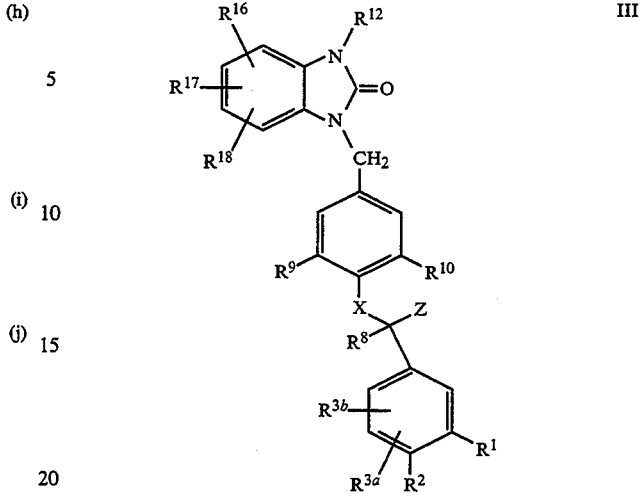

or a pharmaceutically acceptable salt thereof, wherein:
R¹, R², R³ᵃ and R³ᵇ are independently:
(a) H,
(b) F, Cl, Br, or I,
(c) —NO₂,
(d) $(C_1-C_4)$-alkyl,
(e) —OR⁷,
(f) —NHCO—$(C_1-C_4)$-alkyl,
(g) —NHCO—O$(C_1-C_4)$-alkyl,
(h) —O—$(CH_2)_m$—OR⁷,
(i) —CONR⁷R¹¹, or
(j) —COOR⁷;
m is 2, 3 or 4,
R¹ and R² on adjacent carbon atoms can be joined together to form a ring structure:

A ;

A represents:
(a) —Y—C(R⁴)=C(R⁵)—,
(b) —Y—C(R⁴)=N—,
(c) —Y—N=C(R⁴)—,
(d) —Y—[C(R⁶)(R⁶)]ₛ—Y—,
(e) —Y—C(R⁶)(R⁶)—C(R⁶)(R⁶)—,
(f) —C(R⁴)=C(R⁵)—Y—,
(g) —N=C(R⁴)—Y—,
(h) —C(R⁶)(R⁶)—C(R⁶)(R⁶)—Y—, or
(i) —C(R⁴)=C(R⁵)—C(R⁴)=C(R⁵)—;
s is 1 or 2;
Y is —O—, —S— and NR⁷;
R⁴ and R⁵ are independently:
(a) H,
(b) $(C_1-C_6)$-alkyl,
(c) $(C_3-C_7)$-cycloalkyl,
(d) F, Cl, Br, I,
(e) —NR⁷COOR¹¹,
(f) —SO₂NR⁷R¹¹,
(g) —O—$(C_1-C_4)$-alkyl,
(h) —S(O)ₙ—$(C_1-C_4)$-alkyl, or
(i) —NHSO₂R¹¹;
R⁶ is:
(a) H, or
(b) $(C_1-C_4)$-alkyl, or (c) F;

R$^7$ is:
(a) H,
(b) (C$_1$-C$_6$)-alkyl,
(c) phenyl, or
(d) benzyl;

R$^8$ is:
(a) H,
(b) (C$_1$-C$_6$)-alkyl, or
(c) phenyl;

R$^9$ and R$^{10}$ are independently:
(a) H,
(b) (C$_1$-C$_6$)-alkyl, unsubstituted or substituted with (C$_3$-C$_7$)-cycloalkyl,
(c) Cl, Br, F, I,
(d) (C$_1$-C$_6$)-alkoxy, or
(e) hydroxy-(C$_1$-C$_6$)-alkyl;

R$^{11}$ is
(a) (C$_1$-C$_6$)-alkyl,
(b) phenyl,
(c) —(C$_1$-C$_4$)-alkyl-phenyl, or
(d) (C$_3$-C$_7$)-cycloalkyl;

R$^{12}$ is
(a) H,
(b) (C$_1$-C$_6$)-alkyl, unsubstituted or substituted with one or two substituents selected from the group consisting of:
 (i) —OH,
 (ii) —O—(C$_1$-C$_4$)-alkyl,
 (iii) —O—(C$_1$-C$_4$)-cycloalkyl,
 (iv) —S(O)$_n$—(C$_1$-C$_4$)-alkyl,
 (v) —NR$^7$—(C$_1$-C$_4$)-alkyl,
 (vi) —NR$^7$R$^{11}$,
 (vii) —COOR$^7$,
 (viii) —CONHR$^7$,
 (ix) —OCOR$^{11}$,
 (x) —CONR$^7$R$^{11}$,
 (xi) —NR$^7$CONR$^7$R$^{11}$,
 (xii) —NR$^7$COOR$^{11}$,
 (xiii) —C(R$^6$)(OH)—C(R$^6$)(R$^7$)(OH), or
 (xiv) —SO$_2$NR$^7$R$^{11}$,
(c) (C$_3$-C$_7$)-cycloalkyl,
(d) (C$_1$-C$_4$)-perfluoroalkyl,
(e) aryl, unsubstituted or substituted with one to three substituents selected from the group consisting of:
 (i) F, Cl, Br, I,
 (ii) (C$_1$-C$_6$)-alkyl,
 (iii) (C$_1$-C$_6$)-alkoxy,
 (iv) hydroxy-(C$_1$-C$_6$)-alkyl,
 (v) —CF$_3$,
 (vi) —COOR$^7$,
 (vii) —OH,
 (viii) —NR$^7$R$^{11}$,
 (ix) —NH$_2$,
 (x) —NO$_2$,
 (xi) —CONR$^7$R$^{11}$,
 (xii) two adjacent groups may be joined together to form a methylenedioxy group,
(f) aryl(C$_1$-C$_2$)alkyl unsubstituted or substituted with one to three substituents selected from the group consisting of:
 (i) F, Cl, Br, I,
 (ii) (C$_1$-C$_6$)-alkyl,
 (iii) (C$_1$-C$_6$)-alkoxy,
 (iv) hydroxy-(C$_1$-C$_6$)-alkyl,
 (v) —CF$_3$,
 (vi) —COOR$^7$,
 (vii) —OH,
 (viii) —NR$^7$R$^{11}$,
 (ix) —NH$_2$,
 (x) —NO$_2$,
 (xi) —CONR$^7$R$^{11}$,
 (xii) two adjacent groups may be joined together to form a methylenedioxy group,
(g) heteroaryl, wherein heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl or carbazolyl and is unsubstituted or substituted with one or two substituents selected from the group consisting of:
 (i) F, Cl, Br, I,
 (ii) (C$_1$-C$_6$)-alkyl,
 (iii) (C$_1$-C$_6$)-alkoxy,
 (iv) —CF$_3$,
 (v) —COOR$^7$,
 (vi) —NR$^7$R$^{11}$,
 (vii) —NH$_2$,
 (viii) —NO$_2$, or
 (ix) —CONR$^7$R$^{11}$;

X is
(a) —O—,
(b) —NR$^7$—,
(c) —single bond, or
(d) —C(R$^9$)$_2$—;

Z is:
(a) —CO$_2$H,
(b) —CO$_2$R$^{13}$,
(c) —CONH-(tetrazol-5-yl),
(d) —CONHSO$_2$-phenyl, wherein phenyl is unsubstituted or substituted with one or two substituents selected from the group consisting of:
 i) (C$_1$-C$_4$)-alkyl,
 ii) —O—(C$_1$-C$_4$)-alkyl,
 iii) —CONR$^7$R$^{11}$,
 iv) F, Cl, Br or I,
 v) —COOR$^7$,
 vi) (C$_1$-C$_4$)-perfluoroalkyl,
 vii) (C$_3$-C$_7$)-cycloalkyl,
 viii) NR$^7$R$^{11}$,
 ix) SO$_2$NR$^7$R$^{11}$,
 x) hydroxy, or
 xi) 2,3-, or 3,4-methylenedioxy;
(e) —CONHSO$_2$—(C$_1$-C$_8$)-alkyl, wherein alkyl is unsubstituted or substituted as defined in R$^4$(b),
(f) —CONHSO$_2$-heteroaryl, wherein heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl or carbazolyl, or
(g) —CONHSO$_2$—(C$_3$-C$_7$)-cycloalkyl, or
(h) —tetrazol-5-yl;

R$^{13}$ is:
(a) (C$_1$-C$_4$)-alkyl,
(b) CHR$^{14}$—O—COR$^{15}$,
(c) CH$_2$CH$_2$—N[(C$_1$-C$_2$)-alkyl]$_2$,
(d) CH$_2$CH$_2$—N[CH$_2$CH$_2$]$_2$O,
(e) (CH$_2$CH$_2$O)$_y$—O—[(C$_1$-C$_4$)-alkyl], wherein y is 1 or 2,
(f) phenyl, naphthyl, CH$_2$-phenyl or CH$_2$-naphthyl, where phenyl or naphthyl is substituted or unsubstituted with CO$_2$—(C$_1$-C$_4$)-alkyl,

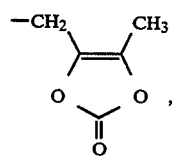 (g)

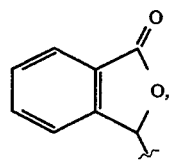 (h)

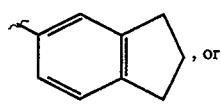, or (i)

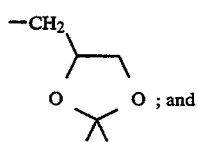; and (j)

$R^{14}$ and $R^{15}$ independently are $(C_1-C_6)$-alkyl or phenyl, $R^{16}$, $R^{17}$ and $R^{18}$ are independently:
(a) H,
(b) $(C_1-C_6)$-alkyl,
(c) F, Cl, Br, I,
(d) $(C_1-C_4)$-alkoxy,
(e) —COOR$^7$,
(f) —CONR$^7$R$^{11}$,
(g) —CONHSO$_2$—$(C_1-C_6)$-alkyl wherein the alkyl group is unsubstituted or substituted as defined in R$^4$(b),
(h) —CONHSO$_2$-phenyl wherein the phenyl group is unsubstituted or substituted as defined in Z(d).

Another subclass of compounds of the invention are the compounds of Formula IV:

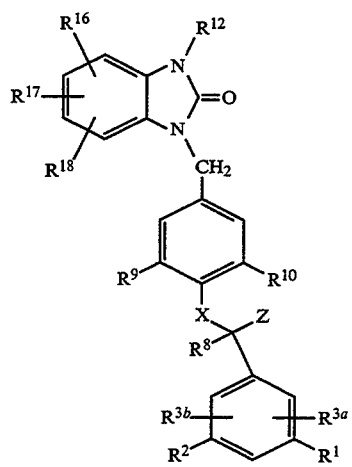 IV or a pharmaceutically acceptable salt thereof, wherein:
$R^1$, $R^2$, $R^{3a}$ and $R^{3b}$ are independently:
(a) H,
(b) F, Cl, Br, or I,
(c) —NO$_2$,
(d) $(C_1-C_4)$-alkyl,
(e) —OR$^7$,
(f) —NHCO—$(C_1-C_4)$-alkyl,
(g) —NHCO—O$(C_1-C_4)$-alkyl,
(h) —O—$(CH_2)_m$—OR$^7$,
(i) —CONR$^7$R$^{11}$, or
(j) —COOR$^7$;

m is 2, 3 or 4,
n is 0, 1 or 2,
$R^7$ is:
(a) H,
(b) $(C_1-C_6)$-alkyl,
(c) phenyl, or
(d) benzyl;
$R^8$ is:
(a) H,
(b) $(C_1-C_6)$-alkyl, or
(c) phenyl;
$R^9$ and $R^{10}$ are independently:
(a) H,
(b) $(C_1-C_6)$-alkyl, unsubstituted or substituted with $(C_3-C_7)$-cycloalkyl,
(c) Cl, Br, F, I,
(d) $(C_1-C_6)$-alkoxy, or
(e) hydroxy-$(C_1-C_6)$-alkyl;
$R^{11}$ is
(a) $(C_1-C_6)$-alkyl,
(b) phenyl,
(c) —$(C_1-C_4)$-alkyl-phenyl, or
(d) $(C_3-C_7)$-cycloalkyl;
$R^{12}$ is
(a) H,
(b) $(C_1-C_6)$-alkyl, unsubstituted or substituted with one or two substituents selected from the group consisting of:
(i) —OH,
(ii) —O—$(C_1-C_4)$-alkyl,
(iii) —O—$(C_1-C_4)$-cycloalkyl,
(iv) —S(O)$_n$—$(C_1-C_4)$-alkyl,
(v) —NR$^7$—$(C_1-C_4)$-alkyl,
(vi) —NR$^7$R$^{11}$,
(vii) —COOR$^7$,
(viii) —CONHR$^7$,
(ix) —OCOR$^{11}$,
(x) —CONR$^7$R$^{11}$,
(xi) —NR$^7$CONR$^7$R$^{11}$,
(xii) —NR$^7$COOR$^{11}$,
(xiii) —C(R$^6$)(OH)—C(R$^6$)(R$^7$)(OH), or
(xiv) —SO$_2$NR$^7$R$^{11}$,
(c) $(C_3-C_7)$-cycloalkyl,
(d) $(C_1-C_4)$-perfluoroalkyl,
(e) aryl, unsubstituted or substituted with one to three substituents selected from the group consisting of:
(i) F, Cl, Br, I,
(ii) $(C_1-C_6)$-alkyl,
(iii) $(C_1-C_6)$-alkoxy,
(iv) hydroxy-$(C_1-C_6)$-alkyl,
(v) —CF$_3$,
(vi) —COOR$^7$,
(vii) —OH,
(viii) —NR$^7$R$^{11}$,
(ix) —NH$_2$,
(x) —NO$_2$,
(xi) —CONR$^7$R$^{11}$,
(xii) two adjacent groups may be joined together to form a methylenedioxy group, (f) aryl($C_1$-$C_2$)alkyl unsubstituted or substituted with one to three substituents selected from the group consisting of:
  (i) F, Cl, Br, I,
  (ii) ($C_1$-$C_6$)-alkyl,
  (iii) ($C_1$-$C_6$)-alkoxy,
  (iv) hydroxy-($C_1$-$C_6$)-alkyl,
  (v) —$CF_3$,
  (vi) —$COOR^7$,
  (vii) —OH,
  (viii) —$NR^7R^{11}$,
  (ix) —$NH_2$,
  (x) —$NO_2$,
  (xi) —$CONR^7R^{11}$,
  (xii) two adjacent groups may be joined together to form a methylenedioxy group, heteroaryl, wherein heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl or carbazolyl and is unsubstituted or substituted with one or two substituents selected from the group consisting of:
    (i) F, Cl, Br, I,
    (ii) ($C_1$-$C_6$)-alkyl,
    (iii) ($C_1$-$C_6$)-alkoxy,
    (iv) —$CF_3$,
    (v) —$COOR^7$,
    (vi) —$NR^7R^{11}$,
    (vii) —$NH_2$,
    (viii) —$NO_2$,
    (ix) —$CONR^7R^{11}$, X is
  (a) —O—,
  (b) —$NR^7$—,
  (c) —single bond, or
  (d) —$C(R^9)_2$—;

Z is:
  (a) —$CO_2H$,
  (b) —$CO_2R^{13}$,
  (c) —CONH-(tetrazol-5-yl),
  (d) —$CONHSO_2$-phenyl, wherein phenyl is unsubstituted or substituted with one or two substituents selected from the group consisting of:
    i) ($C_1$-$C_4$)-alkyl,
    ii) —O—($C_1$-$C_4$)-alkyl,
    iii) —$CONR^7R^{11}$,
    iv) F, Cl, Br or I,
    v) —$COOR^7$,
    vi) ($C_1$-$C_4$)-perfluoroalkyl,
    vii) ($C_3$-$C_7$)-cycloalkyl,
    viii) $NR^7R^{11}$,
    ix) $SO_2NR^7R^{11}$,
    x) hydroxy, or
    xi) 2,3-, or 3,4-methylenedioxy;
  (e) —$CONHSO_2$—($C_1$-$C_8$)-alkyl, wherein alkyl is unsubstituted or substituted as defined in $R^4$(b),
  (f) —$CONHSO_2$-heteroaryl, wherein heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl or carbazolyl, or
  (g) —$CONHSO_2$—($C_3$-$C_7$)-cycloalkyl,
  (h) —tetrazol-5-yl;

$R^{13}$ is:
  (a) ($C_1$-$C_4$)-alkyl,
  (b) $CHR^{14}$—O—$COR^{15}$,
  (c) $CH_2CH_2$—N[($C_1$-$C_2$)-alkyl]$_2$,
  (d) $CH_2CH_2$—N[$CH_2CH_2$]$_2$O,
  (e) ($CH_2CH_2O)_y$—O—[($C_1$-$C_4$)-alkyl], wherein y is 1 or 2,
  (f) phenyl, naphthyl, $CH_2$-phenyl or $CH_2$-naphthyl, where phenyl or naphthyl is substituted or unsubstituted with $CO_2$—($C_1$-$C_4$)-alkyl,

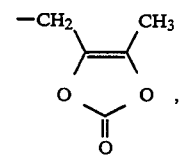  (g)

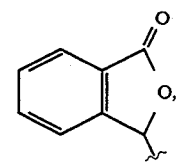  (h)

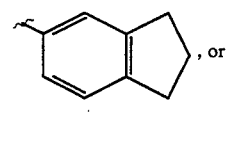  (i)

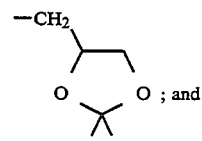  (j)

$R^{14}$ and $R^{15}$ independently are ($C_1$-$C_6$)-alkyl or phenyl; and $R^{16}$, $R^{17}$ and $R^{18}$ are independently:
  (a) H,
  (b) ($C_1$-$C_6$)-alkyl,
  (c) F, Cl, Br, I,
  (d) ($C_1$-$C_4$)-alkoxy,
  (e) —$COOR^7$,
  (f) —$CONR^7R^{11}$,
  (g) —$CONHSO_2$—($C_1$-$C_6$)-alkyl wherein the alkyl group is unsubstituted or substituted as defined in $R^4$(b),
  (h) —$CONHSO_2$-phenyl wherein the phenyl group is unsubstituted or substituted as defined in Z(d).

The following Tables (I-IV) further exemplify the scope of the invention described by formulae V-VIII (wherein $R^{16}$, $R^{17}$ and $R^{18}$ are H, unless specified otherwise).

TABLE I

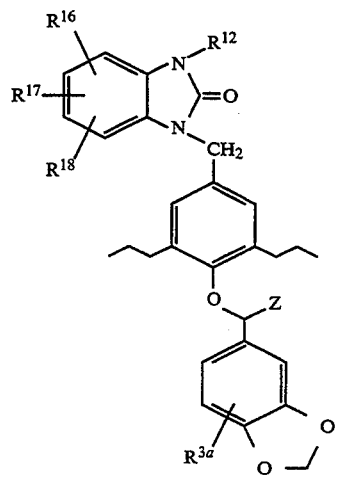

V

| $R^{3a}$ | $R^{12}$ | $R^{16}, R^{17}, R^{18}$ | Z |
|---|---|---|---|
| H | H | | COOH |
| H | Me | | COOH |
| H | Et | | COOH |
| H | nPr | | COOH |
| H | iPr | | COOH |
| H | nBu | | COOH |
| H | iBu | | COOH |
| H | tBu | | COOH |
| H | Ph | | COOH |
| H | 2-Pyridyl | | COOH |
| H | 3-Pyridyl | | COOH |
| H | 4-Pyridyl | | COOH |
| H | H | 4-Me | COOH |
| H | H | 5-Me | COOH |
| H | H | 6-Me | COOH |
| H | H | 5,6-diMe | COOH |
| H | Me | 5-Me | COOH |
| H | Me | 6-Me | COOH |
| H | CH₂COOH | | COOH |
| H | CH₂COOH | 5-Me | COOH |
| H | CH₂COOH | 6-Me | COOH |
| H | H | | CONHSO₂iPr |
| H | H | | CONHSO₂Ph(4-iPr) |
| H | Me | | CONHSO₂Ph(4-tBu) |
| H | Me | | CONHSO₂iPr |
| H | Me | | CONHSO₂Ph(4-iPr) |
| H | Me | | CONHSO₂Ph(4-tBu) |
| 5-OMe | H | | COOH |
| 5-OMe | Me | | COOH |
| 5-OMe | Et | | COOH |
| 5-OMe | nPr | | COOH |
| 5-OMe | iPr | | COOH |
| 5-OMe | nBu | | COOH |
| 5-OMe | iBu | | COOH |
| 5-OMe | Ph | | COOH |
| 5-OMe | 2-Pyridyl | | COOH |
| 5-OMe | H | 5-Me | COOH |
| 5-OMe | H | 6-Me | COOH |
| 5-OMe | Me | 5-Me | COOH |
| 5-OMe | Me | 6-Me | COOH |
| 5-Br | Me | | COOH |
| 5-Br | Et | | COOH |
| 5-Br | nPr | | COOH |
| 5-Br | iPr | | COOH |
| 5-Br | nBu | | COOH |
| 5-Br | iBu | | COOH |
| 5-Br | Ph | | COOH |
| 5-Br | 2-Pyridyl | | COOH |
| 5-Br | H | 5-Me | COOH |
| 5-Br | H | 6-Me | COOH |
| 5-Br | Me | 5-Me | COOH |
| 5-Br | Me | 6-Me | COOH. |

TABLE II

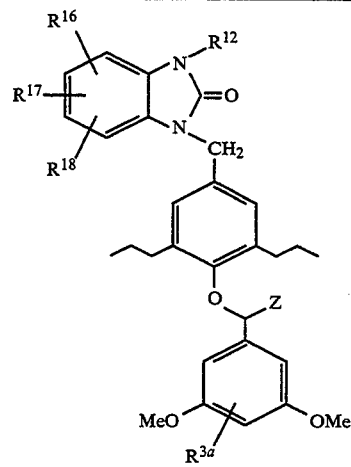

VI

| $R^{3a}$ | $R^{12}$ | $R^{16}, R^{17}, R^{18}$ | Z |
|---|---|---|---|
| H | H | | COOH |
| H | Me | | COOH |
| H | Et | | COOH |
| H | nPr | | COOH |
| H | iPr | | COOH |
| H | nBu | | COOH |
| H | iBu | | COOH |
| H | Ph | | COOH |
| H | 2-Pyridyl | | COOH |
| H | H | 5-Me | COOH |
| H | H | 6-Me | COOH |
| H | Me | 5-Me | COOH |
| H | Me | 6-Me | COOH |

TABLE III

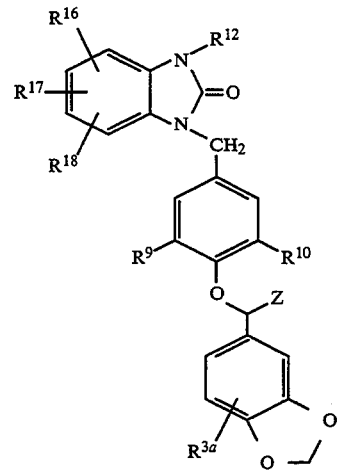

VII

| $R^{3a}$ | $R^9$ | $R^{10}$ | $R^{12}$ | $R^{16}, R^{17}, R^{18}$ | Z |
|---|---|---|---|---|---|
| H | nPr | H | H | | COOH |
| H | nPr | H | Me | | COOH |
| H | nPr | H | Et | | COOH |
| H | nPr | H | H | 5-Me | COOH |
| H | nPr | H | H | 6-Me | COOH |
| H | nPr | H | Me | 5-Me | COOH |
| H | nPr | H | Me | 6-Me | COOH |
| H | nPr | H | H | | CONHSO₂iPr |
| H | nPr | H | Me | | CONHSO₂ipr |
| H | nPr | H | Et | | CONHSO₂iPr |
| H | nPr | H | H | 5-Me | CONHSO₂iPr |
| H | nPr | H | H | 6-Me | CONHSO₂iPr |
| H | nPr | H | Me | 5-Me | CONHSO₂iPr |
| H | nPr | H | Me | 6-Me | CONHSO₂iPr |
| H | nPr | H | H | | CONHSO₂Ph(4-iPr) |
| H | nPr | H | Me | | CONHSO₂Ph(4-iPr) |

TABLE III-continued

VII

| $R^{3a}$ | $R^9$ | $R^{10}$ | $R^{12}$ | $R^{16}, R^{17}, R^{18}$ | Z |
|---|---|---|---|---|---|
| H | nPr | H | Et | | CONHSO₂Ph(4-ipr) |
| H | nPr | H | H | 5-Me | CONHSO₂Ph(4-iPr) |
| H | nPr | H | H | 6-Me | CONHSO₂Ph(4-ipr) |
| H | nPr | H | Me | 5-Me | CONHSO₂Ph(4-iPr) |
| H | nPr | H | Me | 6-Me | CONHSO₂Ph(4-iPr) |
| 5-OMe | nPr | H | H | | CONHSO₂iPr |
| 5-OMe | nPr | H | H | | CONHSO₂Ph(4-iPr) |
| 5-OMe | nPr | H | Et | | CONHSO₂iPr |
| 5-OMe | nPr | H | Et | | CONHSO₂Ph(4-iPr) |
| H | Et | H | H | H | COOH |
| H | Et | H | Et | H | COOH |
| H | Et | H | H | H | CONHSO₂iPr |
| H | Et | H | H | H | CONHSO₂Ph(4-iPr) |
| H | Et | H | Et | H | CONHSO₂iPr |
| H | Et | H | Et | H | CONHSO₂Ph(4-iPr) |
| H | nPr | Cl | H | | COOH |
| H | nPr | Cl | Me | | COOH |
| H | nPr | Cl | Et | | COOH |
| H | nPr | Cl | H | 5-Me | COOH |
| H | nPr | Cl | H | 6-Me | COOH |
| H | nPr | Cl | Me | 5-Me | COOH |
| H | nPr | Cl | Me | 6-Me | COOH |
| H | Cl | Cl | H | | COOH |
| H | Cl | Cl | Et | | COOH |
| H | Cl | Cl | Me | 6-Me | COOH |
| H | H | H | H | | COOH |
| H | H | H | Et | | COOH |
| H | H | H | H | | CONHSO₂iPr |
| H | H | H | Et | | CONHSO₂iPr |
| H | H | H | H | | CONHSO₂Ph(4-iPr) |
| H | H | H | Et | | CONHSO₂Ph(4-iPr) |
| H | OMe | OMe | H | | COOH |
| H | OMe | OMe | Et | | COOH |

TABLE IV

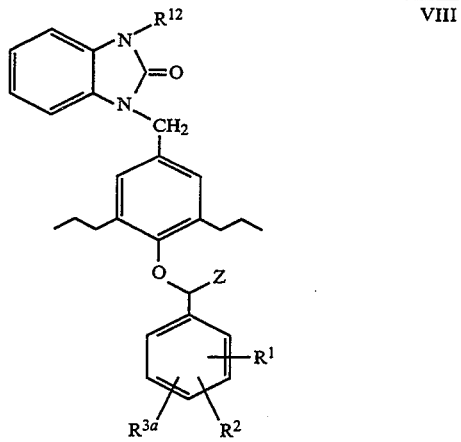

VIII

| $R^1, R^2, R^{3a}$ | $R^{12}$ | Z |
|---|---|---|
| 3-Me | H | COOH |
| 3-Me | Et | COOH |
| 3-Cl | H | COOH |
| 3-Cl | Et | COOH |
| 3-OMe | H | COOH |
| 3-OMe | Et | COOH |
| 3,5-diSMe | H | COOH |
| 3,5-diSMe | Et | COOH |
| 1'-Me-3,4-methylenedioxy | H | COOH |
| 1'-Me-3,4-methylenedioxy | Et | COOH. |

The alkyl substituents recited above denote straight and branched chain hydrocarbons of the length specified such as methyl, ethyl, isopropyl, isobutyl, neopentyl, isopentyl, etc.

The alkenyl-substituents denote alkyl groups as described above which are modified so that each contains a carbon to carbon double bond such as vinyl, allyl and 2-butenyl.

Cycloalkyl denotes rings composed of 3 to 8 methylene groups, each of which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl or carbazolyl.

Although the reaction schemes described below are reasonably general, it will be understood by those skilled in the art of organic synthesis that one or more functional groups present in a given compound of Formula I may render the molecule incompatible with a particular synthetic sequence. In such a case an alternative synthetic route, an altered order of steps, or a strategy of protection and deprotection may be employed. In all cases the particular reaction conditions, including reagents, solvent, temperature and time, should be chosen so that they are consistent with the nature of the functionality present in the molecule.

The compounds of Formula I and specifically compounds of Formula II can be synthesized using the reactions and techniques described for the synthesis of the non-heterocyclic components in the patent application WO91/11999 (Merck & Co.; published on Aug. 22, 1991 under the Patent Cooperation Treaty) and also U.S. Pat. No. 5,177,095 (Merck & Co.; Jan. 5, 1993).

The reaction schemes described below have been generalized for simplicity. It is further to be understood that in the generalized schemes below, unless specified more narrowly in the text, the alkyl and aryl groups represent unfunctionalized or functionalized derivatives as described before. The leaving group Q present in the alkylating agents is either chloro, bromo, iodo, methanesulfonate, p-toluenesulfonate or triflate.

in carbon tetrachloride with N-bromosuccinimide and a catalytic amount of a radical initiator (e.g., AIBN or benzoyl peroxide) to provide the 2-bromoarylacetic acid ester 5.

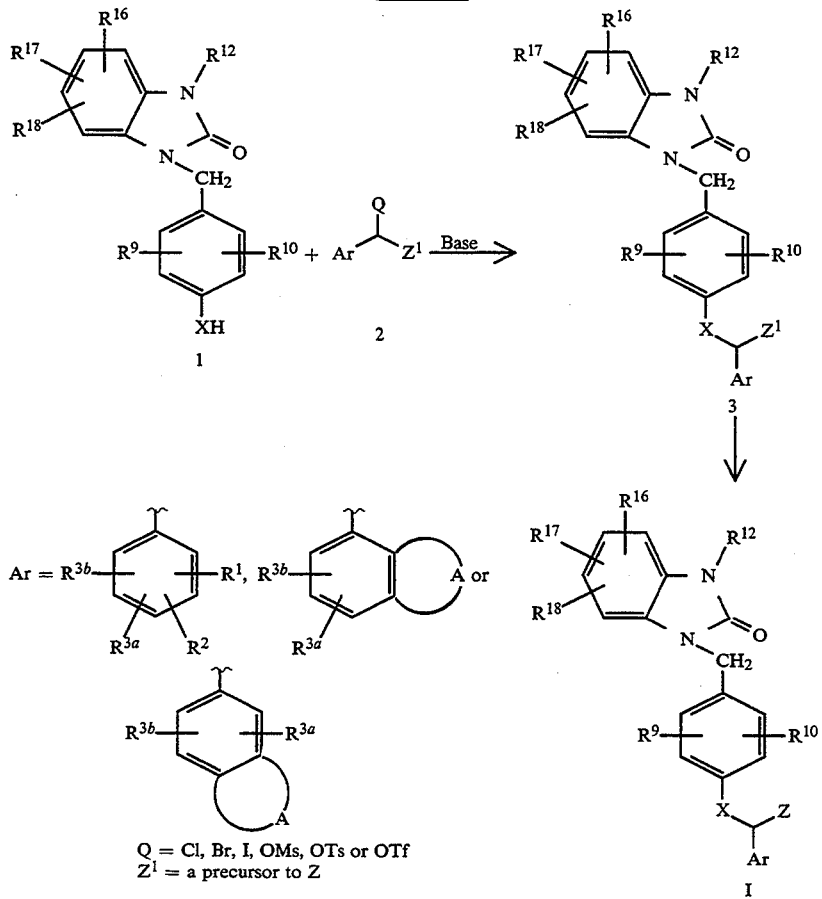

The compounds of Formula I (where X is oxygen, sulfur or appropriately substituted nitrogen) can be synthesized as outlined in Scheme 1. The substituted compound 1 may be reacted with the alkylating agent 2 in an appropriate solvent such as alcohols (methanol, ethanol, isopropanol and like), dimethylformamide (DMF), dimethylsulfoxide (DMSO), tetrahydrofuran (THF) and acetone in the presence of an alkali metal salt such as alkoxides, carbonates, hydroxides and hydrides, or organic bases such as trialkylamines or alkyl lithiums to provide compound 3. The $Z^1$ group present in compound 3 may then be further transformed to provide the appropriate compounds of Formula I.

In general, the alkylating agent 2 can be prepared using methods and techniques outlined in U.S. Pat. No. 5,177,095. More specifically, compound 2 (where $Z^1$ is COOR and Q is Br) can be synthesized from the substituted arylacetic acids 4 as outlined in Scheme 2. The substituted arylacetic acid 4 is converted to the corresponding ester either by refluxing the acid in an appropriate alcohol in the presence of a catalytic amount of conc. sulfuric acid, or using other conventional methods of esterification. The resulting ester is then refluxed

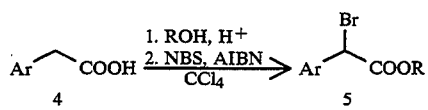

Alternatively, the ester 5 may also be prepared from appropriate aryl aldehydes (Scheme 3). The aldehyde 6 can be reacted with trimethylsilyl cyanide and catalytic amounts of KCN and 18-crown-6 to provide the corresponding trimethylsilyl cyanohydrin 7, which upon further treatment with the gaseous HCl and ethanol affords the 2-hydroxy ester 8. The ester 8 is treated with triphenylphosphine and carbon tetrabromide in methylene chloride to give the 2-bromoarylacetate derivatives 5.

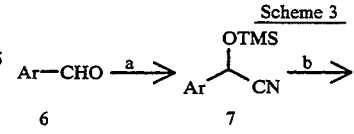

-continued
Scheme 3

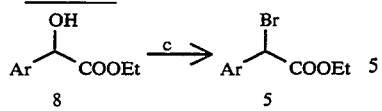

a. TMSCN, Cat. KCN, CH$_2$Cl$_2$, 18-Crown-6;
b. HCl(g), EtOH;
c. CBr$_4$, Ph$_3$P, CH$_2$Cl$_2$ Scheme 4 illustrates a typical synthesis of an alkylating agent 5 (where Ar represents a heterocycle such as an indole). The appropriately substituted cyanoindole 9 (for a general synthesis of substituted indoles refer to, R. K. Brown, *Indoles, Part One*, Ed. W. J. Houlihan, Vol. 25, Chapter II, Wiley-Interscience, New York, 1972) is reduced with DIBAL-H to provide the corresponding aldehyde, which is then converted into the N-Boc derivative 10. Reaction of 10 with the trichloromethide anion [generated from KOH and CHCl$_3$; J. M. Wyvratt et. al., *J. Org. Chem.*, 52, 944–945 (1987)] followed by treatment with aqueous NaOH in DMF provides the alcohol 11. Treatment of 11 with diazomethane followed by the reaction with CBr$_4$/Ph$_3$P yields the alkylating agent 12.

A typical synthesis of alkylating agents bearing a substituted benzoxazole or benzthiazole ring is outlined in Scheme 5. The substituted benzoxazole 14 is prepared from the corresponding o-aminophenol 13 by the reaction of an appropriate orthoester under refluxing conditions (for other methods of synthesis of benzoxazoles see, S.A. Lang and Y. Lin, *Comprehensive Heterocyclic Chemistry*, Vol. 6, 1–130, Ed. C. W. Rees; and references cited therein). Reduction of 14 with NaBH$_4$ provides the alcohol 15 which is then subjected to pyridinium dichromate (PDC) oxidation to yield the corresponding aldehyde 16. Further elaboration of 16 as outlined provides the key intermediate 17. Similarly, the benzothiazole 19 can also be prepared from the appropriately substituted aminothiophenol 18.

Scheme 4

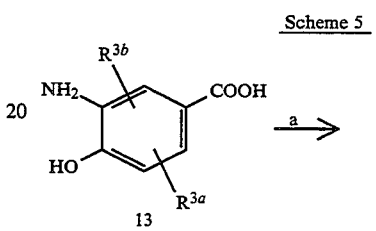

-continued
Scheme 4

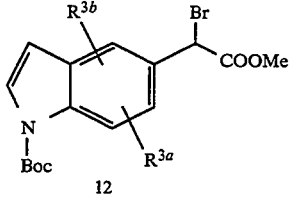

a. (i) DIBALH, Toluene; (ii) Boc$_2$O, DMAP, CH$_2$Cl$_2$
b. (i) CHCl$_3$, KOH, DMF, 0° C.; (ii) NaOH, DME/H$_2$O
c. (i) CH$_2$N$_2$; (ii) CBr$_4$/Ph$_3$P, CH$_2$Cl$_2$ Scheme 5

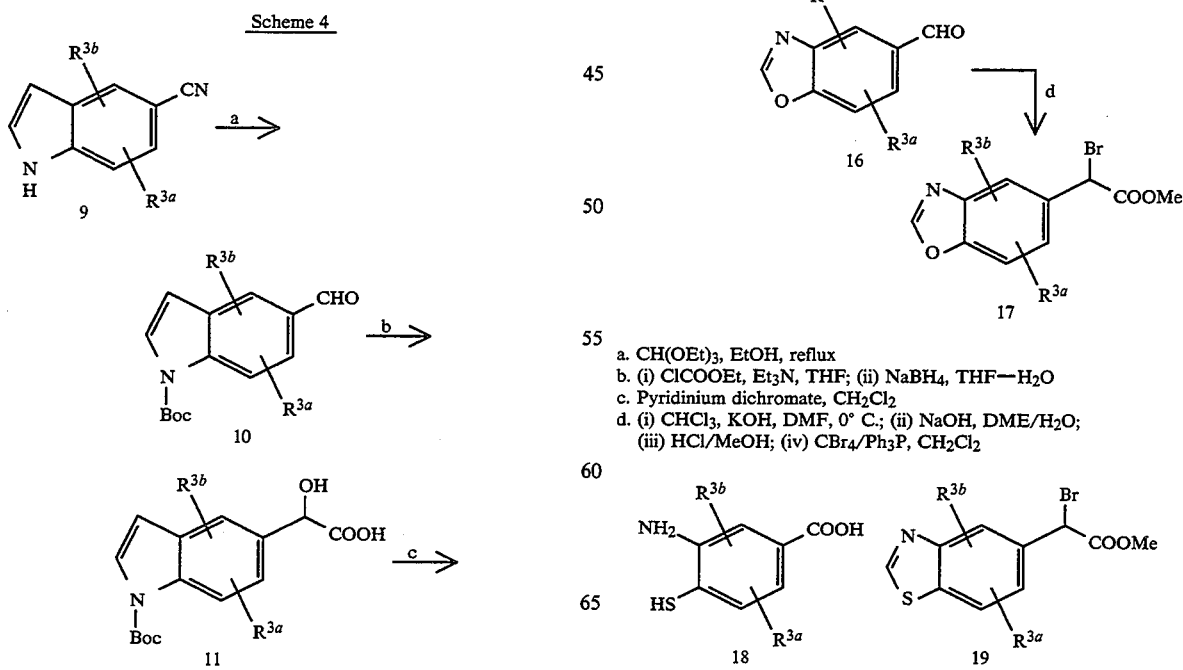

a. CH(OEt)$_3$, EtOH, reflux
b. (i) ClCOOEt, Et$_3$N, THF; (ii) NaBH$_4$, THF—H$_2$O
c. Pyridinium dichromate, CH$_2$Cl$_2$
d. (i) CHCl$_3$, KOH, DMF, 0° C.; (ii) NaOH, DME/H$_2$O;
   (iii) HCl/MeOH; (iv) CBr$_4$/Ph$_3$P, CH$_2$Cl$_2$ Scheme 6 illustrates the synthesis of benzofuran and dihydrobenzofuran alkylating agents 23 and 25. The benzofuran 21 can be prepared from the α-phenoxy carbonyl compound 20 via a ring closure reaction [Stoermer and Wehln, *Chem. Ber.*, 35, 3549 (1902)] (for general methods of synthesis of benzofurans and dihydrobenzofurans see, R.C. Elderfield and V.B. Meyer, *Heterocyclic Compounds*, Vol. 2, Chapter 1, Ed. R.C. Elderfield, Wiley; and references cited therein). The ester 21 is reduced to provide the aldehyde 22 which is then transformed into the corresponding alkylating agent 23. The dihydrobenzofuran ester 24, obtained by catalytic reduction of 21, can also be transformed into the corresponding alkylating agent 25 using the sequence of reactions outlined in Scheme 6.

Benzothiophene 26 may be synthesized from the corresponding aldehyde 26b in a manner similar to that outlined in Scheme 6 for benzofuran 23. Benzothiophene 26b can be prepared by the oxidative cyclization (using an alkaline solution of potassium ferricyanide) of appropriately substituted o-mercaptocinnamic acid 26a [C. Chmelewsky and P. Friedlander, *Chem. Ber.*, 46, 1903 (1913)]. (For general methods of synthesis of benzothiophene, See, E. Champaigne in *Comprehensive Heterocyclic Chemistry*, vol. 4, Chapter 3-15; Eds. A. Katritzky and C.W. Rees.)

Scheme 7 outlines a typical synthesis of α-bromoarylacetates, 30 and 32, bearing appropriately substituted methylenedioxy or 1,4-dioxane rings. The substituted catechol derivative 27 is treated with an appropriate dibromide (where m is 1 or 2) in the presence of cesium carbonate in dimethylformamide to provide 28. Treatment of 28 with DIBALH yields the aldehyde 29 which is then transformed into the desired bromide 30 as described.

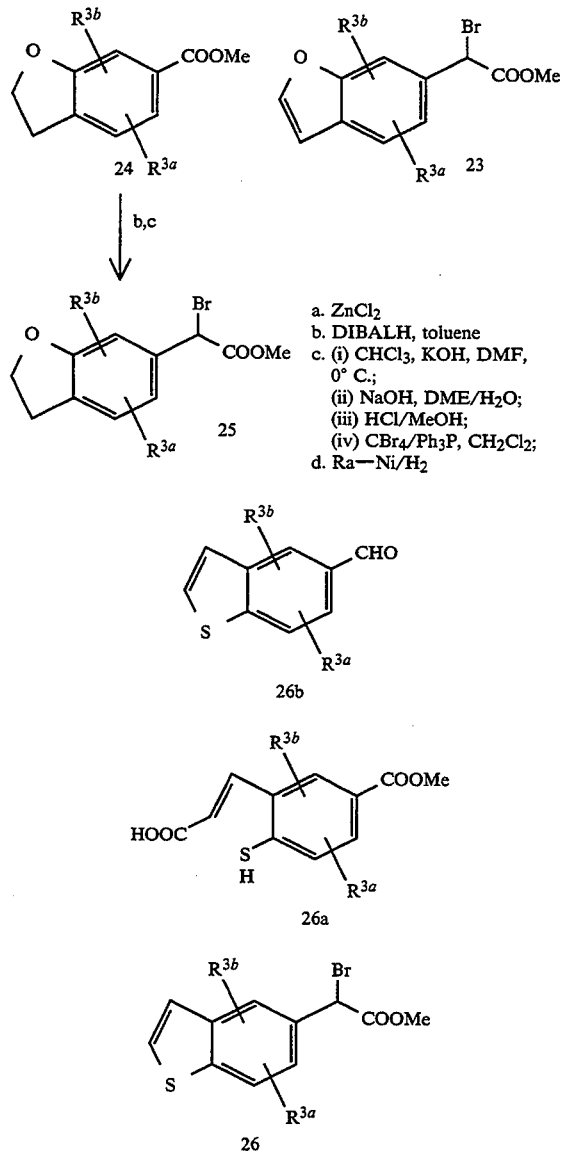

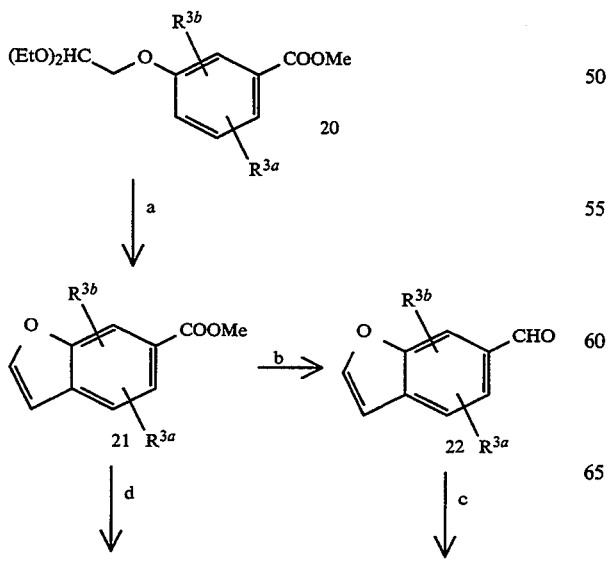

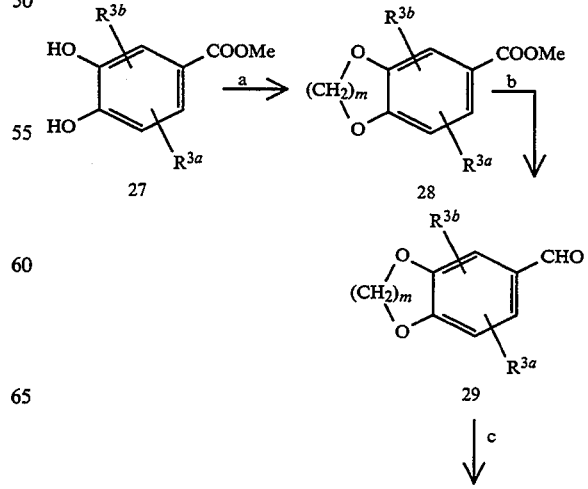

-continued
Scheme 7

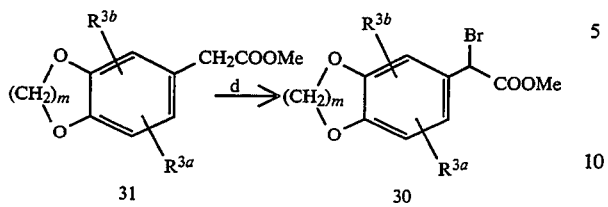

a. Br—(CH$_2$)$_m$—Br, Cs$_2$CO$_3$, DMF
b. DIBALH, toluene
c. (i) CHCl$_3$, KOH, DMF, 0° C.; (ii) NaOH, DME/H$_2$O; (iii) HCl/MeOH; (iv) CBr$_4$/Ph$_3$P, CH$_2$Cl$_2$;
d. NBS, AIBN, CCl$_4$

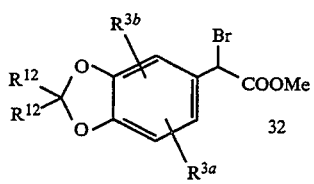

A method of synthesizing the N-benzylated heterocycle 1 is illustrated in Schemes 8. Alkylation of heterocycle 33 with 34 in an appropriate solvent such as an alcohol (methanol, ethanol and the like), DMF, DMSO, THF and acetone in the presence of an alkali metal salt such as alkoxides, carbonates, hydroxides and hydrides, or organic bases such as trialkylamines or alkyl lithiums provides, after a suitable deprotection reaction, compound 1. The P group is an appropriate protecting group such as benzyl or tert-butyldimethylsilyl.

Scheme 8

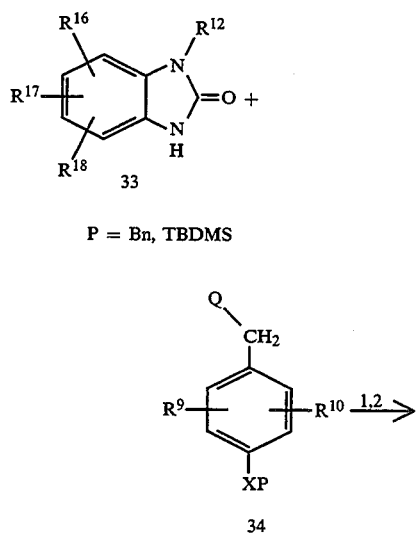

1. Base
2. Deprotection

-continued
Scheme 8

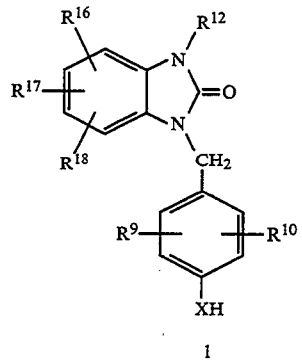

An alternative method of synthesizing compound 1 is outlined in Scheme 9. Reaction of heterocycle 33 with benzyl alcohol 35 in the presence of triphenylphosphine and diethyl azodicarboxylate in an appropriate solvent provides, after an appropriate deprotection reaction, the benzylated heterocycle 1.

Scheme 9

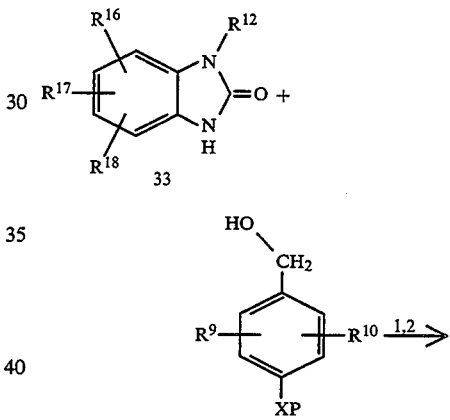

1. PPh$_3$, EtO$_2$CN=NCO$_2$Et
2. Deprotection

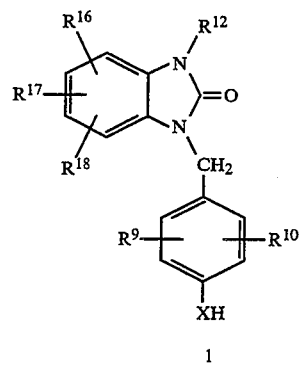

An alternative strategy for synthesizing compounds of formula I is illustrated in Scheme 10. Reaction of heterocycle 33 with alkylating agent 36 in an appropriate solvent such as alcohol (methanol, ethanol and the like), DMF, DMSO, THF and acetone in the presence of an alkali metal salt such as alkoxides, carbonates, hydroxides and hydrides, or organic bases such as trialkylamines or alkyl lithiums provides compound 37. The reactions and techniques for the transformation of the $Z^1$ group to the acidic function Z and also the synthesis of alkylating agent 36 are described in the patent application WO91/11999 (Merck & Co.; published on Aug. 22, 1991 under the Patent Cooperation Treaty) and also U.S. Pat. No. 5,177,095 (Merck & Co.; Jan. 5, 1993).

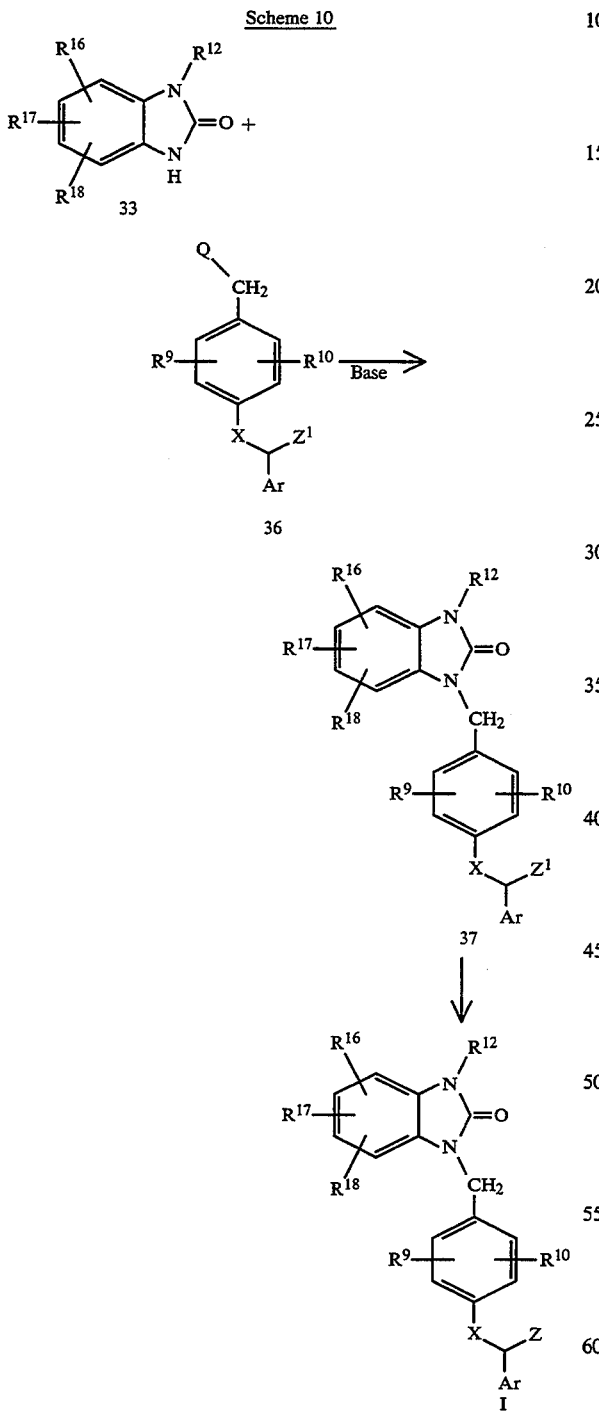

A variety of methods are available for the synthesis of benzimidazolinones 33 (for some general methods of synthesis of benzimidazolinones see, K. Hofmann, "Imidazole and Its Derivatives, Part 1", Interscience, New York, 1953, pp.285-291 ). Scheme 11 illustrates one method of synthesizing benzimidazolinones 33. Nitration of an appropriately substituted carboalkoxyaniline 38 provides compound 39. Reduction provides the α-amino-N-arboalkoxyaniline 40 that upon heating undergoes cyclization to the benzimidazolinone 33 ($R^{12}$=H) [C. Rudolph, Ber., 12, 1295 (1897)]. N-Alkylation of compound 33 ($R^{12}$=H) with the required alkylating agent ($R^{12}$Q) in an appropriate solvent such as THF, DMF or an alcohol (methanol, ethanol and the like) in the presence of an alkali metal salt such as an alkoxide, carbonate, hydroxide or hydride, or organic bases such as alkyl lithiums provides the N-alkylated benzimidazolinone 33.

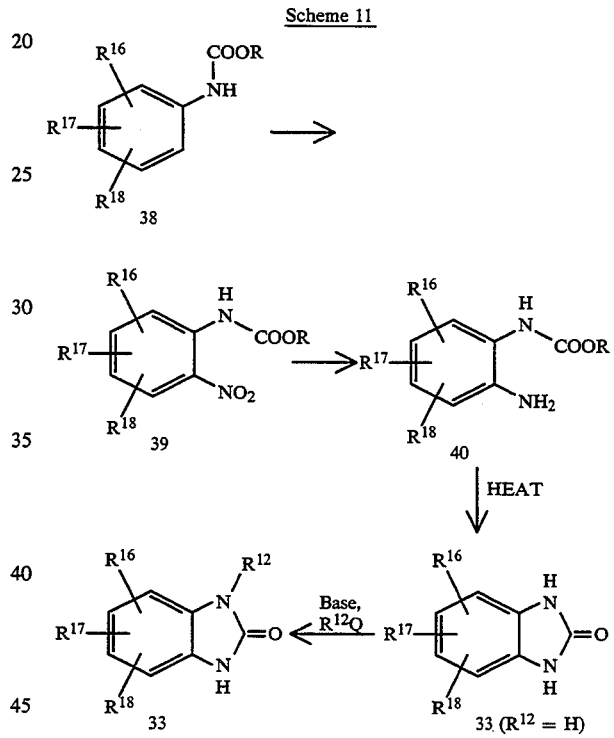

Benzimidazolinones 33 can also be synthesized from the appropriate o-phenylenediamine 41 and phosgene [J.P. English, R. C. Clapp, Q.P. Cole, J. Krapcho, *J. Am. Chem. Soc.*, 67, 2263, (1945); R.L. Clark, A.A. Pessolano, *J. Am. Chem. Soc.*, 80, 1657, (1958)], urea [S.M. Mistry, P.C. Guha, *J. Indian Chem. Soc.*, 7, 793, (1930)], or carbonyl diimidazole [H.A. Staab, *Angew. Chem.*, 68, 754, (1956)] as outlined in Scheme 12.

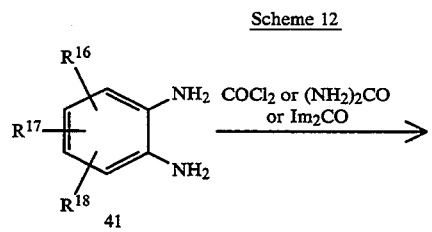

-continued

Scheme 12

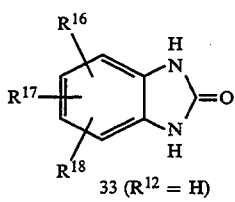

33 (R$^{12}$ = H)

Compounds of general Formula I where X is a methylene group or a substituted methylene group (X=—C(R$^7$)$_2$—) may be prepared according to Scheme 13. A generalized N-substituted benzimidazolinone (41) which bears a leaving group Q on a carbon atom at the 4'-position is used for the alkylation of an anion derived from an active methylene compound 42. In this reaction, the leaving group Q in structure 41 is usually a halide such as chloride, bromide or iodide, or any other suitable leaving group such as mesylate, tosylate or triflate. The active methylene compound (42) employed is a weakly acidic compound. For instance when Z$^1$ is an ester group, then 42 is the ester of a substituted phenylacetic acid. The ester enolate of a phenylacetic ester (42) is prepared at low temperature in an anhydrous aprotic solvent such as THF, dioxane or the like, using a strong base such as an alkali metal hydride, an alkali metal salt of an alcohol, or preferably an alkali metal salt of a dialkylamine such as lithium diisopropylamide. After addition of the benzimidazolinone 41 to the enolate derived from 42, the compound 43 is the product.

The last stage in the preparation of compounds of general Formula I where X is a methylene group or a substituted methylene group, is the conversion of the precursor group Z$^1$ to the desired group Z. For instance when Z$^1$ is an ester group, then hydrolysis with sodium or potassium hydroxide in a suitable solvent such as methanol or ethanol provides a compound of general Formula I wherein X=—C(R$^7$)$_2$—, and Z is a carboxylic acid.

The carboxylic acids of general Formula I (Z=CO$_2$H) are useful intermediates for the preparation of other compounds of general Formula I which are within the scope of this invention. Thus, a compound of general Formula I where Z=—CONH—(tetrazol-5-yl) may be prepared by reaction of such a carboxylic acid with 1,1'-carbonyldiimidazole in DMF followed by addition of 5-aminotetrazole. Similarly, reaction of these carboxylic acids with 1,1'-carbonyldiimidazole in DMF followed by addition of either an alkylsulfonamide, a phenylsulfonamide or a heteroarylsulfonamide provides compounds of general Formula I having Z=—CONHSO$_2$—(C$_1$-C$_8$)-alkyl, Z=—CONHSO$_2$-phenyl, or Z=—CONHSO$_2$—heteroaryl where the alkyl, phenyl or heteroaryl groups may be substituted as previously defined.

The group Z$^1$ may also be converted to other appropriate functional groups as defined for Z using standard synthetic transformations known to those skilled in organic synthesis. For example, Z$^1$ may be converted to a primary amide using ammonia in a suitable solvent at elevated temperature to give 43 (Z$^1$=—CONH$_2$). Dehydration of such an amide may be accomplished under mild conditions using trichloroacetyl chloride and triethylamine (see: Saednya, A. Synthesis, 1985, 184) to provide a nitrile (43, Z$^1$=—CN). Then the nitrile may be converted to a compound of general Formula I where Z is a tetrazole group using trimethyltin azide in toluene at elevated temperature.

The alkylation reaction of an enolate derived from an active methylene compound 42 and the generalized N-substituted benzimidazolinone (41) bearing a leaving group Q which is shown in Scheme 13 may also be conducted when Z$^1$ is an acylsulfonamide group such as 42 where Z$^1$=—CONHSO$_2$—R or Z$^1$=—SO$_2$NH-CO—R and R is either an alkyl, phenyl or heteroaryl group as previously defined. In these cases, compound 42 is deprotonated with two equivalents of a strong base to provide a dianionic intermediate. One equivalent of the base removes the more acidic hydrogen from the acyl sulfonamide group first, then the second equivalent of base deprotonates the more weakly acidic active methylene group to form dianion. These reactions are performed in an anhydrous aprotic solvent such as THF, dioxane or DMSO usually at low temperature and using a strong base such as a lithium, sodium or potassium dialkylamide. Alternatively, one can employ one equivalent of a weaker base such as an alkali metal hydride or alkoxide to deprotonate the acylsulfonamide group, then add a second equivalent of a strong base to form the dianion. Dianionic intermediates derived from compounds of formula 42 are then reacted with the generalized N-substituted benzimidazolinone (41) bearing the leaving group Q. These alkylation reactions occur at the anionic site derived from the weakly acidic active methylene group and provide compounds of general Formula I directly where Z=—CONHSO$_2$—R or Z=—SO$_2$NHCO—R and R is either an alkyl, phenyl or heteroaryl group as previously defined.

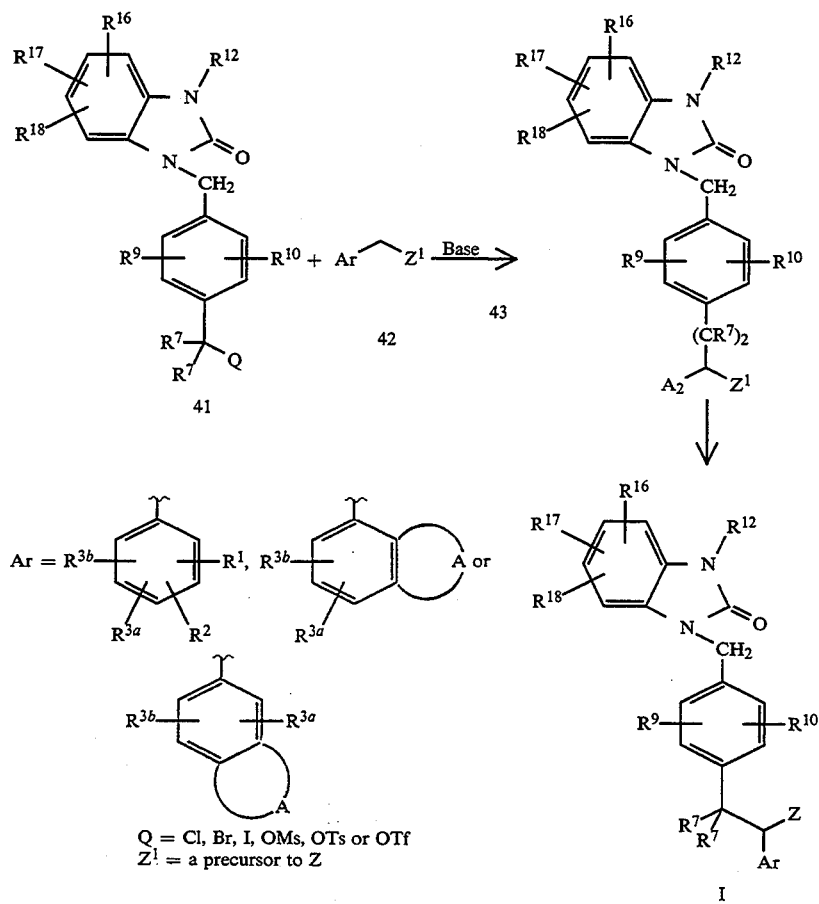

-continued
Scheme 14

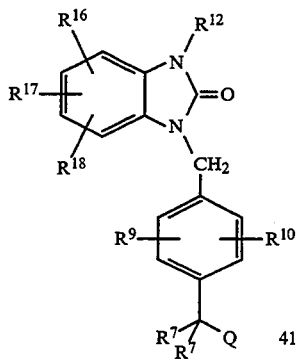

P = Protecting group
Q = Leaving group

One method for preparation of the substituted benzimidazolinone 41 which is employed in the alkylation reaction shown in Scheme 13 is illustrated in Scheme 14. The generalized benzimidazolinone 33 is treated with a base such as an alkali metal hydride in a polar aprotic solvent like DMF, and after deprotonation 33 is reacted with the substituted benzyl compound 44 followed by deprotection of the alcohol protecting group. The product of the two-step reaction is the benzyl-substituted benzimidazolinone 45. Again, in compounds of formula 44 the group Q is any suitable leaving group such as a halide, mesylate, or tosylate as previously described, and the substitutent P represents an alcohol protecting group such as a silyl ether or the like. Compounds of general formula 41 are then prepared from the benzyl alcohols 45 by standard methodology. For instance, benzyl alcohols like 45 are readily transformed to substituted benzyl bromides 41 (Q=Br) or chlorides 41 (Q=Cl) using the appropriate phosphorus trihalide. Alternatively, the bromides 41 (Q=Br) are prepared from alcohols 45 using triphenylphosphine and carbon tetrabromide in a solvent such as methylene chloride.

Compounds of general formula 44 shown in Scheme 14 may be prepared in a variety of ways, and the method of preparation which is preferred is based upon consideration of which substituents ($R^7$, $R^9$, and $R^{10}$) are desired in the novel compounds of general Formula I disclosed in this invention. Readily available starting materials for the preparation of compounds of general formula 44 are chosen based upon the desired substituents ($R^7$, $R^9$, and $R^{10}$), and then the synthetic route for converting the starting materials to compounds of formula 44 is devised using synthetic analysis familiar to those skilled in organic synthesis. For instance, numerous substituted 4-hydroxybenzoic acids of general formula 46 (Scheme 15) are commercially available or are described in the chemical literature and can serve as starting materials for the synthesis of compounds of general formula 46 as shown in Scheme 15. Furthermore, the synthesis of a number of compounds of general formula 46 are described in patent application WO 91/11999 (Merck & Co.; Aug. 22, 1991) and also in U.S. Pat. No. 5,177,095 (Merck & Co.; Jan. 5, 1993).

Scheme 15

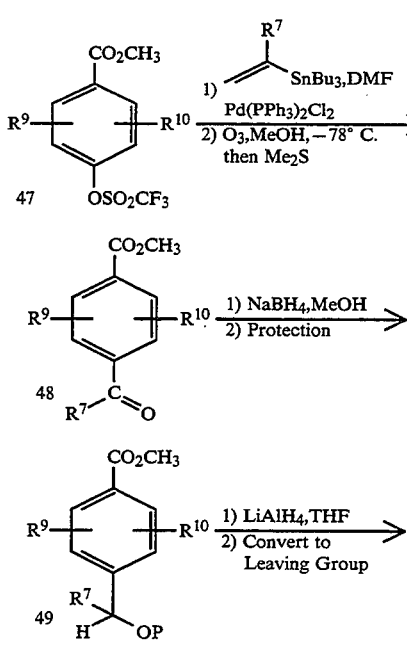

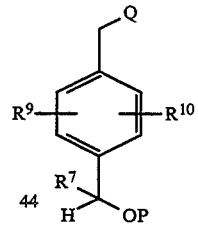

Scheme 15 illustrates a preferred synthetic route for conversion of compounds of general formula 46 to compounds of general formula 44. A substituted 4-hydroxybenzoic acid 46 is first esterified with a lower alkanol such as methanol in the presence of an acid catalyst. The intermediate ester is then deprotonated with a suitable base and then converted to the phenol triflate 47 using either trifluoromethanesulfonic anhydride or N-phenyltrifluoromethanesulfonimide.

The aryl triflate 47 is next converted to a carbonyl compound 48. A two-step method for this transformation that is shown in Scheme 15 involves initial palladium catalyzed cross-coupling of the aryl triflate 47 with a vinyltributylstannane followed by ozonolysis of the resulting olefin. The palladium catalyzed cross coupling reactions of aryl triflates and vinylstannanes (see: Echavarren, A.M.; Stille, J.K. *J. Amer. Chem. Soc.* 1987, 109, 5478) are generally conducted in aprotic solvents such as THF, dioxane, DMF, or the like, and in the presence of a suitable palladium catalyst such as tetrakis(triphenylphosphine)palladium(0) or bis(triphenylphosphine)palladium(II) chloride. The ozonolysis of the intermediate olefin is conducted at low temperature in solvents like methanol or methylene chloride and then worked up in the presence of methylsulfide to provide a carbonyl compound. If the vinylstannane used in the above palladium catalyzed cross-coupling is vinyltributyltin, then after the ozonolysis reaction a benzaldehyde (48 $R^7$=H) derivative is the product. If however, the $R^7$ group in the starting stannane is an alkyl group, then after the ozonolysis reaction an arylketone (48 $R^7$=alkyl) is the product.

The last stages in the preparation of compounds of general formula 44 is reduction of the carbonyl group of 48 under standard conditions with a reducing agent such as sodium borohydride, followed by protection of the resulting alcohol with any commonly used protecting group for alcohols which is unreactive towards strong reducing agents. Reduction of the ester group of the protected alcohol 49 is then accomplished with a reagent such as lithium aluminumhydride or lithium borohydride in an ethereal solvent like THF or dioxane, and finally the resulting benzyl alcohol is converted under standard conditions to any useful leaving group (halide, mesylate, tosylate etc.) to afford a compound of general formula 44.

The reactions are performed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending upon the reactions and techniques employed, optimal yields may require changing the order of synthetic steps or use of protecting groups followed by deprotection.

The salts of the compounds of formula I are useful in the novel method of treatment of this invention. The salts of the compounds of formula I are formed with various inorganic and organic acids and bases are also considered to be within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methanesulfonic, toluenesulfonic, maleic, fumaric, camphorsulfonic.

The salts can be formed by conventional means, such as by reacting the free acid or free base forms of the compounds of general formula I with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

It will be appreciated that the compounds of general Formula I in this invention may be derivatised at functional groups to provide prodrug derivatives which are capable of conversion back to the parent compounds in vivo. The concept of prodrug administration has been extensively reviewed (e.g.A.A. Sinkula in *Annual Reports in Medicinal Chemistry*, Vol 10, R.V. Heinzelman, Ed., Academic Press, New York London, 1975, Ch. 31, pp. 306–326, H. Ferres, *Drugs of Today*, Vol 19, 499–538 (1983) and *J. Med. Chem.*, 18, 172 (1975)). Examples of such prodrugs include the physiologically acceptable and metabolically labile ester derivatives, such as lower alkyl (e.g. methyl or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminoethyl esters (e.g. 2-dimethylaminoethyl esters). Additionally, any physiologically acceptable equivalents of the compounds of general Formula I, similar to the metabolically labile esters, which are capable of producing the parent compounds of general Formula I in vivo, are within the scope of this invention.

It will be further appreciated that the majority of compounds of general Formula I claimed herein are asymmetric and are produced as racemic mixtures of enantiomers and that both the racemic compounds and the resolved individual enantiomers are considered to be in the scope of this invention. The racemic compounds of this invention may be resolved to provide individual enantiomers utilizing methods known to those skilled in the art of organic synthesis. For example, diastereoisomeric salts, esters or imides may be obtained from a racemic compound of general Formula I and a suitable optically active amine, amino acid, alcohol or the like. The diastereoisomeric salts, esters or imides are separated and purified, the optically active enantiomers are regenerated and the preferred enantiomer is the more potent isomer. The resolved enantiomers of the compounds of general Formula I, their pharmaceutically acceptable salts and their prodrug forms are also included within the scope of this invention.

Endothelin (ET-1), and two closely related bioactive peptides, ET-2 and ET-3, are widely distributed in mammalian tissues, and they can induce numerous biological responses in non-vascular as well as vascular tissues by binding to at least two distinct endothelin receptor subtypes. In addition to cardiovascular smooth muscle, neural and atrial sites, endothelin receptors may also be found in gastrointestinal, kidney, lung, urogenital, uteral and placental tissues.

Endothelin is a potent vasoconstrictor peptide and thus plays a role in vivo in arterial pressure-volume homeostasis. Not only peripheral, but coronary vascular resistance as well, is increased by endothelin; cardiac output is decreased, while plasma renin activity is increased. Them is a reduction in renal blood flow and glomemlar filtration rate, while levels of atrial natriuretic factor, vasopressin, and aldosterone become elevated.

It is also considered, in accordance with the present invention, that antagonists for the endothelin receptor may be useful in preventing or reducing restenosis subsequent to denudation following angioplasty. Such denudation results in myointimal thickening following angioplasty, due to increased endothelin release. Endothelin acts as a growth factor with respect to smooth muscle and fibroblastic cells, and possibly other types of cells, as well.

Endothelin is also a neuropeptide, acting on the posterior pituitary, where it modulates the release of the neurosecretory honnones vasopressin and oxytocin. Endothelin released from the posterior pituitary also acts as a circulating hormone, having a wide range of actions as discussed further above. This includes effects on the endocrine system, especially the adrenal glands. Endothelin increases plasma levels of epinephrine.

Consequently, the novel compounds of the present invention, which are receptor antagonists of endothelin, have therapeutic usefulness in preventing, decreasing or modulating the various physiological effects of endothelin discussed above, by wholly or partially blocking access of endothelin to its receptor.

Endothelin Receptor Binding Assays

The binding of the novel compounds of this invention to the endothelin receptor was determined in accordance with the assay described in detail immediately below. It is similar to the assay described in Ambar et al. (1989) *Biochem. Biophys. Res. Commun.* 158, 195–201; and Khoog et al. (1989) FEBS Letters, 253, 199–202.

The endothelins (ETs) have a number of potent effects on a variety of cells, and exert their action by interacting with specific receptors present on cell membranes. The compounds described in the present invention act as antagonists of ET at the receptors. In order to identify ET antagonists and determine their efficacy in vitro, the following three ligand receptor assays were established.

Receptor binding assay using cow aorta membrane preparation

Thoracic aortae were obtained from freshly slaughtered calves and brought to the lab on wet ice. The adventitia were removed, and the aorta was opened up lengthwise. The lumenal surface of the tissue was scrubbed with cheesecloth to remove the endothelial layer. The tissue was ground in a meat grinder, and suspended in ice-cold 0.25 M sucrose, 5 mM tris-HCl, pH 7.4, containing 0.5 mg/mL leupeptin and 7 mg/mL pepstatin A. Tissue was homogenized twice and then centrifuged for 10 minutes at 750 $\times$g at 4° C. The supernatant was filtered through cheesecloth and centrifuged again for 30 minutes at 48,000 $\times$g at 4° C. The pellet thus obtained was resuspended in the buffer solution described above (including the protease inhibitors), and aliquots were quick-frozen and stored at $-70$° C. until use. Membranes were diluted into 50 mM KPi, 5 mM EDTA pH 7.5 containing 0.01% human serum albumin. Assays were done in triplicate. Test compounds and 100 pM [1251]-endothelin-1 (2000-2200 Ci/mmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}$I radioactivity in a gamma counter. Nondisplaceable binding of [$^{125}$I]-endothelin-1 is measured in the presence of 100 nM unlabelled endothelin- 1 [Endothelin-1 (ET-1 ) was purchased from Peptides International (Louisville, KY). $^{125}$I-ET-1 (2000 Ci/mMol) was purchased from Amersham (Arlington Heights, IL)]. Specific binding is total binding minus nondisplaceable binding. The inhibitory concentration (IC$_{50}$) which gives 50% displacement of the total specifically bound [$^{125}$I]-endothelin-1 was presented as a measure of the efficacy of such compounds as ET antagonists.

Receptor binding assay using rat hippocampal membrane preparation

Rat hippocampi were obtained from freshly sacrificed male Sprague-Dawley rats and placed in ice cold 0.25 M sucrose, 5 mM tris-HCl, pH 7.4 containing 0.5 mg/mL leupeptin, 7 mg/mL pepstatin A. Hippocampi were weighed and placed in a Dounce homogenizer with 25 volumes (wet weight to volume) ice-cold sucrose buffer in the presence of protease inhibitors. Hippocampi were homogenized using a Dounce (glass-glass) homogenizer with type A pestle, with homogenizer in ice. Tissue homogenate was centrifuged at 750 $\times$g for 10 min at 4° C. Supernatant was filtered through dampened cheesecloth, and centrifuged again at 48,000 $\times$g for 30 min at 4° C. Pellets were resuspended in sucrose buffer with protease inhibitors. Aliquots of this preparation were quick frozen and stored at $-70$° C. until use. Membranes were diluted into 50 mM KPi, 5 mM EDTA pH 7.5 containing 0.01% human serum albumin. Assays were done in triplicate. Test compounds and 25 pM [$^{125}$I]-endothelin-1 (2000-2200 Ci/mmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}$I radioactivity in a gamma counter. Nondisplaceable binding of [$^{125}$I]-endothelin-1 is measured in the presence of 100 nM unlabelled endothelin-1 [Endothelin-1 (ET-1) was purchased from Peptides International (Louisville, KY). $^{125}$I-ET-1 (2000 Ci/mMol) was purchased from Amersham (Arlington Heights, IL)]. Specific binding is total binding minus nondisplaceable binding. The inhibitory concentration (IC$_{50}$) which gives 50% displacement of the total specifically bound [$^{125}$I]-endothelin-1 was presented as a measure of the efficacy of such compounds as endothelin antagonists.

Receptor binding assay using cloned human ET receptors expressed in Chinese Hamster Ovary Cells Both endothelin receptor subtypes were cloned from a human cDNA library and were individually expressed in Chinese Hamster Ovary cells. Cells were harvested by addition of 126 mM NaCl, 5 mM KCl, 2 mM EDTA, 1 mM NaH$_2$PO$_4$, 15 mM glucose, 10 mM tris/HEPES pH 7.4 Cells were centrifuged at 250 $\times$g for 5 minutes. The supernatant was aspirated off, and the cells were resuspended in the 50 mM KPi, 5 mM EDTA pH 7.5 containing 0.01% human serum albumin. Assays were done in triplicate. Test compounds and 25–100 pM[$^{125}$I]-endothelin-1 (2000-2200 Ci/mmole, obtained from New England Nuclear or Amersham) were placed in a tube containing 50 mM KPi, 5 mM EDTA pH 7.5 containing 0.01% human serum albumin, and the cells prepared above were added last. The samples were incubated for 60 min at 37° C. At the end of this incubation, samples were filtered onto prewetted (with 2% BSA in water) glass fiber filter pads and washed with 150 mM NaCl, 0.1% BSA.

The filters were assayed for $^{125}$I radioactivity in a gamma counter. Nondisplaceable binding of [$^{125}$I]-endothelin-1 is measured in the presence of 100 nM unlabelled endothelin-1 [Endothelin-1 (ET-1) was purchased from Peptides International (Louisville, KY). $^{125}$I-ET-1 (2000 Ci/mMol) was purchased from Amersham (Arlington Heights, IL)]. Specific binding is total binding minus nondisplaceable binding. The inhibitory concentration (IC$_{50}$) which gives 50% displacement of the total specifically bound [$^{125}$I]-endothelin-1 was presented as a measure of the efficacy of such compounds as endothelin antagonists.

The binding assays described above were used to evaluate the potency of interaction of representative compounds of the invention with endothelin receptors. To determine whether these compounds were endothelin antagonists, assays which measure the ability of the compounds to inhibit endothelin-stimulated phosphatidylinositol hydrolysis were established. Rat uterus contains predominantly one of the known endothelin receptor subtypes ($ET_A$).

Phosphatidylinositol hydrolysis assays using rat uterine slices

Diethylstilbestrol primed female Sprague-Dawley rats were sacrificed and their uteri were collected, dissected of fat and connective tissue and minced. Minced tissue was added to oxygenated (95% $O_2$, 5% $CO_2$) 127 mM NaCl, 25 mM $NaHCO_3$, 10 mM Glucose, 2.5 mM KCl, 1.2 mM $KH_2PO_4$, 1.2 mM $MgSO_4$, 1.8 mM $CaCl_2$. To the tissue mince, 1.2 mM myo-[$^3$H]-inositol (Amersham) was added. The mince was incubated 90 min at 37° C., with constant oxygenation. After incubation, the loaded tissue mince was washed five times with the same oxygenated buffer to remove excess radiolabelled inositol. The tissue mince was resuspended in the above buffer, containing 10 mM LiCl, aliquotted into tubes, and 3 nM endothelin-1 with and without test compounds was added to start the assay. Assays were done in quadruplicate. Samples were incubated at 37° C. under blowing $O_2$ in a hooded water bath for 30 minutes. Reaction was stopped by addition of trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 mL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolunm sample. Control values (100% stimulated) are values in the presence of endothelin minus the values in the absence of endothelin (basal). Test sample values are the values in the presence of endothelin and test sample minus basal. Inhibitory concentration ($IC_{50}$) is the concentration of test compound required to give a sample activity of 50% of control value.

Sarafotoxin S6c is a member of the endothelin family which binds preferentially to one of the known endothelin receptor subtypes ($ET_B$).

Phosphatidylinositol hydrolysis assays using rat lung slices

Male Sprague-Dawley rats were sacrificed and their lungs were collected, dissected of fat and connective tissue and minced. Minced tissue was added to oxygenated (95% $O_2$, 5% $CO_2$) 127 mM NaCl, 25 mM $NaHCO_3$, 10 mM glucose, 2.5 mM KCl, 1.2 mM $KH_2PO_4$, 1.2 mM $MgSO_4$, 1.8 mM $CaCl_2$. To the tissue mince, 1.2 μM myo-[$^3$H]-inositol was added. The mince was incubated 60 min at 37° C., with constant oxygenation. After incubation, loaded tissue mince was washed five times with the same oxygenated buffer to remove excess radiolabelled inositol. Tissue mince was resuspended in the above buffer, containing 10 mM LiCl, aliquotted into tubes, and 3 nM sarafotoxin S6c with and without test compounds was added to start the assay. Assays were done in quadruplicate. Samples were incubated at 37° C. under blowing $O_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 mL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of sarafotoxin minus the values in the absence of sarafotoxin (basal). Test sample values are the values in the presence of sarafotoxin and test sample minus basal. Inhibitory concentration ($IC_{50}$) is the concentration of test compound required to give a sample activity of 50% of control value.

Phosphatidylinositol hydrolysis assays using cloned human endothelin receptors expressed in Chinese Hamster Ovary cells Endothelin receptors of both receptor subtypes were cloned from a human cDNA library and were individually expressed in Chinese Hamster Ovary cells. Cells were loaded overnight by the addition of 1.2 μM myo-[$^3$H]-inositol to their growth medium. Cells were harvested by addition of 126 mM NaCl, 5 mM KCl, 2 mM EDTA, 1 mM $NaH_2PO_4$, 15 mM glucose, 10 mM tris-/HEPES pH 7.4. Cells were washed five times by centrifugation at 250 ×g for 5 minutes to remove excess radiolabelled inositol. The supernatant was aspirated off, and the cells were resuspended in the same oxygenated (95% $O_2$, 5% $CO_2$) buffer containing 10 mM LiCl, aliquotted into tubes, and 0.3 nM endothelin-1 with and without test compounds was added to start the assay. Assays were done in quadruplicate. Samples were incubated at 37° C. under blowing $O_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 mL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration ($IC_{50}$) is the concentration of test compound required to give a sample activity of 50% of control value.

Using the methodology described above, representative compounds of the invention were evaluated and found to exhibit IC$_{50}$ values of at least <50 μM thereby demonstrating and continuing the utility of the compounds of the invention as effective endothelin antagonists.

Accordingly the novel compounds of the present invention are useful in human therapy for treating asthma, hypertension, renal failure particularly post-ischemic renal failure, cyclosporin nephrotoxicity, vasospasm, cerebral and cardiac ischemia, myocardial infarction, or endotoxic shock caused by or associated with endothelin, by administration to a patient in need of such treatment of a therapeutically effective amount thereof.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 0.5 mg to 1.0 g per patient per day which can be administered in single or multiple doses. Preferably, the dosage range will be about 0.5 mg to 500 mg per patient per day; more preferably about 0.5 mg to 200 mg per patient per day.

The present invention also relates to pharmaceutical compositions for treating asthma, hypertension, renal failure, particularly post-ischemic renal failure, the vascular consequences of diabetes such as glaucoma and neuropathy, cyclosporin nephrotoxicity, vasospasm, cerebral and cardiac ischemia, myocardial infarction, or endotoxin shock caused by or associated with endothelin, comprising a therapeutically effective amount of the novel compound of this invention together with a pharmaceutically acceptable carrier therefor.

About 0.5 mg to 1.0 g of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of Formula I and their incorporation into pharmaceutical compositions and as such are not to be considered as limiting the invention set forth in the claims appended hereto.

EXAMPLE 1

1-[4-(1-Carboxy-1-(3-methylphenyl)methoxy)-3,5-dipropylphenylmethyl]-2-benzimidazolinone Step A: Preparation of ethyl α-bromo-3'-methylphenylacetate.

To a magnetically stirred solution of 7.20 g (37.1 mmol) of ethyl 3'-methylmandelate and 18.5 g (55.7 mmol) of carbon tetrabromide in 30 mL of methylene chloride was added 14.6 g (55.7 mmol) of triphenylphosphine in portions at 0° C. The reaction mixture was stirred and allowed to slowly warm to room temperature over two hours. The reaction mixture was then evaporated in vacuo and adsorbed onto a silica gel flash chromatography column which was then eluted with 5% EtOAc-hexane. Evaporation of the purified fractions and drying in vacuo afforded 6.90 g (72%) of the title compound.

$^1$H NMR (200 MHz, CDCl$_3$, ppm): δ1.27 (t, J=7.0 Hz, 3H), 2.35 (s, 3H), 4.10–4.32 (m, 2H), 5.31 (s, 1H), 7.12–7.38 (m, 4H).

FAB-MS: m/e 258 (M+H).

Step B: Preparation of ethyl 2-(2,6-dipropyl-4-hydroxymethyl phenoxy)-2-(3-methylphenyl)acetate.

To a solution of 2.44 g (11.7 mmol) of 2,6-di-propyl-4-hydroxymethylphenol in 10 mL of DMF was added 4.76 g (14.6 mmol) of cesium carbonate, a solution of 3.00 g (11.7 mmol) of the product of Step A dissolved in 10 mL of DMF, and the reaction mixture was stirred and heated at 60° C. overnight. The reaction was then cooled to room temperature and partitioned between EtOAc and water. The organic layer was separated, washed with saturated brine, dried (MgSO$_4$), filtered and evaporated in vacuo. The residue was purified on a silica gel flash chromatography column eluted with 20% EtOAc-hexane. Evaporation of the purified fractions and drying in vacuo afforded 2.93 g (65%) of the title compound.

$^1$H NMR (300 MHz, CDCl$_3$, ppm): δ0.79 (t, J=7.20 Hz, 6H), 1.21 (t, J=7.20 Hz, 3H), 1.40–1.52 (m, 4H), 2.30–2.38 (m, 4H), 2.35 (s, 3H), 2.55 (t, J=5.20 Hz, 1H), 4.10–4.28 (m, 2H), 4.56 (d, J=5.20 Hz, 2H), 5.02 (s, 1H), 6.97 (s, 2H), 7.14–7.16 (m, 1H), 7.21–7.26 (m, 2H), 7.33 (s, 1H).

Step C: Preparation of ethyl 2-(2,6-dipropyl-4-bromomethylphenoxy)-2-(3-methylphenyl)acetate To a solution of 2.03 g (5.29 mmol) of the product of Step B dissolved in 10 mL of carbon tetrachloride was added 0.50 mL (5.29 mmol) of phosphorous tribromide and the reaction mixture was magnetically stirred at room temperature for 1 hour as hydrogen bromide was evolved. The magnetic stir bar was removed, and the reaction mixture was concentrated in vacuo. The residue was redissolved and evaporated from methylene chloride three times to remove most of the hydrogen bromide. Finally, the residue was purified by rapid flash chromatography on a silica gel column eluted with 20% EtOAc-hexane. Combination and evaporation of the purified fractions in vacuo afforded 2.27 (96%) of the title compound.

$^1$H NMR (300 MHz, CDCl$_3$, ppm): δ0.79 (t, J=7.20 Hz, 6H), 1.21 (t, J=7.20 Hz, 3H), 1.38–1.52 (m, 4H), 2.25–2.38 (m, 4H), 2.33 (s, 3H), 4.10–4.28 (m, 2H), 4.41 (s, 2H), 5.03 (s, 1H), 6.99 (s, 2H), 7.14–7.17 (m, 1H), 7.22–7.28 (m, 2H), 7.32 (s, 1H).

Step D: Preparation of 1-[4-(1-carboethoxy-1-(3-methylphenyl)methoxy)-3,5-dipropylphenylmethyl]-2-benzimidazolinone To a suspension of 4 mg (0.17 mmol) of sodium hydride in 1.0 mL of DMF was added 75 mg (0.17 mmol) of (3H)-benzimidazolone and the reaction mixture was stirred for 20 minutes. 75 mg (0.17 mmol) of 4-(1-carbomethoxy-1-(3-methylphenyl)methoxy)-3,5-dipropylbenzylbromide in 1.0 mL of DMF was added and the reaction mixture was stirred at room is temperature overnight. The reaction mixture was poured into ethyl acetate and washed with water and then brine. The organic layer was dried over sodium sulfate, decanted and concentrated. Purification by flash chromatography (silica gel, hexane/ethyl acetate 2:1) provided 41 mg of a dialkylated compound and 16 mg (0.03 mmol) of the title compound.

Step E: Preparation of 1-[4-(1-carboxy-1-(3-methylphenyl)methoxy)-3,5-dipropylphenylmethyl]-2-benzimidazolinone To a solution of 16 mg (0.03 mmol) of the title compound from Step D in 1.0 mL of methanol was added 6 drops of 1 N KOH. When TLC analysis showed that the starting material had been consumed the reaction mixture was acidified with 1 N HCl and then concentrated. Purification by flash chromatography (silica gel, chloroform / methanol / ammonium hydroxide 90:10:1) gave 10 mg(0.021 mmol) of the title compound.

$^1$H NMR (400 MHz, CD$_3$OD): δ7.27–6.95 (m, 8H), 6.92 (s, 2H), 4.95 (s, 2H), 4.81 (s, 2H), 2.31–2.28 (m, 4H), 1.45-1.31 (m, 4H), 0.74 (t, J=7.28 Hz, 6H). FAB MS; m/e 473 (m+1).

EXAMPLE 2
1-[4-(1-Carboxy-1-(3,4-methylenedioxyphenyl)methoxy)phenylmethyl]-3-methyl-2-benzimidazolinone

Step A: Preparation of methyl 2-bromo-2-(3,4-methylenedioxyphenyl)acetate

A mixture of (3,4-methylenedioxyphenyl)acetic acid (4.64 g, 25.74 mmol) in dry DMF (40 mL), cesium carbonate (9.2 g, 25.74 mmol) and methyl iodide (3.7 g, 26.0 mmol) in dry DMF (40 mL) was stirred at room temperature for 3h. At the end of this period, the reaction mixture was poured into ice water and extracted with ethyl acetate. The organic phase was washed with saturated NaHCO$_3$, water, brine and then dried (MgSO$_4$) and filtered. The filtrate was concentrated in vacuo to provide pure methyl (3,4-methylenedioxyphenyl)acetate as an oil (4.38 g).

N-Bromosuccinimide (3.95 g, 22.2 mmol) and AlBN (0.098 g, 0.06 mMol) were added to a solution of methyl (3,4-methylenedioxyphenyl)acetate (3.9 g, 21.2 mmol) in carbon tetrachloride and the mixture was refluxed for 2.5 h. The reaction was cooled and filtered. The flitrate was concentrated in vacuo and the residue obtained was purified by flash chromatography on silica-gel using 10% ethyl acetate-hexane. Yield 2.6 g (oil).

$^1$H-NMR (400 MHz, CDCl$_3$, ppm): δ7.105 (d, 1H), 6.93 (d, 1H), 6.72 (m, 1H), 5.964 (s, 2H), 5.28 (s, 1H), 3.76 (s, 3H).

Step B: Preparation of 4-(1-carbomethoxy-1-(3,4-methylenedioxyphenyl)methoxy)-3,5-dipropylbenzyl alcohol To a solution of (3,5-dipropyl-4-hydroxy)benzyl alcohol (0.19 g, 1.0 mmol) in dry DMF (4 mL) were added cesium carbonate (0.33g, 1.01 mmol) and methyl 2-bromo-2-(3,4-methylenedioxyphenyl)acetate (0.272 g, 1.0 mmol) and the mixture was stirred at room temperature for 3h. At the end of this period, the reaction mixture was poured into ice water and extracted with ethyl acetate. The organic phase was washed with water, brine, dried (MgSO$_4$) and then filtered. The flitrate was concentrated in vacuo to provide an oil, which was then purified by flash chromatography on silica-gel using ethyl acetate-hexane (1:4) to provide the titled product as a thick colorless oil (0.30 g).

$^1$H-NMR (200 MHz, CDCl$_3$, ppm): δ7.05 (s, 1H), 6.97 (s, 2H), 6.88 (d, 1H), 6.75 (d, 1H), 5.97 (s, 2H), 5.00 (s, 1H), 4.55 (s, 2H), 3.74 (s, 3H), 2.38 (m, 4H), 1.45 (m, 4H), 0.82 (t, 6H).

Step C: Preparation of 4-(1-carbomethoxy-1-(3,4-methylenedioxyphenyl)methoxy)-3,5-dipropylbenzylbromide To a solution of the product of Step B (0.53 g, 1.38 mmol) in dry THF (10 mL) were added Ph$_3$P (0.49 g, 2.06 mmol), CBr$_4$ (0.69 g, 2.06 mmol) and CH$_3$CN (2 mL), and the mixture was stirred at room temperature for 14 h. At the end of this period, the reaction mixture was concentrated in vacuo to provide an oil, which was then purified by flash chromatography on silica-gel using ethyl acetate-hexane (1:9) to provide the titled product as a thick colorless oil (0.57 g).

$^1$H-NMR (400 MHz, CDCl$_3$, ppm): δ7.04 (d, 1H), 7.00 (s, 2H), 6.87 (dd, 1H), 6.76 (d, 1H), 5.97 (s, 2H), 5.00 (s, 1H), 4.41 (s, 2H), 3.73 (s, 3H), 2.36 (m, 4H), 1.45 (m, 4H), 0.82 (t, 6H).

Step D: Preparation of N-methylbenzimidazolinone

Cesium carbonate (814.5 mg, 2.5 mmol) was added to a stirred solution of benzimidazolinone (335 mg, 2.5 mmol) in DMF (10 mL) under nitrogen at room temperature. After stirring for 30 min., methyl iodide (355 mg, 2.5 mmol) was added and the mixture stirred at room temperature for 18 h. Water was added and the mixture extracted with ethyl acetate. The organic phase was washed with water, dried (magnesium sulfate) and the solvent removed in vacuo. The residue was chromatographed (10–50% ethyl acetate/hexane) to give the title compound (43 mg, 12%) as a white solid.

$^1$H-NMR (400 MHz, CDCl$_3$, ppm): δ7.10–7.05 (m, 3H), 6.95 (d, 1H), 3.40 (s, 3H).

FAB-MS: m/e 148.9 (M+H).

Step E: Preparation of 1-[4-(1-carbomethoxy-1-(3,4-methylenedioxyphenyl)-methoxy)-3,5-dipropylphenylmethyl-3-methyl-2-benzimidazolinone Cesium carbonate (78 mg, 0.24 mmol) was added to N-methylbenzimidazolinone (from step D) (17.8 mg, 0.12 mmol) in DMF (1.4 mL) at room temperature under nitrogen. After stirring at room temperature for 15 min., a solution of 4-(1-carbomethoxy-1-(3,4-methylenedioxyphenyl)methoxy)-3,5-dipropylbenzyl bromide (from Step C) (70 mg, 0.15 mmol) in DMF (1.4 mL) was added and the mixture stirred at room temperature for 18 hrs. The mixture was poured onto ice/water and extracted with ethyl acetate (4 times). The combined organic phase was washed with water twice, brine, dried (magnesium sulfate) and the solvent removed in vacuo. The crude product was purified by flash chromatography on silica-gel (10–30% ethyl acetate/hexane) to provide the title compound (56 mg, 92%).

$^1$H-NMR (400 MHz, CDCl$_3$, ppm): δ7.1–6.9 (m, 6H), 6.84 (m, 2H), 6.72 (d, 1H), 5.94 (s, 2H), 4.95 (s, 1H), 4.92 (s, 2H), 3.70 (s, 3H), 3.42 (s, 3H), 2.32 (m, 4H), 1.40 (m, 4H), 0.78 (t, 6H).

Step F: Preparation of 1-[4-(1-carboxy-1-(3,4-methylenedioxyphenyl)methoxy)-3,5-dipropylphenylmethyl]-3-methyl-2-benzimidazolinone 5N sodium hydroxide solution (0.2 mL) was added to a stirred mixture of the product from step E (54 mg, 0.10 mmol) in methanol (2 mL). A few drops of methylene chloride were added to allow stirring, then the mixture was stirred at room temperature for 3 hrs. The solution volume was reduced to ~10% in vacuo then 5% citric acid solution was added. The mixture was extracted with ethyl acetate (3 times). The combined organic phase was washed with water, brine, dried (magnesium sulfate) and the solvent removed in vacuo to give the titled compound (40 mg, 77%) as a white solid.

$^1$H-NMR (400 MHz, CD$_3$OD, ppm): δ7.18–6.92 (m, 7H), 6.83 (d, 1H), 6.75 (d, 1H), 5.95 (s, 2H), 5.01 (s, 2H), 4.88 (s, 1H), 3.46 (s, 3H), 2.32 (t, 4H), 1.45 (m, 4H), 0.80 (t, 6H).

FAB-MS: m/e 517.7 (M+H).

EXAMPLE 3

1-[4-(1-Carboxy-1-(3,4-methylenedioxyphenyl)methoxy)-3,5dipropylphenylmethyl]-2-benzimidazolinone The title compound was synthesized in a similar manner to that outlined for Example 2 except that in Step D methyl iodide was replaced by ethyl chloroformate to give N-ethoxycarbonylbenzimidazolinone which was utilized in Step E. The ethoxycarbonyl group was removed under the saponification conditions (Step F).

$^1$H-NMR (400 MHz, CDCl$_3$/CD$_3$OD, ppm): δ7.05–6.82 (m, 7H), 6.72 (d, 1H), 6.63 (d, 1H), 5.90 (s, 2H), 4.93 (s, 2H), 4.88 (s, 1H), 2.25 (t, 4H), 1.45 (m, 2H), 1.28 (m, 2H), 0.76 (t, 6H).

FAB-MS: m/e 541.9 (M+K).

EXAMPLE 4

1-[4-(1-Carboxy-1-(3,4-methylenedioxyphenyl)methoxy)-3,5-dipropylphenylmethyl]-3-(carboxymethyl)-2-benzimidazolinone The title compound was synthesized in a similar manner to that outlined for Example 2 except that in Step D methyl iodide was replaced by ethyl bromoacetate to give N-(ethoxycarbonylmethyl)benzimidazolinone which was utilized in Step E.

$^1$H-NMR (400 MHz, CD$_3$OD, ppm): δ7.12–6.94 (m, 7H), 6.85 (d, 1H), 6.76 (d, 1H), 5.95 (s, 2H), 5.02 (s, 2H), 4.94 (s, 1H), 4.70 (s, 2H), 2.34 (t, 4H), 1.41 (m, 4H), 0.78 (t, 6H).

FAB-MS: m/e 561.8 (M+H).

EXAMPLE 5

1-[4-(1-Carboxy-1-(3,4-methylenedioxyphenyl)methoxy)-3,5-dipropylphenylmethyl]-5,6-dimethyl-2-benzimidazolinone The title compound was synthesized in a similar manner to that outlined for Example 2 except that Step D was omitted and 5,6-dimethylbenzimidazolinone was used directly in Step E to give a mixture of mono- and di-alkylated products that were separated by flash chromatography.

$^1$H-NMR (400 MHz, CD$_3$OD, ppm): δ6.98 (s, 1H), 6.94 (s, 2H), 6.85 (d, 2H), 6.75 (m, 2H), 5.95 (s, 2H), 4.98 (s, 2H), 4.93 (s, 1H), 2.35 (t, 4H), 2.24 (s, 3H), 2.20 (s, 3H), 1.41 (m, 4H), 0.80 (t, 6H).

FAB-MS: m/e 531.8 (M+H).

EXAMPLE 6

1-[4-(1-Carboxy-1-(3,4-methylenedioxyphenyl)methoxy)-3,5-dipropylphenylmethyl]-3-ethyl-2-benzimidazolinone The title compound was synthesized in a similar manner to that outlined for Example 2 except that Step D was omitted and commercially available N-ethylbenzimidazolinone was used directly in Step E.

$^1$H-NMR (400 MHz, CD$_3$OD, ppm): δ7.18–6.92 (m, 7H), 6.82 (d, 1H), 6.76 (d, 1H), 5.96 (s, 2H), 5.00 (s, 2H), 4.95 (s, 1H), 3.99 (q, 2H), 2.32 (t, 4H), 1.41 (m, 4H), 1.34 (t, 3H), 0.78 (t, 6H).

FAB-MS: m/e 531.7 (M+H).

EXAMPLE 7

1-[4-(1-Carboxy-1-(3,4-methylenedioxyphenyl)methoxy)-3,5-dipropylphenylmethyl]-3-phenyl-2-benzimidazolinone The title compound was synthesized in a similar manner to that outlined for Example 2. N-methylbenzimidazolinone was replaced by N-phenylbenzimidazolinone [for synthesis see R.L. Clark, A.A. Pessolano, J. Amer. Chem. Soc., 80, 1657, (1958)] in Step E.

$^1$H-NMR (400 MHz, CD$_3$OD, ppm): δ7.62–7.45 (m, 5H), 7.13–6.98 (m, 7H), 6.86 (d, 1H), 6.78 (d, 1H), 5.98 (s, 2H), 5.09 (s, 2H), 4.99 (s, 1H), 2.36 (t, 4H), 1.46 (m, 4H), 0.80 (t, 6H).

FAB-MS: m/e 579 (M+H).

EXAMPLE 8

1-[4-(1-Carboxy-1-(3,4-methylenedioxyphenyl)methoxy)-3,5-dipropylphenylmethyl]-3,6-dimethyl-2-benzimidazolinone The title compound was synthesized in a similar manner to that outlined for Example 2. N-Methylbenzimidazolinone was replaced by 1,5-dimethylbenzimidazolinone [for synthesis see R.L. Clark, A.A. Pessolano, *J. Amer. Chem. Soc.*, 80, 1657, (1958)] in Step E.

$^1$H-NMR (400 MHz, CD$_3$OD, ppm): δ7.03–6.92 (m, 5H), 6.84 (m, 2H), 6.76 (d, 1H), 5.95 (s, 2H), 4.98 (s, 2H), 4.95 (s, 1H), 3.42 (s, 3H), 2.32 (t, 4H), 2.30 (s, 3H), 1.41 (m, 4H), 0.78 (t, 6H).

FAB-MS: m/e 553.9 (M+Na), 531.7 (M+H).

EXAMPLE 9

1-[4-(1-Carboxy-1-(3,4-methylenedioxyphenyl)methoxy)-3,5-dipropylphenylmethyl]-3-(3-pyridyl)-2-benzimidazolinone The title compound was synthesized in a similar manner to that outlined for Example 2. N-methylbenzimidazolinone was replaced by N-(3-pyridyl)benzimidazolinone [for synthesis see R.L. Clark, A.A. Pessolano, *J. Amer. Chem. Soc.*, 80, 1657, (1958)] in Step E.

$^1$H-NMR (400 MHz, CD$_3$OD, ppm): δ8.85 (br. s, 1H), 8.65 (br. s, 1H), 8.12 (d, 1H), 7.68 (br, s, 1H), 7.21–6.98 (m, 7H), 6.85 (d, 1H), 6.76 (d, 1H), 5.98 (s, 2H), 5.10 (s, 2H), 4.98 (s, 1H), 2.36 (t, 4H), 1.45 (m, 4H), 0.80 (t, 6H).

FAB-MS: m/e 602.6 (M+Na), 580.7 (M+H).

EXAMPLE 10

1-[4-(1-Carboxy-1-(3,4-methylenedioxyphenyl)methoxy)-3-chloro5-propylphenylmethyl]-2-benzimidazol in one

Step A: Preparation of methyl 3-chloro-4-hydroxy-5-(prop-2-ene-1-yl)benzoate To a 250 mL rb flask equipped with a magnetic stir bar and a reflux condenser was added a solution of 10.33 g (55.4 mmol) of methyl 3-chloro-4-hydroxybenzoate dissolved in 110 mL of acetone and 5.27 mL (60.9 mmol) of allyl bromide and 15.30 g (0.111 mol) of powdered potassium carbonate was added. The reaction was stirred and refluxed for 6 hours, then cooled and filtered. The tiltrate was evaporated in vacuo and the residue was purified on a silica gel flash chromatography column eluted with 10% EtOAc-hexane to afford 10.462 g (84%) of the title compound.

$^1$H NMR (400 MHz, CDCl$_3$, ppm): δ3.43 (d, J=6.80 Hz, 2H), 3.87 (s, 3H), 5.07–5.11 (m, 2H), 5.92–6.03 (m, 2H), 7.74 (d, J=2.40 Hz, 1H), 7.91 (d,J=2.40 Hz, 1H).

Step B: Preparation of methyl 3-chloro-4-hydroxy-5-propylbenzoate

A Parr flask was charged with a solution of 14.784 g (65.2 mmol) of the product of step A dissolved in 80 mL ethanol and 0.485 g of 5% rhodium on alumina catalyst was added. The reaction mixture was mounted in a Parr hydrogenation apparatus, pressurized to 40 psig hydrogen and shaken for 30 minutes. The reaction vessel was then removed from the apparatus, the contents were filtered and the flitrate was evaporated and dried in vacuo to afford 14.878 g (99%) of the title compound.

$^1$H NMR (400 MHz, CDCl$_3$, ppm): δ0.93 (t, J=7.60 Hz, 3H), 1.57–1.70 (m, 2H), 2.63 (t, J=7.60 Hz, 2H), 3.86 (s, 3H), 6.05 (s, 1H), 7.72 (d, J=1.60 Hz, 1H), 7.86 (d, J=1.60 Hz, 1H).

EI-MS: m/e 228 (M+).

Step C: Preparation of 3-chloro-4-hydroxy-5-propylbenzyl alcohol

To a stirred solution of 14.878 g (65.1 mmol) of the product of step B in 100 mL methylene chloride was added 8.796 g (72.0 mmol) of 4-dimethylaminopyridine, 10.787 g (71.6 mmol) of tert-butyldimethylchlorosilane and the mixture was stirred at room temperature for 3 hours. The reaction mixture was partitioned between methylene chloride and water, the organic layer was separated, washed with 1.0 N HCl, 5% NaHCO$_3$, dried (MgSO$_4$), filtered and evaporated. The residue (20.293 g) was dissolved in 60 mL of anhydrous THF, magnetically stirred at 0° C, and then treated with 130 mL of a 1.0 M solution of lithium triethylborohydride under a nitrogen atmosphere. The reaction was allowed to warm to room temperature, and treated with several mL water until hydrogen evolution ceased. The reaction mixture was evaporated in vacuo, redissolved in methylene chloride, dried (MgSO$_4$), filtered and evaporated again in vacuo. The residue (16.767 g) was finally redissolved in 50 mL THF and treated with 53.2 mL of a 1.0 M solution of tetrabutylammonium fluoride in THF while stirring for 12 hours at room temperature. The reaction mixture was then evaporated to an oil and purified on a silica gel flash chromatography column eluted with 25% EtOAc-hexane to afford 8.877 g (70%) of the title compound.

$^1$H NMR (400 MHz, CDCl$_3$, ppm): δ0.93 (t, J=7.60 Hz, 3H), 1.57–1.63 (m, 2H), 2.59 (t, J=7.60 Hz, 2H), 4.10 (br s, 2H), 4.51 (d, J=3.60 Hz, 2H), 6.98 (s, 1H), 7.14 (s, 1H).

EI-MS: m/e 200 (M+).

Step D: Preparation of methyl 2-(2-chloro-4-hydroxymethyl-6-propylphenoxy)-2-(3,4-methylenedioxyphenyl)acetate To a solution of 0.280 g (1.40 mmol) of the product of step C and 0.762 g () of methyl α-bromo-3,4-methylenedioxyphenylacetate in 3.0 mL of acetone was added 0.386 g (2.80 mmol) of finely powdered potassium carbonate and the mixture was stirred and heated at reflux for 2 hours. At this point, the reaction mixture was cooled to room temperature, filtered, and evaporated in vacuo. The residue was purified on a silica gel flash chromatography column eluted with 30% EtOAc-hexane. Evaporation of the purified fractions and solvent removal in vacuo afforded 0.445 g (81%) of the title compound.

$^1$H NMR (400 MHz, CDCl$_3$, ppm): δ0.78 (t, J=7.20 Hz, 3H), 1.20–1.30 (m, 1H), 1.41–1.53 (m, 1H), 1.82 (br s, 1H), 2.27–2.43 (m, 2H), 3.73 (s, 3H), 4.55 (s, 2H), 5.41 (s, 1H), 5.95 (s, 2H), 6.74 (d, J=8.00 Hz, 1H), 6.86 (dd, J=1.60, 8.00 Hz, 1H), 6.97 (d, J=2.00 Hz, 1H), 7.01 (d, J=1.60 Hz, 1H), 7.19 (d, J=2.00 Hz, 1H).

EI-MS: m/e 392 (M+).

Step E: Preparation of methyl 2-(4-bromomethyl-2-chloro-6-propylphenoxy)-2-(3,4-methylenedioxyphenyl)acetate To a cooled (0°–5° C.), magnetically stirred solution of 0.445 g (1.13 mmol) of the product of step D and 0.446 g (1.70 mmol) of triphenylphosphine dissolved in 5 mL of dichloromethane was added 0.564 g (1.70 mmol) of carbon tetrabromide in several portions. After the addition was complete, the reaction was allowed to warm to room temperature and was stirred an additional 30 minutes. The methylene chloride was then removed in vacuo, and the residue was applied to a silica gel flash chromatography column and eluted with 10% EtOAc-hexane. Evaporation of the purified fractions and drying in vacuo afforded the title compound which was used directly in the next step without further characterization.

Step F: Preparation of 1-[4-(1-carbomethoxy-1-(3,4-methylenedioxyphenyl)-methoxy)-3-chloro-5-propylphenylmethyl]-3-carboethoxy-2-benzimidazolinone To a solution of 0.069 g (0.33 mmol) of 1-carboethoxy-2-benzimidazolinone dissolved in 0.6 mL DMF was added 0.217 g (0.66 mmol) of powdered cesium carbonate and the resulting suspension was stirred under a nitrogen atmosphere at room temperature for 30 minutes. A solution of the product of step E in 0.5 mL DMF was then added and the reaction mixture was stirred for an additional 15 hours. The mixture was then partitioned between EtOAc and water and extracted. The organic layer was separated, dried (MgSO$_4$), filtered and evaporated, and the residue was purified on a silica gel flash chromatography column eluted with 30% EtOAc-hexane. Evaporation of the purified fractions and drying in vacuo afforded 0.088 g (45%) of the title compound.

$^1$H NMR (400 MHz, CDCl$_3$, ppm): δ0.75 (t, J=7.60 Hz, 3H), 1.18–1.27 (m, 1H), 1.37–1.46 (m, 1H), 1.48 (t, J=7.20 Hz, 3H), 2.25–2.42 (m, 2H), 3.72 (s, 3H), 4.53 (q, J=7.20 Hz, 2H), 4.90 (s, 2H), 5.38 (s, 1H), 5.95 (s, 2H), 6.73 (d, J=8.00 Hz, 1H), 6.82–6.86 (m, 2H), 6.97 (d, J=2.40 Hz, 1H), 6.99 (d, J=1.60 Hz, 1H), 7.12–7.16 (m, 3H), 7.86–7.89 (m, 1H).

FAB-MS: m/e 581 (M+1).

Step G: Preparation of 1-[4-(1-carboxy-1-(3,4-methylenedioxyphenyl)methoxy)-3-chloro-5-propylphenylmethyl]-2-benzimidazolinone.

To a solution of 0.088 g (0.15 mmol) of the product of step F in 4 mL of methanol was added 250 μL of a 5.0 N solution of sodium hydroxide and the reaction was stirred at room temperature for 2 hours. The reaction mixture was then adjusted to pH=6 with dropwise addition of 2 N hydrochloric acid, and then concentrated in vacuo. The residue was redissolved in methanol, filtered, and evaporated. The mixture was then purified on a silica gel flash chromatography column eluted with CHCl$_3$-MeOH-NH$_4$OH (80:15:1). Evaporation of the purified fractions and drying in vacuo afforded 0.038 g (51%) of the title compound.

$^1$H NMR (400 MHz, CD$_3$OD, ppm): δ0.72 (t, J=7.20 Hz, 3H), 1.05–1.15 (m, 1H), 1.36–1.45 (m, 1H), 2.20 (t, J=8.00 Hz, 2H), 4.96 (s, 2H), 5.13 (s, 1H), 6.67 (d, J=8.00 Hz, 1H), 6.76 (dd, J=2.00, 8.00 Hz, 1H), 6.95–7.08 (m, 6H), 7.16 (d, J=2.40 Hz, 1H).

FAB-MS: m/e 495 (M+1).

EXAMPLE 11

1-[4-(1-Carboxy-1-(3,4-methylenedioxyphenyl)methoxy)-3,5-dichlorophenylmethyl]-2-benzimidazolinone Step A: Preparation of ethyl 2-(2,6-dichloro-4-hydroxymethylphenoxy)-2-(3,4-methylenedioxyphenyl) acetate.

To a solution of 0.120 g (0.62 mmol) of 2,6-dichloro-4-hydroxymethylphenol in 1.5 mL of DMF was added 0.223 g (0.68 mmol) of cesium carbonate and the reaction mixture was stirred at room temperature for 20 minutes. A solution of 0.196 g (0.68 mmol) of ethyl α-bromo-3,4-methylenedioxyphenylacetate in 0.5 mL of DMF was then added and the reaction mixture was stirred at room temperature for an additional 30 minutes. The mixture was then partitioned between ethyl acetate and 10% aqueous citric acid and extracted. The organic layer was separated, washed once with saturated aqueous sodium bicarbonate and once with brine, dried (MgSO$_4$), filtered and evaporated. The residue was purified on a silica gel flash chromatography column eluted with 40% EtOAc-hexane. Combination of the purified fractions and evaporation in vacuo afforded 0.214 g (86%) of the title compound.

$^1$H NMR (200 MHz, CDCl$_3$, ppm): δ1.25 (t, J=7.20 Hz, 3H), 4.15–4.30 (m, 2H), 4.60 (s, 2H), 5.69 (s, 1H), 5.97 (s, 2H), 6.75 (d, J=8.00 Hz, 1H), 6.93 (dd, J=1.80, 8.00 Hz, 1H), 7.09 (d, J=1.80 Hz, 1H), 7.26 (s, 2H).

FAB-MS: m/e 399, 401 (M+I).

Step B: Preparation of ethyl 2-(4-bromomethyl-2,6-dichlorophenoxy)-2-(3,4-methylenedioxyphenyl)acetate To a solution of 0.206 g (0.52 mmol) of the product of step A and 0.162 g (0.62 mmol) of triphenylphosphine in 2 mL of methylene chloride was added 0.205 g (0.62 mmol) of carbon tetrabromide at 0° C. (ice water bath). After 10 minutes, the ice bath was removed and the reaction mixture was stirred at room temperature for 2.5 hours. The methylene chloride was removed in vacuo and the residue was purified on a silica gel flash chromatography column eluted with 15% EtOAc-hexane. The purified fractions were combined, evaporated and dried in vacuo to afford 0.220 g (92%) of the title compound.

$^1$H NMR (200 MHz, CDCl$_3$, ppm): δ1.24 (t, J=7.20 Hz, 3), 4.15–4.30 (m, 2H), 4.33 (s, 2H), 5.70 (s, 1H), 5.97 (s, 1H), 5.98 (s, 1H), 6.76 (d, J=7.80 Hz, 1H), 6.94 (dd, J=1.80, 7.80 Hz, 1H), 7.10 (d, J=1.80 Hz, 1H), 7.28 (s, 2H).

FAB-MS: m/e 461,463 (M+1).

Step C: Preparation of 1-[4-(1-carboethoxy-1-(3,4-methylenedioxyphenyl)methoxy)-3,5-dichlorophenylmethyl]-3-carboethoxy-2-benzimidazolinone To a solution of 0.048 g (0.24 mmol) of 1-carboethoxy-2-benzimidazolinone dissolved in 0.5 mL DMF was added 0.010 g (0.26 mmol) of a 60% oil dispersion of sodium hydride and the resulting mixture was stirred under a nitrogen atmosphere and gently warmed with a heat gun until the solids had dissolved. A solution of the product of step B in 1.0 mL DMF was then added and the reaction mixture was stirred for an additional 1.5 hours. The mixture was then quenched with 5% aqueous ammonium chloride and extracted into ethyl acetate. The organic layer was separated, dried (MgSO$_4$), filtered and evaporated, and the residue was purified on a silica gel flash chromatography column eluted with 30% EtOAc-hexane. Evaporation of the purified fractions and drying in vacuo afforded 0.088 g (64%) of the title compound.

$^1$H NMR (200 MHz, CDCl$_3$, ppm): δ1.22 (t, J=7.00 Hz, 3H), 1.50 (t, J=7.00 Hz, 3H), 4.12–4.28 (m, 2H), 4.55 (q, J=7.00 Hz, 2H), 4.91 (s, 2H), 5.65 (s, 1H), 5.96 (s, 1H), 5.97 (s, 1H), 6.73 (d, J=8.00 Hz, 1H), 6.82–6.86 (m, 1H), 6.91 (dd, J=1.60, 8.00 Hz, 1H), 7.07 (d, J=1.60 Hz, 1H), 7.12–7.30 (m, 4H), 7.90–7.94 (m, 1H).

FAB-MS: m/e 587 (M+1).

Step D: Preparation of 1-[4-(1-carboxy-1-(3,4-methylenedioxyphenyl)methoxy)-3,5-dichlorophenylmethyl]-2-benzimidazolinone.

To a solution of 0.082 g (0.14 mmol) of the product of step C in 1.0 mL of methanol and 1.0 mL methylene chloride was added 250 gL of a 5.0 N solution of sodium hydroxide and the reaction was stirred at room temperature for 16 hours. The reaction mixture was then adjusted to pH=5–6 with dropwise addition of 6 N hydrochloric acid, and then concentrated in vacuo. The residue was redissolved in methanol, filtered, and evaporated. The mixture was then purified on a silica gel flash chromatography column eluted with CHCl$_3$—MeOH—NH$_4$OH (80:15:1). Evaporation of the purified fractions and drying in vacuo afforded 0.061 g (90%) of the title compound.

$^1$H NMR (400 MHz, CD$_3$OD, ppm): δ4.98 (s, 2H), 5.57 (s, 1H), 5.91 (s, 1H), 5.92 (s, 1H), 6.68 (d, J=8.00 Hz, 1H), 6.82 (dd, J=1.60 8.00 Hz, 1H), 6.97–6.99 (m, 2H), 7.04–7.09 (m, 3H), 7.25 (s, FAB-MS: m/e 487 (M+1).

EXAMPLE 12

1-[4-(1-Carboxy-1-(3,4-methylenedioxyphenyl)methoxy)-3-propylphenylmethyl]-2-benzimidazolinone Step A: Preparation of 4-tert-butyldimethylsilyloxy-3-propylbenzyl bromide To a solution of 1.00 g (3.57) of 4-tert-butyldimethylsilyloxy-3-propylbenzyl alcohol and 1.12 g (4.00 mmol) of triphenylphosphine in 10 mL methylene chloride was added 1.42 g (4.00 mmol) of carbon tetrabromide in portions as the reaction mixture was magnetically stirred at 0°–5° C. After the addition was complete, the ice-water bath was removed and the reaction was stirred for an additional 30 minutes and allowed to warm to room temperature. The methylene chloride was removed in vacuo, and the residue was applied to a silica gel flash chromatography column and eluted with 5% EtOAc-hexane. The purified fractions were combined, evaporated and dried in vacuo to afford 1.10 g (90%) of the title compound.

$^1$H NMR (200 MHz, CDCl$_3$, ppm): δ0.22 (s, 6H), 0.94 (t,J=7.20 Hz, 3H), 1.00 (s, 9H), 1.52–1.64 (m, 2H), 2.53 (t, J=7.80 Hz, 2H), 4.47 (s, 2H), 6.71 (d, J=8.40 Hz, 1H), 7.08 (dd, J=2.40, 8.40 Hz, 1H), 7.15 (d, J=2.40 Hz, 1H).

EI-MS: m/e 342, 344 (M+1).

Step B: Preparation of 1-(4-tert-butyldimethylsilyloxy-3-propylphenylmethyl)-3-carboethoxy-2-benzimidazolinone To a solution of 0.295 g (1.43 mmol) of 1-carboethoxy-2-benzimidazolinone dissolved in 5.0 mL DMF was added 0.063 g (1.57 mmol) of a 60% oil dispersion of sodium hydride and the resulting mixture was stirred under a nitrogen atmosphere and gently warmed with a heat gun until the solids had dissolved and gas evolution had ceased. A solution of the product of step A in 2.0 mL DMF was then added and the reaction mixture was stirred for an additional 0.5 hours. The mixture was then quenched with 10% aqueous citric acid and extracted into ethyl acetate. The organic layer was separated, washed with saturated sodium bicarbonate and brine, dried (MgSO$_4$), filtered and evaporated, and then the residue was purified on a silica gel flash chromatography column eluted with 30% EtOAc-hexane. Evaporation of the purified fractions and drying in vacuo afforded 0.088 g (64%) of the title compound.

$^1$H NMR (400 MHz, CDCl$_3$, ppm): δ0.17 (s, 6H), 0.88 (t, J=7.20 Hz, 3H), 0.96 (s, 9H), 1.47 (t, J=7.20 Hz, 3H), 1.47–1.52 (m, 2H), 2.47 (t, J=7.60 Hz, 2H), 4.52 (q, J=7.20 Hz, 2H), 4.92 (s, 2H), 6.66 (d, J=8.40 Hz, 1H), 6.88–6.91 (m, 1H), 7.02 (dd, J=2.40, 8.40 Hz, 1H), 7.08–7.13 (m, 3H), 7.84–7.85 (m, 1H).

FAB-MS: m/e 469 (M+1).

Step C: Preparation of 1-(4-hydroxy-3-propylphenylmethyl)-3-carboethoxy-2-benzimidazolinone To a solution of 0.334 g (0.71 mmol) of the product of step B in 1 mL of anhydrous THF was added 728 gL (0.73 mmol) of a 1.0 M solution of tetrabutylammonium fluoride in THF and the resulting mixture was stirred at room temperature for 10 minutes. The THF was then removed in vacuo and the residue was purified on a silica gel flash chromatography column eluted with 40% EtOAc-hexane. Combination of the product containing fractions and evaporation in vacuo afforded 0.109 g (43%) of the title compound.

$^1$H NMR (400 MHz, CD$_3$OD, ppm): δ0.88 (t, J=7.20 Hz, 3H), 1.46 (t, J=7.20 Hz, 3H), 1.50–1.58 (m, 2H), 2.50 (t, J=7.60 Hz, 2H), 4.51 (q, J=7.60 Hz, 2H), 4.95 (s, 2H), 6.67 (d, J=8.00 Hz, 1H), 7.00 (dd, J=2.40, 8.00 Hz, 1H), 7.06–7.19 (m, 4H), 7.83 (dd, J=1.60, 7.40 Hz, 1H).

FAB-MS: m/e 355 (M+1).

Step D: Preparation of 1-[4-(1-carboethoxy-1-(3,4-methylenedioxyphenyl)methoxy)-3-propylphenylmethyl]-3-carboethoxy-2-benzimidazolinone To a solution of 0.105 g (0.30 mmol) of the product of step C in 1.0 mL of DMF was added 0.115 g (0.33 mmol) of cesium carbonate and the resulting suspension was stirred under a nitrogen atmosphere for 15 minutes. A solution of 0.094 g (0.33 mmol) ethyl α-bromo-3,4-methylenedioxyphenylacetate in 0.5 mL of DMF was then added and the reaction mixture was stirred at room temperature overnight. The reaction mixture was then suspended in 10% aqueous citric acid and extracted into ethyl acetate. The organic layer was separated, washed with saturated sodium bicarbonate, brine, dried (MgSO$_4$), filtered and evaporated. The residue was purified on a silica gel flash chromatography column eluted with 30% EtOAc-hexane; combination of the product fractions and evaporation in vacuo afforded 0.137 g (83%) of the title compound.

$^1$H NMR (400 MHz, CDCl$_3$, ppm): δ0.91 (t, J=7.60 Hz, 3H), 1.15 (t, J=7.20 Hz, 3H), 1.47 (t, J=7.20 Hz, 3H), 1.53–1.68 (m, 2H), 2.55–2.70 (m, 2H), 4.07–4.15 (m, 2H), 4.52 (q, J=7.20 Hz, 2H), 4.92 (s, 2H), 5.45 (s, 1H), 5.95 (s, 2H), 6.61 (d, J=8.40 Hz, 1H), 6.78 (d, J=8.00

Hz, 1H), 6.85–6.88 (m, 1H), 6.99 (dd, J=1.40, 8.00 Hz, 1H), 7.03–7.14 (m, 5H), 5.85–5.87 (m, 1H).
FAB-MS: m/e 561 (M+1).

Step E: Preparation of
1-[4-(1-carboxy-1-(3,4-methylenedioxyphenyl)methoxy)-3-propylphenylmethyl]-2-benzimidazolinone The product of step D (0.132 g, 0.24 mmol) was suspended in 2.0 mL of methanol and the flask was placed in a sonicator bath until the contents were completely dissolved. Next, 95 μL of a 5.0 N solution of sodium hydroxide were added and the reaction was stirred at room temperature overnight. The reaction mixture was then adjusted to pH=5–6 with dropwise addition of 6 N hydrochloric acid, and then concentrated in vacuo. The residue was redissolved in methanol, filtered, and evaporated. The mixture was then purified on a silica gel flash chromatography column eluted with CHCl$_3$-MeOH-NH$_4$OH (80:15:1). Evaporation of the purified fractions and drying in vacuo afforded 0.038 g (35%) of the title compound.

$^1$H NMR (400 MHz, CD$_3$OD, ppm): δ0.86 (t, J=7.60 Hz, 3H), 1.54–1.60 (m, 2H), 2.50–2.57 (m, 1H), 2.71–2.78 (m, 1H), 4.96 (s, 2H), 5.25 (s, 1H), 5.90 (d, J=1.20 Hz, 1H), 5.91 (d, J=1.20 Hz, 1H), 6.75 (d, J=8.40 Hz, 1H), 6.79 (d, J=8.40 Hz, 1H), 6.95–7.11 (m, 8H).
FAB-MS: m/e 461 (M+1).

EXAMPLE 13

1-[4-(1-Carboxy-1-(3,4-methylenedioxyphenyl)methoxy)-3-ethylphenylmethyl]-2-benzimidazolinone Step A: Preparation of ethyl 2-(2-ethyl-4-hydroxymethylphenoxy)-2-(3,4-methylenedioxyphenyl) acetate To a solution of 0.146 g (0.96 mmol) of 3-ethyl-4-hydroxybenzyl alcohol in 2.0 mL of DMF was added 0.319 g (0.98 mmol) of cesium carbonate and the reaction mixture was stirred at room temperature for 10 minutes. A solution of 0.281 g (0.68 mmol) of ethyl α-bromo-3,4-methylenedioxyphenylacetate in 1.0 mL of DMF was then added and the reaction mixture was stirred at room temperature for an additional 30 minutes. The mixture was then partitioned between ethyl acetate and 10% aqueous citric acid and extracted. The organic layer was separated, washed once with saturated aqueous sodium bicarbonate and once with brine, dried (MgSO$_4$), filtered and evaporated. The residue was purified on a silica gel flash chromatography column eluted with 40% EtOAc-hexane. Combination of the purified fractions and evaporation in vacuo afforded 0.278 g (81%) of the title compound.

$^1$H NMR (200 MHz, CDCl$_3$, ppm): δ1.19 (t,J=7.20 Hz, 3H), 1.26 (t, J=7.60 Hz, 3H), 2.70–2.82 (m, 2H), 4.10–4.23 (m, 2H), 4.59 (s, 2H), 5.54 (s, 1H), 5.98 (s, 2H), 6.70 (d, J=8.40 Hz, 1H), 6.82 (d, J=8.00 Hz, 1H), 7.03–7.09 (m, 3H), 7.19 (br s, 1H).
FAB-MS: m/e 359 (M+1).

Step B: Preparation of ethyl 2-(4-bromomethyl-2-ethylphenoxy)-2-(3,4-methylenedioxyphenyl) acetate To a cooled (0°–5° C.), magnetically stirred solution of 0.27 1 g (0.76 mmol) of the product of step A and 0.238 g (0.91 mmol) of triphenylphosphine dissolved in 3 mL of dichloromethane was added 0.301 g (1.70 mmol) of carbon tetrabromide in several portions. After the addition was complete, the reaction was allowed to warm to room temperature and was stirred an additional 2.5 hours. At this point TLC analysis (50% EtOAc-hexane) indicated that starting material remained, therefore an additional 0.030 g of triphenylphosphine and 0.050 g of carbon tetrabromide were added. After 4 hours, the methylene chloride was removed in vacuo, and the residue was applied to a silica gel flash chromatography column and eluted with 15% EtOAc-hexane. Evaporation of the purified fractions and drying in vacuo afforded 0.308 g (96%) of the title compound.

$^1$H NMR (400 MHz, CDCl$_3$, ppm): δ1.19 (t, J=7.20 Hz, 1H), 1.26 (t, J=7.60 Hz, 1H), 2.68–2.80 (m, 2H), 4.10–4.25 (m, 2H), 4.47 (s, H), 5.53 (s, 1H), 5.98 (s, 2H), 6.66 (d, J=8.40 Hz, 1H), 6.82 (d, J=7.80 Hz, 1H), 7.02–7.15 (m, 3 H), 7.21 (br s, 1H).
FAB-MS: m/e 341 (M+-Br).

Step C: Preparation of
1-[4-(1-carboethoxy-1-(3,4-methylenedioxyphenyl)methoxy)-3-ethylphenylmethyl]-3-carboethoxy-2-benzimidazolinone To a solution of 0.020 g (0.10 mmol) of 1-carboethoxy-2-benzimidazolinone dissolved in 250 μL DMF was added 0.035 g (0.11 mmol) of cesium carbonate and the resulting suspension was stirred under a nitrogen atmosphere for 10 minutes. A solution of the product of step B in 300 μL DMF was then added and the reaction mixture was stirred for an additional I hour. The mixture was suspended in 10% aqueous citric acid and extracted into ethyl acetate. The organic layer was separated, washed with saturated sodium bicarbonate and brine, dried (MgSO$_4$), filtered, evaporated, and the residue was purified on a silica gel flash chromatography column eluted with 30% EtOAc-hexane. Evaporation of the purified fractions and drying in vacuo afforded 0.034 g (64%) of the title compound.

$^1$H NMR (400 MHz, CDCl$_3$, ppm): δ1.17 (t, J=7.20 Hz, 3H), 1.22 (t, J=7.60 Hz, 3H), 1.50 (t, J=7.20 Hz, 3H), 2.64–2.76 (m, 2H), 4.08–4.20 (m, 2H), 4.54 (q, J=7.20 Hz, 2H), 4.95 (s, 2H), 5.49 (s, 1H), 5.98 (s, 2H), 6.64 (d, J=8.20 Hz, 1H), 6.80 (d, J=8.00 Hz, 1H), 6.87–6.95 (m, 1H), 7.00–7.19 (m, 6H), 7.86–7.92 (m, 1H).
FAB-MS: m/e 547 (M+1).

Step D: Preparation of
1-[4-(1-carboxy-1-(3,4-methylenedioxyphenyl)methoxy)-3-ethylphenylmethyl]-2-benzimidazolinone A round bottom flask was charged with 0.031 g (0.06 mmol) of the product of step C, 0.5 mL of ethanol and the flask and its contents were placed in a sonicator bath. Methylene chloride (0.2 mL) was then added in order to completely dissolve the starting material. Next, 23 μL of a 5.0 N solution of sodium hydroxide were added and the reaction was stirred at room temperature overnight. The reaction mixture was then adjusted to pH=5 with dropwise addition of 6 N hydrochloric acid, and then concentrated in vacuo. The residue was redissolved in methanol, filtered, and evaporated. The mixture was then purified on a silica gel flash chromatography column eluted with CHCl$_3$-MeOH-NH$_4$OH (80: 15:1). Evaporation of the purified fractions and drying in vacuo afforded 0.012 g (48%) of the title compound.

$^1$H NMR (400 MHz, CD$_3$OD, ppm): δ1.14 (t, J=7.60 Hz, 3H), 2.61–2.68 (m, 1H), 2.69–2.79 (m, 1H), 4.96 (s, 2H), 5.31 (s, 1H), 5.91 (s, 2H), 6.76 (d, J=8.00 Hz, 1H), 6.78 (d, J=7.20 Hz, 1H), 6.96–7.07 (m, 6H), 7.10–7.13 (m, 2H).

FAB-MS: m/e 447 (M+1).

EXAMPLE 14

1-[4-(1-Carboxy-1-(3,4-methylenedioxyphenyl)methoxy)phenylmethyl]-2-benzimidazolinone

Step A: Preparation of ethyl 2-(4-hydroxymethylphenoxy)-2-3,4-methylenedioxyphenyl)acetate To a solution of 0.130 g (1.05 mmol) of 4-hydroxybenzyl alcohol in 2.0 mL DMF was added 0.348 g (1.07 mmol) of cesium carbonate and the resulting suspension was stirred under a nitrogen atmosphere for 5 minutes. A solution of 0.308 g (1.07 mmol) of ethyl α-bromo-3,4-methylenedioxyphenylacetate in 1 mL DMF was then added and the reaction mixture was stirred under a nitrogen atmosphere at room temperature for 30 minutes. The reaction mixture was then suspended in 10% aqueous citric acid and extracted with ethyl acetate. The organic layers were separated, washed first with saturated sodium bicarbonate then with brine, dried (MgSO4), filtered, and evaporated. The residue was purified on a silica gel flash chromatography column eluted with 40% EtOAc-hexane. Combination of the product containing fractions and evaporation in vacuo afforded 0.246 g (71%) of the title compound.

$^1$H NMR (200 MHz, CDCl$_3$, ppm): δ1.22 (t, J=7.20 Hz, 3H), 4.11–4.27 (m, 2H), 4.61 (s, 2H), 5.52 (s, 1H), 5.97 (s, 2H), 6.81 (d, J=8.00 Hz, 1H), 6.88–7.07 (m, 3H), 7.23–7.29 (m, 2H).

FAB-MS: m/e 331 (M+1).

Step B:. Preparation of ethyl 2-(4-bromomethylphenoxy)-2-(3,4-methylenedioxyphenyl)acetate To a cooled (0°–5° C.), magnetically stirred solution of 0.238 g (0.63 mmol) of the product of step A and 0.197 g (0.75 mmol) of triphenylphosphine dissolved in 3 mL of dichloromethane was added 0.287 g (0.75 mmol) of carbon tetrabromide in several portions. After the addition was complete, the reaction was allowed to warm to room temperature and was stirred 2.5 hours. At this point TLC analysis (50% EtOAc-hexane) indicated that starting material remained, therefore an additional 0.030 g of triphenylphosphine and 0.050 g of carbon tetrabromide were added. After 4 hours, the methylene chloride was removed in vacuo, and the residue was applied to a silica gel flash chromatography column and eluted with 10% EtOAc-hexane. Evaporation of the purified fractions and drying in vacuo afforded 0.271 g (96%) of the title compound.

$^1$H NMR (200 MHz, CDCl$_3$, ppm): δ1.22 (t, J=7.20 Hz, 3H), 4.12–4.28 (m, 2H), 4.47 (s, 2H), 5.50 (s, 1H), 5.97 (s, 2H), 6.81 (d, J=7.80 Hz, 1H), 6.89 (d, J=8.40 Hz, 1H), 6.85–6.94 (m, 1H), 7.00–7.08 (m 2H), 7.26–7.34 (m, 2H).

FAB-MS: m/e 206 (Base).

Step C: Preparation of 1-[4-(1-carboethoxy-1-(3,4-methylenedioxyphenyl)methoxy)phenylmethyl]-3-carboethoxy-2-benzimidazolinone To a solution of 0.020 g (0.10 mmol) of 1-carboethoxy-2-benzimidazolinone dissolved in 250 gL DMF was added 0.035 g (0.11 mmol) of cesium carbonate and the resulting suspension was stirred under a nitrogen atmosphere for 10 minutes. A solution of the product of step B in 300 aL DMF was then added and the reaction mixture was stirred for an additional 1 hour. The mixture was suspended in 10% aqueous citric acid and extracted into ethyl acetate. The organic layer was separated, washed with saturated sodium bicarbonate and brine, dried (MgSO4), filtered, evaporated, and the residue was purified on a silica gel flash chromatography column eluted with 30% EtOAc-hexane. Evaporation of the purified fractions and drying in vacuo afforded 0.029 g (58%) of the title compound.

$^1$H NMR (200 MHz, CDCl$_3$, ppm): δ1.20 (t, J=7.20 Hz, 3H), 1.49 (t, J=7.20 Hz, 3H), 4.12–4.26 (m, 2H), 4.4.54 (q, J=7.20 Hz, 2H), 4.96 (s, 2H), 5.46 (s, 1H), 5.97 (s, 2H), 6.80–7.32 (m, 1 OH), 7.86–7.94 (m, 1H).

FAB-MS: m/e 519 (M+1).

Step D: Preparation of 1-[4-(1-carboxy-1-(3,4-methyl-enedioxyphenyl)methoxy)-phenylmethyl]-2-benzimidazolinone A round bottom flask was charged with 0.025 g (0.05 mmol) of the product of step C, 0.5 mL of ethanol and the flask and its contents were placed in a sonicator bath. Methylene chloride (0.3 mL) was then added in order to completely dissolve the starting material. Next, 20 μL of a 5.0 N solution of sodium hydroxide were added and the reaction was stirred at room temperature overnight. The reaction mixture was then adjusted to pH=5 with dropwise addition of 6 N hydrochloric acid, and then concentrated in vacuo. The residue was suspended in water to dissolve inorganic salts and filtered. The flitrate was washed with methanol and dried in vacuo to afford 0.016 g (80%) of the title compound.

$^1$H NMR (400 MHz, CD$_3$OD, ppm): δ4.99 (s, 2H), 5.59 (s, 1H), 5.94 (s, 2H), 6.79 (d, J=8.40 Hz, 1H), 6.91 (d, J=8.80 Hz, 2H), 6.95–7.06 (m, 6H), 7.23 (d, J=8.80 Hz, 2H).

FAB-MS: m/e 419 (M+1).

EXAMPLE 15

1-[4-(1-Carboxy-1-(3,4-methylenedioxyphenyl)methoxy)-3,5-dimethoxyphenylmethyl]-2-benzimidazolinone

Step A: Preparation of ethyl 2-(3,5-dimethoxy-4-formylphenoxy)-2-(3,4-methylenedioxyphenyl)acetate To a solution of 0.300 g (1.65 mmol) of syringe aldehyde (3,5-dimethoxy-4-hydroxybenzaldehyde) in 3.0 mL of DMF was added 0.564 g (1.73 mmol) of cesium carbonate and the resulting mixture was stirred under a nitrogen atmosphere for 5 minutes. A solution of 0.497 g (1.73 mmol) of ethyl α-bromo-3,4-methylenedioxyphenylacetate in 2.0 mL of DMF was added and the reaction mixture was stirred at room temperature overnight. The reaction mixture was then suspended in 10% aqueous citric acid and extracted into ethyl acetate. The organic layer was separated, washed first with saturated aqueous sodium bicarbonate and then with brine, dried (MgSO4), filtered and evaporated. The residue was purified on a silica gel flash chromatography column eluted with 30% EtOAc-hexane; combination of the purified fractions and evaporation in vacuo afforded 0.550 g (86%) of the title compound.

$^1$H NMR (200 MHz, CDCl$_3$, ppm): a 1.24 (t, J=7.20 Hz, 3H), 3.88 (s, 6H), 4.14–4.28 (m,2H), 5.81 (s, 1H), 5.95 (s, 2H), 6.73 (d, J=8.00 Hz, 1H), 6.97 (dd, J=1.60, 8.00 Hz, 1H), 7.06 (s, 2H), 7.12 (d, J=1.60 Hz, 1H), 9.83 (s, 1H).

FAB-MS: m/e 389 (M+1).

Step B: Preparation of ethyl 2-(3,5-dimethoxy-4-hydroxymethylphenoxy)-2-(3,4-methylenedioxyphenyl) acetate A magnetically stirred solution of 0.546 g (1.41 mmol) of the product of step A dissolved in 5 mL of ethanol was treated with 0.053 g (1.41 mmol) of sodium borohydride at room temperature. After the addition was complete, the reaction mixture was stirred an additional 10 minutes then partitioned between ethyl acetate and water. The organic layer was separated, washed successively with 10% aqueous citric acid, saturated aqueous sodium bicarbonate and brine, dried (MgSO$_4$), filtered and evaporated. The residue was purified on a silica gel flash chromatography column eluted with 50% EtOAc-hexane. Evaporation of the purified fractions and drying in vacuo afforded 0.433 g (79%) of the title compound.

$^1$H NMR (200 MHz, CDCl$_3$, ppm): δ1.25 (t, J=7.20 Hz, 3H), 3.79 (s, 6H), 4.10–4.30 (m, 2H), 4.59 (s, 2H), 5.57 (s, 1H), 5.94 (s, 2H), 6.52 (s, 2H), 6.71 (d, J=8.0 Hz, 1H), 6.96 (dd, J=1.60, 8.00 Hz, 1H), 7.14 (d, J=1.60 Hz, 1H).

FAB-MS: m/e 391 (M+1).

Step C: Preparation of 1-[4-(1-carboethoxy-1-(3,4-methylenedioxyphenyl)methoxy)-3,5-dimethoxyphenylmethyl]-3-carboethoxy-2-benzimidazolinone A solution of 0.070 g (0.27 mmol) of triphenylphosphine in 0.3 mL of THF was stirred under a nitrogen atmosphere at −30° C. and treated with 53 μL (0.27 mmol) of diisopropylazodicarboxylate. After stirring at this temperature for 45 minutes, a solution of 0.046 g (0.22 mmol) of 1-carboethoxy-2-benzimidazolinone and 0.103 g (0.27 mmol) of the product of step B dissolved in 0.7 mL THF was added via syringe. After the addition was complete the reaction was allowed to warm to room temperature, and then it was warmed further to 50° C. and stirred for 1 hour. The reaction mixture was then cooled again to room temperature and partitioned between ethyl acetate and water. The organic layer was separated, washed successively with 10% aqueous citric acid, saturated aqueous sodium bicarbonate and brine, dried (MgSO$_4$), filtered and evaporated. The residue was purified on a silica gel flash chromatography column eluted with 40% EtOAc-hexane. Evaporation of the purified fractions and drying in vacuo afforded 0.078 g (60%) of the title compound. Spectral analysis of the product indicated contamination with diisopropylhydrazodicarboxylate which had not been removed by chromatography. This mixture was used without further purification in the next step.

Step D: Preparation of 1-[4-(1-carboxy-1-(3,4-methylenedioxyphenyl)methoxy)-3,5-dimethoxyphenylmethyl ]-2-benzimidazolinone To a solution of 0.073 g (0.13 mmol) of the product of step C in 1 mL of ethanol was added 100 gL of a 5.0 N solution of sodium hydroxide and the reaction was stirred at room temperature for 1.5 hours. The reaction mixture was then adjusted to pH=5 with dropwise addition of 6 N hydrochloric acid, and then concentrated in vacuo. The residue was redissolved in methanol, filtered, and evaporated. The mixture was then purified on a silica gel flash chromatography column eluted with CHCl$_3$-MeOH-NH$_4$OH (80:15:1). Evaporation of the purified fractions and drying in vacuo afforded 0.023 g (38%) of the title compound.

$^1$H NMR (400 MHz, CD$_3$OD, ppm): δ3.66 (s, 6H), 4.95 (s, 2H), 5.46 (s, 1H), 5.85 (d, J=1.60 Hz, 1H), 5.86 (d, J=1.60 Hz, 1H), 6.54 9s, 2H), 6.60 (d, J=8.00 Hz, 1H), 6.78 (dd, J=1.60, 8.00 Hz, 1H), 6.95–7.06 (m, 5H).

FAB-MS: m/e 479 (M+1).

EXAMPLE 16

1-[4-(1-Carboxy-1-(5-methoxy-3,4-methylenedioxyphenyl)methoxy)-3,5-dipropylphenylmethyl]-3-ethyl-2-benzimidazolinone

Step A: Preparation of ethyl 2-bromo-2-(5-methoxy-3,4-methylenedioxyphenyl)acetate (General Method)

The 5-methoxy-3,4-methylenedioxybenzaldehyde is reacted overnight with trimethylsilyl cyanide in the presence of catalytic amounts of KCN and 18-crown-6 in methylene chloride. The reaction mixture is quenched with water and extracted with CH$_2$Cl$_2$/ethyl acetate/ether (1/2/2) mixture. The organic phase is washed with saturated aq. NaHCO$_3$ solution. After drying and concentration of the organic phase, the resulting trimethylsilyl cyanohydrin is hydrolyzed to give the corresponding hydroxy acid. Treatment with gaseous HCl in methanol or ethanol at 0° C. for 0.5 h and then overnight at room temperature affords the crude 2-hydroxy ester. The ester is then treated with triphenylphosphine and carbon tetrabromide in methylene chloride at 0° C. overnight. Methylene chloride is removed and flash column chromatography of the crude product using silica gel and ethyl acetate/hexane as eluent gives the title compound.

$^1$H NMR (200MHz, CDCl$_3$, ppm) δ6.76 (dd, 2H, J=1.6, 9.9 Hz); 5.99 (s, 2H); 5.25 (s, 2H); 4.29–4.20 (m, 2H); 3.91 (s, 3H); 1.30 (t, 3H, J=7.1 Hz).

FAB-MS m/e 318 (M+1).

Step B: Preparation of 1-[3,5-dipropyl-4-t-butyldimethylsilyloxy)phenylmethyl]-3-ethyl-2-benzimidazolinone To a solution of 5.0 g (1.0 eq, 30.9 mmol) of 1-ethyl-2-benzimidazolinone in 25 mL DMF was added 1.36 g (1.1 eq, 34.0 mmol) of 60% sodium hydride in mineral oil with stirring at room temperature under nitrogen. After stirring 15 minutes, 13.14 g ( 1.1 eq, 34.0 mmol) of 3,5-dipropyl-4-t-butyldimethylsilyloxybenzyl bromide was added. Stirring was continued for 16 hours then the reaction was partitioned between 400 mL ethyl ether and 400 mL H$_2$O. The organic layer was washed with saturated aqueous NaCl, dried over MgSO$_4$, filtered and concentrated in vacuo. The resultant oil was flash chromatographed with 1:3 ethyl acetate/hexane to yield 7.21 g (50%) of the title compound as a tan oil.

$^1$H NMR (400 MHz, CDCl$_3$, ppm) δ7.01 (m, 4H); 6.89 (s, 2H); 5.01 (s, 2H) 3.99 (q, 2H, J=7.3 Hz); 2.51 (t, 4H, J=7.5 Hz); 1.47 (sz, 4H, J=7.6 Hz); 1.34 (t, 3H, J=7.3 Hz); 0.87 (t, 6H, J=7.3 Hz).

FAB-MS m/e 466 (M+1).

Step C: Preparation of 1-[(3,5-di-n-propyl-4-hydroxy)phenylmethyl]-3-ethyl-2-benzimidazolone To a solution of 7.21 g (1.0 eq, 15.5 mmol) of the product from Step B in 30 mL THF under nitrogen at room temperature was added 31 mL (2.0 eq, 31.0 mmol) of 1 M tetrabutylammonium fluoride in THF. The mixture was stirred 16 hours at room temperature and the volatiles were removed in vacuo. The resultant oil was taken up in a minimum amount of methylene chloride and adsorbed onto the top of a two inch thick filter pad of silica gel. The product was then eluted through the silica gel with 1:2 ethyl acetate/hexane to yield 5.25 g (96%) of the title compound as a white solid.

$^1$H NMR (400 MHz, CDCl$_3$, ppm) δ7.02 (m, 4H) 6.96 (s, 2H); 4.95 (s, 2H); 4.68 (s, 1H); 3.98 (q, 2H, J=7.2 Hz); 2.52 (t, 4H, J=7.7 Hz); 1.59 (sx, 4H, J=7.5 (Hz); 1.36 (t, 3H, J=7.2 Hz); 0.94 (t, 6H, J=7.3 Hz).

FAB-MS m/e 353 (M+1).

Step D: Preparation of 1-[4-(1-carboethoxy-1-(5-methoxy-3,4-methylenedioxyphenyl)methoxy)-3,5-dipropylphenylmethyl]-3-ethyl-2-benzimidazolinone.

To a solution of 50 mg (1.0 eq, 0.14 mmol) of the product from Step C in 3 mL DMF under nitrogen at room temperature was added 92 mg (2.0 eq, 0.28 mmol) of cesium carbonate and 54 mg( 1.2 eq, 0.17 mmol) of the product from Step A. Stirring continued for 16 hours at room temperature. The reaction was partitioned between 100 mL ethyl ether and 100 mL H$_2$O and the organic layer was washed with saturated aqueous NaCl, dried over MgSO$_4$, filtered and concentrated in vacuo. The resultant oil was flash chromatographed with 1:2 ethyl acetate/hexane. The product-containing fractions were combined and concentrated in vacuo to yield the title compound as a clear oil.

$^1$H NMR (400 MHz, CDCl$_3$, ppm) δ7.02 (m,. 3H); 6.92 (s, 2H); 6.85 (m, 1H); 6.65 (d, 1H, J=1.4 Hz); 6.64 (d, 1H, J=1.4 Hz); 5.96 (ab-quartet, 2H, J=1.4 Hz); 4.93 (s, 2H); 4.89 (s, 1H); 4.20 (m, 2H); 3.97 (q, 2H, J=7.2 Hz); 3.83 (s, 3H); 2.32 (m, 4H); 1.43 (m, 4H); 1.34 (t, 3H, J=7.2 Hz); 1.20 (t, 3H, J=7.1 Hz); 0.78 (t, 6H, J=7.3 Hz).

FAB-MS m/e 589 (M+1).

Step E: Preparation of 1-[4-(1-carboxy-1-(5-methoxy-3,4-methylenedioxyphenyl)methoxy)-3,5-dipropylphenylmethyl]-3-ethyl-2-benzimidazolinone.

The product from Step D was taken up in 10 mL of methanol and 4 mL 5N NaOH(aq) was added with stirring at room temperature. The reaction was stirred for 3 hours and the volatiles removed in vacuo. The resultant slurry was diluted with 50 mL H$_2$O and acidified with 1N HCl (aq) and extracted with 3×20 mL ethyl acetate. The combined organics were concentrated in vacuo. Trituration of the resultant oil with ethyl ether gave 64 mg (82%-2 steps) of the title compound as a white solid.

$^1$H NMR (400MHz, CD$_3$OD, ppm) δ7.18 (m, 1H); 7.12 (m, 1H); 7.04 (m, 2H); 6.95 (s, 2H); 6.63 (s, 2H); 5.94 (s, 2H); 5.00 (s, 2H); 4.93 (s, 1H); 4.00 (q, 2H, J=7.2 Hz); 3.79 (s, 3H); 2.33 (t, 4H, J=8.0 Hz); 1.42 (m, 4H); 1.32 (t, 3H, J=7.2 Hz); 0.78 (t, 6H, J=7.3 Hz).

FAB-MS m/e 561 (M+1).

EXAMPLE 17

1-[4-(1-Carboxy-1-(3,5-dithiomethylphenyl)methoxy)-3,5-dipropylphenylmethyl]-3-ethyl-2-benzimidazolinone Step A: Preparation of ethyl 2-bromo-2-(3,5-dithiomethylphenyl)acetate The title compound was synthesized in a similar manner to that outlined for Example 16 (Step A) replacing 5-methoxy-3,4-methylenedioxybenzaldehyde by 3,5-dithiomethylbenzaldehyde.

$^1$H NMR (400 MHz, CDCl$_3$, ppm): δ7.13 (d, 2H, J=1.7 Hz); 7.04 (t, 1H, J=1.7 Hz); 5.21 (s, 1H); 4.22 (m, 2H); 2.47 (s, 6H); 1.27 (t, 3H, J=7.1 Hz).

FAB-MS: m/e 336 (M+1).

Step B: Preparation of 1-[4-(1-carboxy-1-(3,5-dithiomethylphenyl)methoxy)-3,5-dipropylphenylmethyl]-3-ethyl-2-benzimidazolinone The title compound was synthesized in a similar manner to that outlined for Example 16 (Steps B-E).

$^1$H NMR (400 MHz, CD$_3$OD, ppm) a 7.16 (m, 1H); 7.10-7.02 (m, 6H); 6.96 (s, 2H); 5.00 (s, 1H); 4.99 (s, 2H); 3.99 (q, 2H, J=7.3 Hz); 2.41 (s, 6H); 2.32 (t, 4H, J=8.0 Hz); 1.42 (m, 4H); 1.31 (t, 3H, J=7.2 Hz); 0.77 (t, 6H, J=7.3 Hz).

FAB-MS m/e 580 (M+1).

EXAMPLE 18

1-[4-(1-Carboxy-1-(5-bromo-3,4-methylenedioxyphenyl)methoxy)-3,5-dipropylphenylmethyl]-3-ethyl-2-benzimidazolinone Step A: Preparation of ethyl 2-bromo-2-(5-bromo-3,4-3-methylenedioxyphenyl)acetate The title compound was synthesized in a similar manner to that outlined for Example 16 (Step A) replacing 5-methoxy-3,4-methylenedioxybenzaldehyde by 5-bromo-3,4-methylenedioxybenzaldehyde.

$^1$H NMR (200 MHz, CDCl$_3$, ppm) δ7.12 (d, 1H, J=1.5 Hz); 7.07 (d, 1H, J=1.5 Hz); 6.06 (s, 2H); 5.21 (s, 1H); 4.25 (m, 2H); 1.30 (t, 3H, J=7.1 Hz).

FAB-MS m/e 345 (M+1).

Step B: Preparation of 1-[4-(1-carboxy-1-(5-bromo-3,4-methylenedioxyphenyl)methoxy)-3,5-dipropylphenylmethyl]-3-ethyl-2-benzimidazolinone The title compound was synthesized in a similar manner to that outlined for Example 16 (Steps B-E).

$^1$H NMR (400 MHz, CD$_3$OD, ppm) δ7.17 (m, 1H); 7.11 (dt, 1H, J=2.0, 7.4 Hz); 7.04 (m, 3H); 6.96 (s, 2H); 6.93 (d, 1H, J=1.5 Hz); 6.05 (s, 2H); 5.00 (s, 2H); 4.95 (s, 1H); 4.00 (q, 2H, J=7.2 Hz); 2.41 (s, 6H); 2.34 (t, 4H, J=7.7 Hz); 1.42 (m, 4H); 1.32 (t, 3H, J=7.2 Hz); 0.79 (t, 6H, J=7.3 Hz).

FAB-MS m/e 611 (M+1).

EXAMPLE 19

1-[4-(1-Carboxy-1-(1'-methyl-3,4-methylenedioxyphenyl)methoxy)-3,5-dipropylphenylmethyl]-3-ethyl-2-benzimidazolinone Step A: Preparation of methyl 2-bromo-2-(1'-methyl-3,4-methylenedioxyphenyl)acetate (General Method)

1,4-Methyl-3,4-methylenedioxyphenylacetic acid is converted to the corresponding methyl ester by refluxing the acid in methanol in the presence of a catalytic amount of conc. sulfuric acid. The ester thus obtained is then refluxed in carbon tetrachloride with N-bromosuccinimide (1.1 equiv) and AIBN (0.05-0.1 equiv). Upon completion of the reaction, the resulting product is purified by flash column chromatography using silica gel and ethyl acetate in hexane as eluent to provide the title bromide.

$^1$H NMR (400MHz, CDCl$_3$, ppm): δ7.04 (d, 1H, J=1.8 Hz); 6.90 (dd, 1H, J=1.9, 8.0 Hz); 6.66 (d, 1H, J=8.0 Hz); 6.27 (m, 1H); 5.28 (s, 1H); 3.77 (d, 3H, J=1.0 Hz); 1.66 (dd, 3H, J=1.1, 5.0 Hz).

FAB-MS m/e 288 (M+1).

Step B: Preparation of 1-[4-(1-Carboxy-1-(1'-methyl-3,4methylenedioxyphenyl)methoxy)-3,5-dipropylphenylmethyl]-3-ethyl-2-benzimidazolinone The title compound was synthesized in a similar manner to that outlined for Example 16 (Steps B-E).

$^1$H NMR (400 MHz, CD$_3$OD, ppm) δ7.17 (d, 1H, J=7.4 Hz); 7.10 (dt, 1H, J=1.7, 7.2 Hz); 7.03 (m, 2H) 6.94 (s, 2H); 6.91 (dd, 1 H, J=1.6, 4.9 Hz); 6.79 (m, 1H); 6.70 (dd, 1H, J=2.6, 7.9 Hz); 6.27 (q, 1H, J=5.8 Hz); 4.99 (s, 2H); 4.93 (d, 1H, J=1.5 Hz); 3.99 (q, 2H, J=7.2 Hz); 2.32 (m, 4H); 1.61 (d, 3H, J=4.9 Hz); 1.41 (m, 4H); 1.32 (t, 3H, J=7.2 Hz); 0.77 (t, 6H, J=7.4 Hz).

FAB-MS m/e 562 (M+1).

EXAMPLE 20

1-[4-(1-Carboxy-1-(3,5-dimethoxyphenyl)methoxy)-3,5-dipropylphenylmethyl]-3-ethyl-2-benzimidazolinone The title compound was synthesized in a similar manner to that outlined for Example 16 except that in Step A 5-methoxy-3,4-methylenedioxybenzaldehyde was replaced by 3,5-dimethoxybenzaldehyde.

$^1$H NMR (400 MHz, CD$_3$OD, ppm) δ7.60-7.52 (m, 2H), 7.10-7.00 (m, 2H), 7.00-6.85 (m, 2H), 6.60-6.52 (br, s, 2H), 6.35 (br, s, 1H), 5.34 (s, 1H), 4.94 (s, 2H), 3.96 (q, 2H), 3.67 (s,6H), 2.27 (t, 4H), 1.60-1.12 (m, 4H), 1.32 (t, 3H), 0.73 (t, 6H).

What is claimed is:

1. A compound of structural Formula I:

[Structure I: benzimidazolinone with R$^{16}$, R$^{17}$, R$^{18}$, R$^{12}$ substituents, =O, CH$_2$ linker to phenyl ring with R$^9$, R$^{10}$, then X, Z, R$^8$ to phenyl with R$^{3b}$, R$^1$, R$^{3a}$, R$^2$]

or a pharmaceutically acceptable salt thereof, wherein:

R$^1$, R$^2$, R$^{3a}$ and R$^{3b}$ are independently:
- (a) H,
- (b) F, Cl, Br, or I,
- (c) —NO$_2$,
- (d) —NH$_2$,
- (e) —NH(C$_1$-C$_4$)-alkyl,
- (f) —N[(C$_1$-C$_4$)-alkyl]$_2$,
- (g) —SO$_2$NHR$^7$,
- (h) —CF$_3$,
- (i) (C$_1$-C$_4$)-alkyl,
- (j) —OR$^7$,
- (k) —S(O)$_n$—(C$_1$-C$_4$)-alkyl,
- (l) —NHCO—(C$_1$-C$_4$)-alkyl,
- (m) —NHCO—O(C$_1$-C$_4$)-alkyl,
- (n) —CH$_2$O—(C$_1$-C$_4$)-alkyl,
- (o) —O—(CH$_2$)$_m$—OR$^7$,
- (p) —CONR$^7$R$^{11}$, or
- (q) —COOR$^7$;

n is 0, 1 or 2;

m is 2, 3 or 4;

R$^1$ and R$^2$ on adjacent carbon atoms can be joined together to form a ting structure:

[Ring structure with A]

A represents:
- a) —Y—C(R$^4$)=C(R$^5$)—,
- b) —Y—[C(R$^6$)(R$^6$)]$_s$—Y—,
- c) —Y—C(R$^6$)(R$^6$)—C(R$^6$)(R$^6$)—,
- d) —C(R$^4$)=C(R$^5$)—Y—,
- e) —C(R$^6$)(R$^6$)—C(R$^6$)(R$^6$)—Y—, or
- f) —C(R$^4$)=C(R$^5$)—C(R$^4$)=C(R$^5$)—;

s is 1 or 2;

Y is —O— and —S(O)n;

R$^4$ and R$^5$ are independently:
- (a) H,
- (b) (C$_1$-C$_6$)-alkyl or (C$_2$-C$_6$)-alkenyl each of which is unsubstituted or substituted with one or two substituents selected from the group consisting of:
  - (i) —OH,
  - (ii) —O—(C$_1$-C$_4$)-alkyl,
  - (iii) —S(O)$_n$—(C$_1$-C$_4$)-alkyl,
  - (iv) —NR$^7$—(C$_1$-C$_4$)-alkyl,
  - (v) —NHR$^7$,
  - (vi) —COOR$^7$,
  - (vii) —CONHR$^7$,
  - (viii) —OCOR$^{11}$, or
  - (ix) —CONR$^7$R$^{11}$,
- (c) (C$_3$-C$_7$)-cycloalkyl,
- (d) F, Cl, Br, I,
- (e) CF$_3$,
- (f) —COOR$^7$,
- (g) —CONR$^7$R$^{11}$,
- (h) —NR$^7$R$^{11}$,
- (i) —NR$^7$CONR$^7$R$^{11}$,
- (j) —NR$^7$COOR$^{11}$,
- (k) —SO$_2$NR$^7$R$^{11}$,
- (l) —O—(C$_1$-C$_4$)-alkyl,
- (m) —S(O)$_n$—(C$_1$-C$_4$)-alkyl, or
- (n) —NHSO$_2$R$^{11}$;

R$^6$ is:
- (a) H,
- (b) (C$_1$-C$_4$)-alkyl unsubstituted or substituted with one of the following substituents:
  - (i) —OH,
  - (ii) —NR$^7$R$^{11}$,
  - (iii) —COOR$^7$,
  - (iv) —CONHR$^7$, or
  - (v) —CONR$^7$R$^{11}$, or
- (c) F;

R$^7$ is:

(a) H,
(b) $(C_1-C_6)$-alkyl,
(c) phenyl,
(d) benzyl, or
(e) $(C_3-C_7)$-cycloalkyl;

$R^8$ is:
(a) H,
(b) $(C_1-C_6)$-alkyl, unsubstituted or substituted with a substituent selected from the group consisting of:
  (i) —phenyl,
  (ii) —$(C_3-C_7)$-cycloalkyl,
  (iii) —$NR^7R^{11}$,
  (iv) —OH,
  (v) —$CO_2R^7$, or
  (vi) —$CON(R^7)_2$,
(c) phenyl, unsubstituted or substituted with a substituent selected from the group consisting of:
  (i) $(C_1-C_4)$-alkyl,
  (ii) —O—$(C_1-C_4)$-alkyl,
  (iii) —$CONR^7R^{11}$,
  (iv) F, Cl, Br or I, or
  (v) —$COOR^7$;

$R^9$ and $R^{10}$ are independently:
(a) H,
(b) $(C_1-C_6)$-alkyl, unsubstituted or substituted with $(C_3-C_7)$-cycloalkyl,
(c) $(C_2-C_6)$-alkenyl,
(d) $(C_2-C_6)$-alkynyl,
(e) Cl, Br, F, I,
(f) $(C_1-C_6)$-alkoxy,
(g) when $R^9$ and $R^{10}$ are on adjacent carbons, they can be joined to form a phenyl ring,
(h) perfluoro-$(C_1-C_6)$-alkyl,
(i) $(C_3-C_7)$-cycloalkyl, unsubstituted or substituted with $(C_1-C_6)$-alkyl,
(j) phenyl,
(k) $(C_1-C_6)$-alkyl-$S(O)_n$—$(CH_2)_n$—,
(l) hydroxy-$(C_1-C_6)$-alkyl,
(m) —$CF_3$,
(n) —$CO_2R^7$,
(o) —OH,
(p) —$NR^7R^{11}$,
(q) —[$(C_1-C_6)$-alkyl]$NR^7R^{11}$,
(r) —$NO_2$,
(s) —$(CH_2)_n$—$SO_2$—$N(R^7)_2$,
(t) —$NR^7CO$—$(C_1-C_4)$-alkyl, or
(u) —$CON(R^7)_2$;

$R^{11}$ is:
(a) $(C_1-C_6)$-alkyl,
(b) phenyl,
(c) —$(C_1-C_4)$-alkyl-phenyl, or
(d) $(C_3-C_7)$-cycloalkyl;

$R^{12}$ is:
(a) H,
(b) $(C_1-C_6)$-alkyl, unsubstituted or substituted with one or two substituents selected from the group consisting of:
  i) —OH,
  ii) —O—$(C_1-C_4)$-alkyl,
  iii) —O—$(C_1-C_4)$-cycloalkyl,
  iv) —$S(O)_n$—$(C_1-C_4)$-alkyl,
  v) —$NR^7$—$(C_1-C_4)$-alkyl,
  vi) —$NR^7R^{11}$,
  vii) —$COOR^7$,
  viii) —$CONHR^7$,
  ix) —$OCOR^{11}$,
  x) —$CONR^7R^{11}$,
  xi) —$NR^7CONR^7R^{11}$,
  xii) —$NR^7COOR^{11}$,
  xiii) —$C(R^6)(OH)$—$C(R^6)(R^7)(OH)$, or
  xiv) —$SO_2NR^7R^{11}$,
(c) $(C_3-C_7)$-cycloalkyl,
(d) $(C_1-C_4)$-perfluoroalkyl,
(e) aryl, unsubstituted or substituted with one to three substituents selected from the group consisting of:
  i) F, Cl, Br, I,
  ii) $(C_1-C_6)$-alkyl,
  iii) $(C_1-C_6)$-alkoxy,
  iv) hydroxy-$(C_1-C_6)$-alkyl,
  v) —$CF_3$,
  vi) —$COOR^7$,
  vii) —OH,
  viii) —$NR^7R^{11}$,
  ix) —$NH_2$,
  x) —$NO_2$,
  xi) —$CONR^7R^{11}$,
  xii) two adjacent groups may be joined together to form a methylenedioxy group,
(f) aryl$(C_1-C_2)$alkyl unsubstituted or substituted with one to three substituents selected from the group consisting of:
  i) F, Cl, Br, I,
  ii) $(C_1-C_6)$-alkyl,
  iii) $(C_1-C_6)$-alkoxy,
  iv) hydroxy-$(C_1-C_6)$-alkyl,
  v) —$CF_3$,
  vi) —$COOR^7$,
  vii) —OH,
  viii) —$NR^7R^{11}$,
  ix) —$NH_2$,
  x) —$NO_2$,
  xi) —$CONR^7R^{11}$m or
  xii) two adjacent groups may be joined together to form a methylenedioxy group;

X is:
(a)
(b) —$S(O)_n$—,
(c) —$NR^7$—,
(d) —$CH_2O$—,
(e) —$CH_2S(O)_n$—,
(f) —$CH_2NR^7$—,
(g) —$OCH_2$—,
(h) —$N(R^7)CH_2$—,
(i) —$S(O)_nCH_2$—,
(j) —single bond, or
(k) —$C(R^9)_2$—;

Z is:
(a) —$CO_2H$,
(b) —$CO_2R^{13}$,
(c) —$CONHSO_2$-phenyl, wherein phenyl is unsubstituted or substituted with one or two substituents selected from the group consisting of:
  i) $(C_1-C_4)$-alkyl,
  ii) —O—$(C_1-C_4)$-alkyl,
  iii) —$CONR^7R^{11}$,
  iv) F, Cl, Br or I,
  v) —$COOR^7$,
  vi) $(C_1-C_4)$-perfluoroalkyl,
  vii) $(C_3-C_7)$-cycloalkyl,
  viii) $NR^7R^{11}$,
  ix) $SO_2NR^7R^{11}$,
  x) hydroxy, or
  xi) 2,3-, or 3,4-methylenedioxy;

(d) —CONHSO$_2$—(C$_1$–C$_8$)-alkyl, wherein the alkyl group is unsubstituted or substituted as defined in R$^4$(b),
(e) —CONHSO$_2$—(C$_1$–C$_4$)-perfluoroalkyl,
(f) —CONHSO$_2$—(C$_3$–C$_7$)-cycloalkyl,
(g) —SO$_2$NHCO-phenyl, wherein phenyl is as defined in Z(d) above,
(h) —SO$_2$NHCO—(C$_1$–C$_8$)-alkyl, wherein the alkyl group is unsubstituted or substituted as defined in R$^4$(b),
(i) —SO$_2$NHCO—(C$_1$–C$_4$)-perfluoroalkyl,
(j) —SO$_2$NHCON(R$^{11}$)$_2$ wherein the R$^{11}$ groups are the same or different,
(k) —PO(OR$^7$)$_2$, wherein the R$^7$ groups are the same or different, or
(l) —PO(R$^{11}$)OR$^7$;

R$^{13}$ is:
(a) (C$_1$–C$_4$)-alkyl,
(b) CHR$^{14}$—O—COR$^{15}$,
(c) CH$_2$CH$_2$—N[(C$_1$–C$_2$)-alkyl]$_2$m
(d) (CH$_2$CH$_2$O)y—O—[(C$_1$–C$_4$)-alkyl], wherein y is 1 or 2,
(e) phenyl, naphthyl, CH$_2$-phenyl or CH$_2$-naphthyl, where phenyl or naphthyl is substituted or unsubstituted with CO$_2$—(C$_1$–C$_4$)-alkyl,

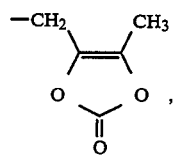 (f)

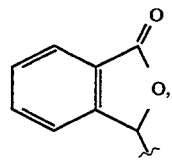 (g)

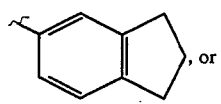 (h) , or

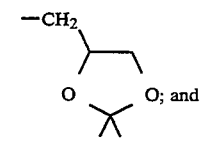 (i) ; and

R$^{14}$ and R$^{15}$ independently are (C$_1$–C$_6$)-alkyl or phenyl,

R$^{16}$, R$^{17}$ and R$^{18}$ are independently:
(a) H,
(b) (C$_1$–C$_6$)-alkyl, unsubstituted or substituted with one or two substituents selected from the group consisting of:
   i) —OH,
   ii) —O—(C$_1$–C$_4$)-alkyl,
   iii) —NR$^7$R$^{11}$,
   iv) —COOR$^7$,
   v) —CONR$^7$R$^{11}$,
   vi) —SO$_2$NR$^7$R$^{11}$,
   vii) —NH$_2$,
   viii) —NO$_2$,
(c) (C$_3$–C$_7$)-cycloalkyl,
(d) (C$_1$–C$_4$)-perfluoroalkyl,
(e) F, Cl, Br, I,
(f) —OH,
(g) (C$_1$–C$_4$)-alkoxy,
(h) —COOR$^7$,
(i) —CONR$^7$R$^{11}$,
(j) —CONHSO$_2$—(C$_1$–C$_6$)-alkyl wherein the alkyl group is unsubstituted or substituted as defined in R$^4$(b),
(k) —CONHSO$_2$-phenyl wherein the phenyl group is unsubstituted or substituted as defined in Z(d),
(l) —NR$^7$R$^{11}$m
(m) —NH$_2$,
(n) —NO$_2$,
(o) —NR$^7$COR$^{11}$,
(p) —NR$^7$COOR$^{11}$,
(q) —NR$^7$CONR$^7$R$^{11}$,
(r) two adjacent groups may be joined together to form a methylenedioxy group,
(s) —SO$_2$NR$^7$R$^{11}$,
(t) —SO$_2$NHCO—(C$_1$–C$_6$)-alkyl wherein the alkyl group is unsubstituted or substituted as defined in R$^4$(b),
(u) —SO$_2$NHCO-phenyl wherein the phenyl group is unsubstituted or substituted as defined in Z(d).

2. The compound as recited in claim 1 of structural Formula II:

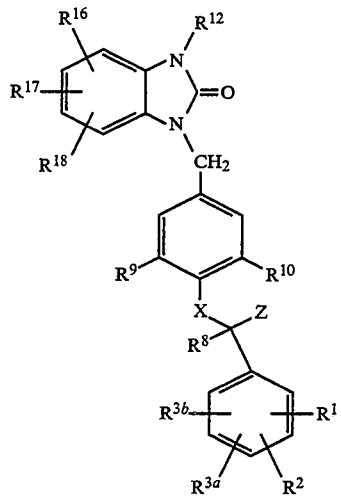 II or a pharmaceutically acceptable salt thereof, wherein:
R$^1$, R$^2$, R$^{3a}$ and R$^{3b}$ are independently:
(a) H,
(b) F, Cl, Br, or I,
(c) —NO$_2$,
(d) —NH$_2$,
(e) —NH(C$_1$–C$_4$)-alkyl,
(f) —N[(C$_1$–C$_4$)-alkyl]$_2$m
(g) —SO$_2$NHR$^7$,
(h) —CF$_3$,
(i) (C$_1$–C$_4$)-alkyl,
(j) —OR$^7$,
(k) —S(O)$_n$—(C$_1$–C$_4$)-alkyl,
(l) —NHCO—(C$_1$–C$_4$)-alkyl,
(m) —NH CO—O(C$_1$–C$_4$)-alkyl,
(n) —CH$_2$O—(C$_1$–C$_4$)-alkyl,
(o) —O—(CH$_2$)$_m$—OR$^7$,
(p) —CONR$^7$R$^{11}$, or
(q) —COOR$^7$;

m is 2, 3 or 4, n is 0, 1 or 2,

R$^1$ and R$^2$ on adjacent carbon atoms can be joined together to form a ring structure:

A represents
- a) —Y—C(R$^4$)=C(R$^5$)—,
- b) —Y—[C(R$^6$)(R$^6$)]$_s$—Y—,
- c) —Y—C(R$^6$)(R$^6$)—C(R$^6$)(R$^6$)—,
- d) —C(R$^4$)=C(R$^5$)—Y—,
- e) —C(R$^6$)(R$^6$)—C(R$^6$)(R$^6$)—Y—, or
- f) —C(R$^4$)=C(R$^5$)—C(R$^4$)=C(R$^5$)—;

s is 1 or 2;

Y is —O— and —S(O)$_n$—;

R$^4$ and R$^5$ are independently:
- (a) H,
- (b) (C$_1$–C$_6$)-alkyl or (C$_2$–C$_6$)-alkenyl each of which is unsubstituted or substituted with one or two substituents selected from the group consisting of:
  - (i) —OH,
  - (ii) —O—(C$_1$–C$_4$)-alkyl,
  - (iii) —S(O)$_n$—(C$_1$–C$_4$)-alkyl,
  - (iv) —NR$^7$—(C$_1$–C$_4$)-alkyl,
  - (v) —NHR$^7$,
  - (vi) —COOR$^7$,
  - (vii) —CONHR$^7$,
  - (viii) —OCOR$^{11}$, or
  - (ix) —CONR$^7$R$^{11}$,
- (c) (C$_3$–C$_7$)-cycloalkyl,
- (d) F, Cl, Br, I,
- (e) CF$_3$,
- (f) —COOR$^7$m
- (g) —CONR$^7$R$^{11}$,
- (h) —NR$^7$R$^{11}$,
- (i) —NR$^7$CONR$^7$R$^{11}$,
- (j) —NR$^7$COOR$^{11}$,
- (k) —SO$_2$NR$^7$R$^{11}$,
- (l) —O—(C$_1$–C$_4$)-alkyl,
- (m) —S(O)$_n$—(C$_1$–C$_4$)-alkyl, or
- (n) —NHSO$_2$R$^{11}$;

R$^6$ is:
- (a) H,
- (b) (C$_1$–C$_4$)-alkyl unsubstituted or substituted with one or two substituents selected from the group consisting of:
  - (i) —OH,
  - (ii) —NR$^7$R$^{11}$,
  - (iii) —COOR$^7$,
  - (iv) —CONHR$^7$, or
  - (v) —CONR$^7$R$^{11}$, or
- (c) F;

R$^7$ is:
- (a) H,
- (b) (C$_1$–C$_6$)-alkyl,
- (c) phenyl,
- (d) benzyl, or
- (e) (C$_3$–C$_7$)-cycloalkyl;

R$^8$ is:
- (a) H,
- (b) (C$_1$–C$_6$)-alkyl, unsubstituted or substituted with one or two substituents selected from the group consisting of:
  - (i) —phenyl,
  - (ii) —(C$_3$–C$_7$)-cycloalkyl,
  - (iii) —NR$^7$R$^{11}$,
  - (iv) —OH,
  - (v) —CO$_2$R$^7$, or
  - (vi) —CON(R$^7$)$_2$, or
- (c) phenyl;

R$^9$ and R$^{10}$ are independently:
- (a) H,
- (b) (C$_1$–C$_6$)-alkyl, unsubstituted or substituted with (C$_3$–C$_7$)-cycloalkyl,
- (c) (C$_2$–C$_6$)-alkenyl,
- (d) (C$_2$–C$_6$)-alkynyl,
- (e) Cl, Br, F, I,
- (f) (C$_1$–C$_6$)-alkoxy,
- (g) when R$^9$ and R$^{10}$ are on adjacent carbons, they can be joined to form a phenyl ting,
- (h) perfluoro—(C$_1$–C$_6$)-alkyl,
- (i) (C$_3$–C$_7$)-cycloalkyl, unsubstituted or substituted with (C$_1$–C$_6$)-alkyl,
- (j) phenyl,
- (k) (C$_1$–C$_6$)—alkyl—S(O)$_n$—(CH$_2$)$_n$—,
- (l) hydroxy—(C$_1$–C$_6$)-alkyl,
- (m) —CF$_3$,
- (n) —CO$_2$R$^7$,
- (o) —OH,
- (p) —NR$^7$R$^{11}$,
- (q) —[(C$_1$–C$_6$)-alkyl]NR$^7$R$^{11}$,
- (r) —NO$_2$,
- (s) —(CH$_2$)$_n$—SO$_2$—N(R$^7$)$_2$,
- (t) —NR$_7$ CO—(C$_1$–C$_4$)-alkyl, or
- (u) —CON(R$^7$)$_2$;

R$^{11}$ is:
- (a) (C$_1$–C$_6$)-alkyl,
- (b) phenyl,
- (c) —(C$_1$–C$_4$)-alkyl-phenyl, or
- (d) (C$_3$–C$_7$)-cycloalkyl;

R$^{12}$ is:
- (a) H,
- (b) (C$_1$–C$_6$)-alkyl, unsubstituted or substituted with one or two substituents selected from the group consisting of:
  - (i) —OH,
  - (ii) —O—(C$_1$–C$_4$)-alkyl,
  - (iii) —O—(C$_1$–C$_4$)-cycloalkyl,
  - (iv) —S(O)$_n$—(C$_1$–C$_4$)-alkyl,
  - (v) —NR$^7$—(C$_1$–C$_4$)-alkyl,
  - (vi) —NR$^7$R$^{11}$,
  - (vii) —COOR$^7$,
  - (viii) —CONHR$^7$,
  - (ix) —OCOR$^{11}$,
  - (x) —CONR$^7$R$^{11}$,
  - (xi) —NR$^7$CONR$^7$R$^{11}$,
  - (xii) —NR$^7$COOR$^{11}$,
  - (xiii) —C(R$^6$)(OH)—C(R$^6$)(R$^7$)(OH), or
  - (xiv) —SO$_2$NR$^7$R$^{11}$,
- (c) (C$_3$–C$_7$)-cycloalkyl,
- (d) (C$_1$–C$_4$)-perfluoroalkyl,
- (e) aryl, unsubstituted or substituted with one to three substituents selected from the group consisting of:
  - (i) F, Cl, Br, I,
  - (ii) (C$_1$–C$_6$)-alkyl,
  - (iii) (C$_1$–C$_6$)-alkoxy,
  - (iv) hydroxy—(C$_1$–C$_6$)-alkyl, (v) —CF$_3$,
(vi) —COOR$_7$,
(vii) —OH,
(viii) —NR$^7$R$^{11}$,
(ix) —NH$_2$,
(x) —NO$_2$,
(xi) —CONR$^7$R$^{11}$,
(xii) two adjacent groups may be joined together to form a methylenedioxy group,
(f) aryl—(C$_1$-C$_2$)-alkyl unsubstituted or substituted with one to three substituents selected from the group consisting of:
(i) F, Cl, Br, I,
(ii) (C$_1$-C$_6$)-alkyl,
(iii) (C$_1$-C$_6$)-alkoxy,
(iv) hydroxy—(C$_1$-C$_6$)-alkyl,
(v) —CF$_3$,
(vi) —COOR$^7$,
(vii) —OH,
(viii) —NR$^7$R$^{11}$,
(ix) —NH$_2$,
(x) —NO$_2$,
(xi) —CONR$^7$R$^{11}$, or
(xii) two adjacent groups may be joined together to form a methylenedioxy group;

X is:
(a) —O—,
(b) —S(O)$_n$—,
(c) —NR$^7$—,
(d) —CH$_2$O—,
(e) —CH$_2$S(O)$_n$—,
(f) —CH$_2$NR$^7$—,
(g) —OCH$_2$—,
(h) —N(R$^7$)CH$_2$—,
(i) —S(O)$_n$CH$_2$—,
(j) —single bond, or
(k) —C(R$^9$)$_2$—;

Z is:
(a) —CO$_2$H.
(b) —CO$_2$R$^{13}$,
(c) —CONHSO$_2$—phenyl, wherein phenyl is unsubstituted or substituted with one or two substituents selected from the group consisting of:
i) (C$_1$-C$_4$)-alkyl,
ii) —O—(C$_1$-C$_4$)-alkyl,
iii) —CONR$^7$R$^{11}$,
iv) F, Cl, Br or I,
v) —COOR$^7$,
vi) (C$_1$-C$_4$)-perfluoroalkyl,
vii) (C$_3$-C$_7$)-cycloalkyl,
viii) NR$^7$R$^{11}$,
ix) SO$_2$NR$^7$R$^{11}$,
x) hydroxy, or
xi) 2,3-, or 3,4-methylenedioxy.
(d) —CONHSO$_2$—(C$_1$-C$_8$)-alkyl, wherein the alkyl group is unsubstituted or substituted as defined in R$^4$(b),
(e) —CONHSO$_2$—(C$_1$-C$_4$)-perfluoroalkyl,
(f) —CONHSO$_2$—(C$_3$-C$_7$)-cycloalkyl,
(g) —SO$_2$NHCO-phenyl, wherein phenyl is as defined in Z(d) above,
(h) —SO$_2$NHCO—(C$_1$-C$_8$)-alkyl, wherein the alkyl group is unsubstituted or substituted as defined in R$^4$(b),
(i) —SO$_2$NHCO—(C$_1$-C$_4$)-perfluoroalkyl,
(j) —SO$_2$NHCON(R$^{11}$)$_2$ wherein the R$^{11}$ groups are the same or different,
(k) —PO(OR$^7$)$_2$, wherein the R$^7$ groups are the same or different, or
(l) —PO(R$^{11}$)OR$^7$;

R$^{13}$ is:
(a) (C$_1$-C$_4$)-alkyl,
(b) CHR$^{14}$—O—COR$^{15}$,
(c) CH$_2$CH$_2$—N[(C$_1$-C$_2$)-alkyl]$_2$,
(d) (CH$_2$CH$_2$O)$_y$—O—[(C$_1$-C$_4$)-alkyl], wherein y is 1 or 2, (e) phenyl, naphthyl, CH$_2$-phenyl or CH$_2$-naphthyl, where phenyl or naphthyl is substituted or unsubstituted with CO$_2$—(C$_1$-C$_4$)-alkyl,

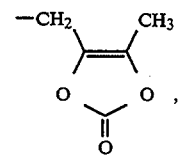 (f)

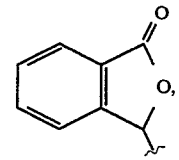 (g)

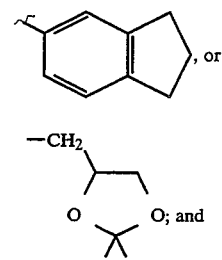 (h)

—CH$_2$ (i)

O O; and

R$^{14}$ and R$^{15}$ independently are (C$_1$-C$_6$)-alkyl or phenyl,
R$^{16}$, R$^{17}$ and R$^{18}$ are independently:
(a) H,
(b) (C$_1$-C$_6$)-alkyl, unsubstituted or substituted with one or two substituents selected from the group consisting of:
(i) —OH,
(ii) —O—(C$_1$-C$_4$)-alkyl,
(iii) —NR$^1$R$^{11}$,
(iv) —COOR$^7$,
(v) —CONR$^7$R$^{11}$,
(vi) —SO$_2$NR$^7$R$^{11}$,
(vii) —NH$_2$,
(viii) —NO$_2$,
(c) (C$_3$-C$_7$)-cycloalkyl,
(d) (C$_1$-C$_4$)-perfluoroalkyl,
(e) F, Cl, Br, I,
(f) —OH,
(g) (C$_1$-C$_4$)-alkoxy,
(h) —COOR$^7$,
(i) —CONR$^7$R$^{11}$,
(j) —CONHSO$_2$—(C$_1$-C$_6$)-alkyl wherein the alkyl group is unsubstituted or substituted as defined in R$^4$(b),
(k) —CONHSO$_2$-phenyl wherein the phenyl group is unsubstituted or substituted as defined in Z(d),
(l) —NR$^7$R$^{11}$,
(m) —NH$_2$,
(n) —NO$_2$, (o) —NR⁷COR¹¹,
(p) —NR⁷COOR¹¹,
(q) —NR⁷COR⁷R¹¹,
(r) two adjacent groups may be joined together to form a methylenedioxy group,
(s) —SO₂NR⁷R¹¹,
(t) —SO₂NHCO—(C₁-C₆)-alkyl wherein the alkyl group is unsubstituted or substituted as defined in R⁴(b),
(u) —SO₂NHCO-phenyl wherein the phenyl group is unsubstituted or substituted as defined in Z(d).

3. The compound as recited in claim 1 of structural Formula III:

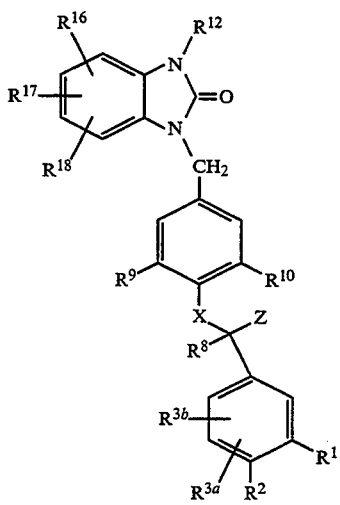

or a pharmaceutically acceptable salt thereof, wherein:
R¹, R², R³a and R³b are independently:
(a) H,
(b) F, Cl, Br, or I,
(c) —NO₂,
(d) (C₁-C₄)-alkyl,
(e) —OR⁷,
(f) —NHCO—(C₁-C₄)-alkyl,
(g) —NHCO—O(C₁-C₄)-alkyl,
(h) —O—(CH₂)$_m$—OR⁷,
(i) —CONR⁷R¹¹, or
(j) —COOR⁷;
m is 2, 3 or 4,
R¹ and R² on adjacent carbon atoms can be joined together to form a ring structure:

A represents:
(a) —Y—C(R⁴)=C(R⁵)—,
(b) —Y—[C(R⁶)(R⁶)]$_s$—Y—,
(c) —Y—C(R⁶)(R⁶)—C(R⁶)(R⁶)—,
(d) —C(R⁴)=C(R⁵)—Y—,
(e) —C(R⁶)(R⁶)—C(R⁶)(R⁶)—Y—, or
(f) —C(R⁴)=C(R⁵)—C(R⁴)=C(R⁵)—;
s is 1 or 2;
Y is —O— and —S—;
R⁴ and R⁵ are independently:

(a) H,
(b) (C₁-C₆)-alkyl,
(c) (C₃-C₇)-cycloalkyl,
(d) F, Cl, Br, I,
(e) —NR⁷COOR¹¹,
(f) —SO₂NR⁷R¹¹,
(g) —O—(C₁-C₄)-alkyl,
(h) —S(O)$_n$—(C₁-C₄)-alkyl, or
(i) —NHSO₂R¹¹;
R⁶ is:
(a) H,
(b) (C₁-C₄)-alkyl, or
(c) F;
R⁷ is:
(a) H,
(b) (C₁-C₆)-alkyl,
(c) phenyl, or
(d) benzyl;
R⁸ is:
(a) H,
(b) (C₁-C₆)-alkyl, or
(c) phenyl;
R⁹ and R¹⁰ are independently:
(a) H,
(b) (C₁-C₆)-alkyl, unsubstituted or substituted with (C₃-C₇)-cycloalkyl,
(c) Cl, Br, F, I,
(d) (C₁-C₆)-alkoxy, or
(e) hydroxy-(C₁-C₆)-alkyl;
R¹¹ is:
(a) (C₁-C₆)-alkyl,
(b) phenyl,
(c) —(C₁-C₄)-alkyl-phenyl, or
(d) (C₃-C₇)-cycloalkyl;
R¹² is:
(a) H,
(b) (C₁-C₆)-alkyl, unsubstituted or substituted with one or two substituents selected from the group consisting of:
  (i) —OH,
  (ii) —O—(C₁-C₄)-alkyl,
  (iii) —O—(C₁-C₄)-cycloalkyl,
  (iv) —S(O)$_n$—(C₁-C₄)-alkyl,
  (v) —NR⁷—(C₁-C₄)-alkyl,
  (vi) —NR⁷R¹¹,
  (vii) —COOR⁷,
  (viii) —CONHR⁷,
  (ix) —OCOR¹¹,
  (x) —CONR⁷R¹¹,
  (xi) —NR⁷CONR⁷R¹¹,
  (xii) —NR⁷COOR¹¹,
  (xiii) —C(R⁶)(OH)—C(R⁶)(R⁷)(OH), or
  (xiv) —SO₂NR⁷R¹¹,
(c) (C₃-C₇)-cycloalkyl,
(d) (C₁-C₄)-perfluoroalkyl,
(e) aryl, unsubstituted or substituted with one to three substituents selected from the group consisting of:
  (i) F, Cl, Br, I,
  (ii) (C₁-C₆)-alkyl,
  (iii) (C₁-C₆)-alkoxy,
  (iv) hydroxy—(C₁-C₆)-alkyl,
  (v) —CF₃,
  (vi) —COOR⁷,
  (vii) —OH,
  (viii) —NR⁷R¹¹,
  (ix) —NH₂,
  (x) —NO₂, (xi) —CONR$^7$R$^{11}$,
(xii) two adjacent groups may be joined together to form a methylenedioxy group,
(f) aryl-(C$_1$-C$_2$)-alkyl unsubstituted or substituted with one to three substituents selected from the group consisting of:
  (i) F, Cl, Br, I,
  (ii) (C$_1$-C$_6$)-alkyl,
  (iii) (C$_1$-C$_6$)-alkoxy,
  (iv) hydroxy-(C$_1$-C$_6$)-alkyl,
  (v) —CF$_3$,
  (vi) —COOR$^7$,
  (vii) —OH,
  (viii) —NR$^7$R$^{11}$,
  (ix) —NH$_2$,
  (x) —NO$^2$,
  (xi) —CONR$^7$R$^{11}$, or
  (xii) two adjacent groups may be joined together to form a methylenedioxy group;

X is:
  (a) —O—,
  (b) —NR$^7$—,
  (c) —single bond, or
  (d) —C(R$^9$)$_2$—;

Z is:
  (a) —CO$_2$H,
  (b) —CO$_2$R$^{13}$,
  (c) —CONHSO$_2$-phenyl, wherein phenyl is unsubstituted or substituted with one or two substituents selected from the group consisting of:
    i) (C$_1$-C$_4$)-alkyl,
    ii) —O—(C$_1$-C$_4$)-alkyl,
    iii) —CONR$^7$R$^{11}$,
    iv) F, Cl, Br or I,
    v) —COOR$^7$,
    vi) (C$_1$-C$_4$)-perfluoroalkyl,
    vii) (C$_3$-C$_7$)-cycloalkyl,
    viii) NR$^7$R$^{11}$,
    ix) SO$_2$NR$^7$R$^{11}$,
    x) hydroxy, or
    xi) 2,3-, or 3,4-methylenedioxy;
  (d) —CONHSO$_2$—(C$_1$-C$_8$)-alkyl, wherein alkyl is unsubstituted or substituted as defined in R$^4$(b),
  (e) —CONHSO$_2$—(C$_3$-C$_7$)-cycloalkyl, or R$^{13}$ is:
  (a) (C$_1$-C$_4$)-alkyl,
  (b) CHR$^{14}$—O—COR$^{15}$,
  (c) CH$_2$CH$_2$—N[(C$_1$-C$_2$)-alkyl]$_2$,
  (d) (CH$_2$CH$_2$O)$_y$—O—[(C$_1$-C$_4$)-alkyl], wherein y is 1 or 2,
  (e) phenyl, naphthyl, CH$_2$-phenyl or CH$_2$-naphthyl, where phenyl or naphthyl is substituted or unsubstituted with CO$_2$—(C$_1$-C$_4$)-alkyl,

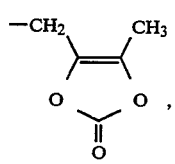
(f)

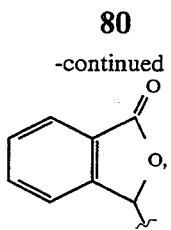
(g)

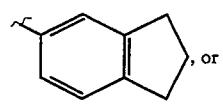
(h)

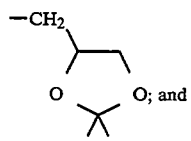
(i)

R$^{14}$ and R$^{15}$ independently are (C$_1$-C$_6$)-alkyl or phenyl,

R$^{16}$, R$^{17}$ and R$^{18}$ are independently:
  (a) H,
  (b) (C$_1$-C$_6$)-alkyl,
  (c) F, Cl, Br, I,
  (d) (C$_1$-C$_4$)-alkoxy,
  (e) —COOR$^7$,
  (f) —CONR$^7$R$^{11}$,
  (g) —CONHSO$_2$—(C$_1$-C$_6$)-alkyl wherein the alkyl group is unsubstituted or substituted as defined in R$^4$(b),
  (h) —CONHSO$_2$-phenyl wherein the phenyl group is unsubstituted or substituted as defined in Z(d).

4. The compound as recited in claim 1 of structural Formula IV:

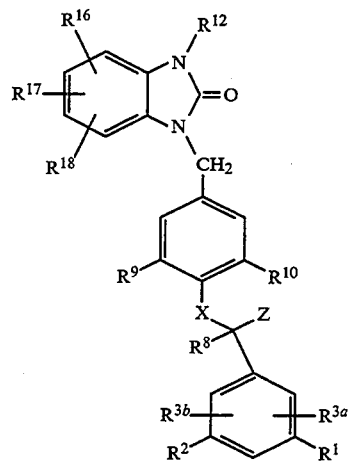

IV or a pharmaceutically acceptable salt thereof, wherein:
R$^1$, R$^2$, R$^{3a}$ and R$^{3b}$ are independently:
  (a) H,
  (b) F, Cl, Br, or I,
  (c) —NO$_2$,
  (d) (C$_1$-C$_4$)-alkyl,
  (e) —OR$^7$,
  (f) —NHCO—(C$_1$-C$_4$)-alkyl,
  (g) —NHCO—O(C$_1$-C$_4$)-alkyl,
  (h) —O—(CH$_2$)$_m$—OR$^7$,
  (i) —CONR$^7$R$^{11}$, or
  (j) —COOR$^7$;

m is 2, 3 or 4,
n is 0, 1 or 2,
$R^7$ is:
- (a) H,
- (b) $(C_1-C_6)$-alkyl,
- (c) phenyl, or
- (d) benzyl;

$R^8$ is:
- (a) H,
- (b) $(C_1-C_6)$-alkyl, or
- (c) phenyl;

$R^9$ and $R^{10}$ are independently:
- (a) H,
- (b) $(C_1-C_6)$-alkyl, unsubstituted or substituted with $(C_3-C_7)$-cycloalkyl,
- (c) Cl, Br, F, I,
- (d) $(C_1-C_6)$-alkoxy, or
- (e) hydroxy-$(C_1-C_6)$-alkyl;

$R^{11}$ is:
- (a) $(C_1-C_6)$-alkyl,
- (b) phenyl,
- (c) —$(C_1-C_4)$-alkyl-phenyl, or
- (d) $(C_3-C_7)$-cycloalkyl;

$R^{12}$ is:
- (a) H,
- (b) $(C_1-C_6)$-alkyl, unsubstituted or substituted with one or two substituents selected from the group consisting of:
  - (i) —OH,
  - (ii) —O—$(C_1-C_4)$-alkyl,
  - (iii) —O—$(C_1-C_4)$-cycloalkyl,
  - (iv) —S(O)$_n$—$(C_1-C_4)$-alkyl,
  - (v) —$NR^7$—$(C_1-C_4)$-alkyl,
  - (vi) —$NR^7R^{11}$,
  - (vii) —$COOR^7$,
  - (viii) —$CONHR^7$,
  - (ix) —$OCOR^{11}$,
  - (x) —$CONR^7R^{11}$,
  - (xi) —$NR^7CONR^7R^{11}$,
  - (xii) —$NR^7COOR^{11}$,
  - (xiii) —$C(R^6)(OH)$—$C(R^6)(R^7)(OH)$, or
  - (xiv) —$SO_2NR^7R^{11}$,
- (c) $(C_3-C_7)$-cycloalkyl,
- (d) $(C_1-C_4)$-perfluoroalkyl,
- (e) aryl, unsubstituted or substituted with one to three substituents selected from the group consisting of:
  - (i) F, Cl, Br, I,
  - (ii) $(C_1-C_6)$-alkyl,
  - (iii) $(C_1-C_6)$-alkoxy,
  - (iv) hydroxy-$(C_1-C_6)$-alkyl,
  - (v) —$CF_3$,
  - (vi) —$COOR^7$,
  - (vii) —OH,
  - (viii) —$NR^7R^{11}$,
  - (ix) —$NH_2$,
  - (x) —$NO_2$,
  - (xi) —$CONR^7R^{11}$,
  - (xii) two adjacent groups may be joined together to form a methylenedioxy group,
- (f) aryl—$(C_1-C_2)$-alkyl unsubstituted or substituted with one to three substituents selected from the group consisting of:
  - (i) F, Cl, Br, I,
  - (ii) $(C_1-C_6)$-alkyl,
  - (iii) $(C_1-C_6)$-alkoxy,
  - (iv) hydroxy-$(C_1-C_6)$-alkyl,
  - (v) —$CF_3$,
  - (vi) —$COOR^7$,
  - (vii) —OH,
  - (viii) —$NR^7R^{11}$,
  - (ix) —$NH_2$,
  - (x) —$NO_2$,
  - (xi) —$CONR^7R^{11}$, or
  - (xii) two adjacent groups may be joined together to form a methylenedioxy group;

X is:
- (a) —O—,
- (b) —$NR^7$—, or
- (c) —single bond;
- (d) —$C(R^9)_2$—,

Z is:
- (a) —$CO_2H$,
- (b) —$CO_2R^{13}$,
- (c) —$CONHSO_2$-phenyl, wherein phenyl is unsubstituted or substituted with one or two substituents selected from the group consisting of:
  - i) $(C_1-C_4)$-alkyl,
  - ii) —O—$(C_1-C_4)$-alkyl,
  - iii) —$CONR^7R^{11}$,
  - iv) F, Cl, Br or I,
  - v) —$COOR^7$,
  - vi) $(C_1-C_4)$-perfluoroalkyl,
  - vii) $(C_3-C_7)$-cycloalkyl,
  - viii) $NR^7R^{11}$,
  - ix) $SO_2NR^7R^{11}$,
  - x) hydroxy, or
  - xi) 2,3-, or 3,4-methylenedioxy;
- (d) —$CONHSO_2$—$(C_1-C_8)$-alkyl, wherein alkyl is unsubstituted or substituted as defined in $R^4$(b),
- (e) —$CONHSO_2$—$(C_3-C_7)$-cycloalkyl, $R^{13}$ is:
- (a) $(C_1-C_4)$-alkyl,
- (b) $CHR^{14}$—O—$COR^{15}$,
- (c) $CH_2CH_2$—$N[(C_1-C_2)$-alkyl]$_2$,
- (d) $(CH_2CH_2O)_y$—O—$[(C_1-C_4)$-alkyl], wherein y is 1 or 2,
- (e) phenyl, naphthyl, $CH_2$-phenyl or $CH_2$-naphthyl, where phenyl or naphthyl is substituted or unsubstituted with $CO_2$-$(C_1-C_4)$-alkyl,

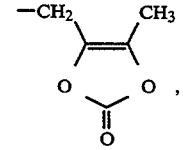  (f)

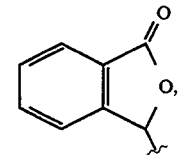  (g)

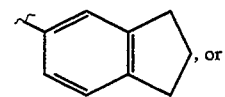  (h)
, or

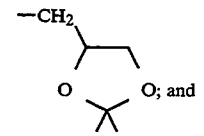  (i)
; and $R^{14}$, and $R^{15}$ independently are $(C_1-C_6)$-alkyl or phenyl, $R^{16}$, $R^{17}$ and $R^{18}$ are independently:
(a) H,
(b) $(C_1-C_6)$-alkyl,
(c) F, Cl, Br, I,
(d) $(C_1-C_4)$-alkoxy,
(e) —COOR$^7$,
(f) —CONR$^7$R$^{11}$,
(g) —CONHSO$_2$—$(C_1-C_6)$-alkyl wherein the alkyl group is unsubstituted or substituted as defined in R$^4$(b),
(h) —CONHSO$_2$-phenyl wherein the phenyl group is unsubstituted or substituted as defined in Z(d).

5. The compound as recited in claim 1 of structural Formula V:

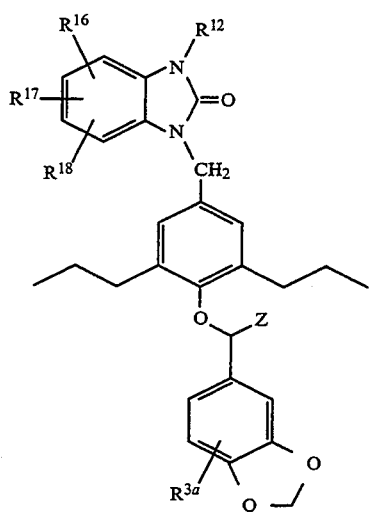

wherein $R^3a$, $R^{12}$, $R^{16}$, $R^{17}$, $R^{18}$ and Z are either hydrogen or as defined in the table below:

| $R^{3a}$ | $R^{12}$ | $R^{16}, R^{17}, R^{18}$ | Z |
|---|---|---|---|
| H | H | | COOH |
| H | Me | | COOH |
| H | Et | | COOH |
| H | nPr | | COOH |
| H | ipr | | COOH |
| H | nBu | | COOH |
| H | iBu | | COOH |
| H | tBu | | COOH |
| H | Ph | | COOH |
| H | H | 4-Me | COOH |
| H | H | 5-Me | COOH |
| H | H | 6-Me | COOH |
| H | H | 5,6-diMe | COOH |
| H | Me | 5-Me | COOH |
| H | Me | 6-Me | COOH |
| H | CH$_2$COOH | | COOH |
| H | CH$_2$COOH | 5-Me | COOH |
| H | CH$_2$COOH | 6-Me | COOH |
| H | H | | CONHSO$_2$(iPr) |
| H | H | | CONHSO$_2$Ph(4-iPr) |
| H | Me | | CONHSO$_2$Ph(4-tBu) |
| H | Me | | CONHSO$_2$(iPr) |
| H | Me | | CONHSO$_2$Ph(4-iPr) |
| H | Me | | CONHSO$_2$Ph(4-tBu) |
| 5-OMe | H | | COOH |
| 5-OMe | Me | | COOH |
| 5-OMe | Et | | COOH |
| 5-OMe | nPr | | COOH |
| 5-OMe | iPr | | COOH |
| 5-OMe | nBu | | COOH |
| 5-OMe | iBu | | COOH |
| 5-OMe | Ph | | COOH |
| 5-OMe | H | 5-Me | COOH |
| 5-OMe | H | 6-Me | COOH |
| 5-OMe | Me | 5-Me | COOH |
| 5-OMe | Me | 6-Me | COOH |
| 5-Br | Me | | COOH |
| 5-Br | Et | | COOH |
| 5-Br | nPr | | COOH |
| 5-Br | ipr | | COOH |
| 5-Br | nBu | | COOH |
| 5-Br | iBu | | COOH |
| 5-Br | Ph | | COOH |
| 5-Br | H | 5-Me | COOH |
| 5-Br | H | 6-Me | COOH |
| 5-Br | Me | 5-Me | COOH |
| 5-Br | Me | 6-Me | COOH. |

6. The compound as recited in claim 1 of structural formula VI:

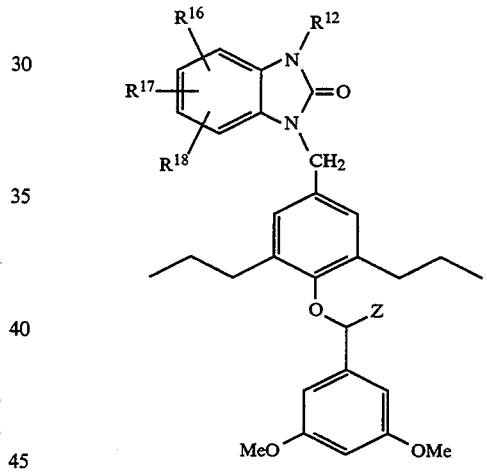

wherein $R^{12}$, $R^{16}$, $R^{17}$, $R^{18}$ and Z are either hydrogen or as defined in the table below:

| $R^{12}$ | $R^{16}, R^{17}, R^{18}$ | Z |
|---|---|---|
| H | | COOH |
| Me | | COOH |
| Et | | COOH |
| nPr | | COOH |
| iPr | | COOH |
| nBu | | COOH |
| iBu | | COOH |
| Ph | | COOH |
| H | 5-Me | COOH |
| H | 6-Me | COOH |
| Me | 5-Me | COOH |
| Me | 6-Me | COOH. |

7. The compound as recited in claim 1 of structural formula VII:

VII

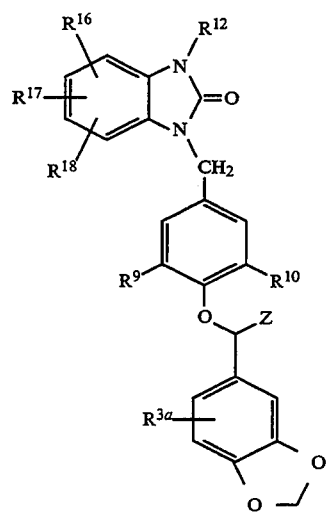

wherein $R^{3a}$, $R^9$, $R^{10}$, $R^{12}$, $R^{16}$, $R^{17}$, $R^{18}$ and Z are either hydrogen or as defined in the table below:

| $R^{3a}$ | $R^9$ | $R^{10}$ | $R^{12}$ | $R^{16}$, $R^{17}$, $R^{18}$ | Z |
|---|---|---|---|---|---|
| H | nPr | H | H | | COOH |
| H | nPr | H | Me | | COOH |
| H | nPr | H | Et | | COOH |
| H | nPr | H | H | 5-Me | COOH |
| H | nPr | H | H | 6-Me | COOH |
| H | nPr | H | Me | 5-Me | COOH |
| H | nPr | H | Me | 6-Me | COOH |
| H | nPr | H | H | | CONHSO$_2$(iPR) |
| H | nPr | H | Me | | CONHSO$_2$(iPR) |
| H | nPr | H | Et | | CONHSO$_2$(iPR) |
| H | nPr | H | H | 5-Me | CONHSO$_2$(iPR) |
| H | nPr | H | H | 6-Me | CONHSO$_2$(iPr) |
| H | nPr | H | Me | 5-Me | CONHSO$_2$(iPr) |
| H | nPr | H | Me | 6-Me | CONHSO$_2$(iPr) |
| H | nPr | H | H | | CONHSO$_2$Ph(4-iPr) |
| H | nPr | H | Me | | CONHSO$_2$Ph(4-iPr) |
| H | nPr | H | Et | | CONHSO$_2$Ph(4-iPr) |
| H | nPr | H | H | 5-Me | CONHSO$_2$Ph(4-iPr) |
| H | nPr | H | H | 6-Me | CONHSO$_2$Ph(4-iPr) |
| H | nPr | H | Me | 5-Me | CONHSO$_2$Ph(4-ipr) |
| H | nPr | H | Me | 6-Me | CONHSO$_2$Ph(4-iPr) |
| 5-OMe | nPr | H | H | | CONHSO$_2$(iPr) |
| 5-OMe | nPr | H | H | | CONHSO$_2$Ph(4-iPr) |
| 5-OMe | nPr | H | Et | | CONHSO$_2$(iPr) |
| 5-OMe | nPr | H | Et | | CONHSO$_2$Ph(4-iPr) |
| H | Et | H | H | H | COOH |
| H | Et | H | Et | H | COOH |
| H | Et | H | H | H | CONHSO$_2$(iPr) |
| H | Et | H | H | H | CONHSO$_2$Ph(4-iPr) |
| H | Et | H | Et | H | CONHSO$_2$(iPr) |
| H | Et | H | Et | H | CONHSO$_2$Ph(4-iPr) |
| H | nPr | Cl | H | | COOH |
| H | nPr | Cl | Me | | COOH |
| H | nPr | Cl | Et | | COOH |
| H | nPr | Cl | H | 5-Me | COOH |
| H | nPr | Cl | H | 6-Me | COOH |
| H | nPr | Cl | Me | 5-Me | COOH |
| H | nPr | Cl | Me | 6-Me | COOH |
| H | Cl | Cl | H | | COOH |
| H | Cl | Cl | Et | | COOH |
| H | Cl | Cl | Me | 6-Me | COOH |
| H | H | H | H | | COOH |
| H | H | H | Et | | COOH |
| H | H | H | H | | CONHSO$_2$(iPr) |
| H | H | H | Et | | CONHSO$_2$(iPr) |
| H | H | H | H | | CONHSO$_2$Ph(4-iPr) |
| H | H | H | Et | | CONHSO$_2$Ph(4-iPr) |
| H | OMe | OMe | H | | COOH |
| H | OMe | OMe | Et | | COOH. |

8. The compound as recited in claim 1 of structural formula VIII:

VIII

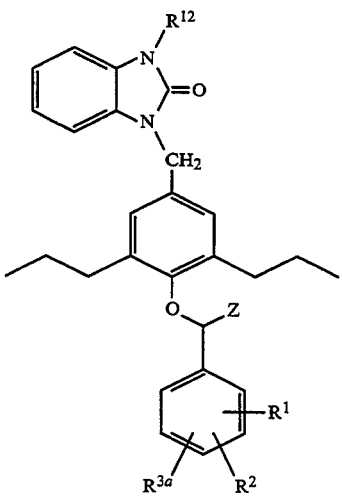

wherein $R^1$, $R^2$, $R^3a$, $R^{12}$ and Z are either hydrogen or as defined in the table below:

| $R^1$, $R^2$, $R^{3a}$ | $R^{12}$ | Z |
|---|---|---|
| 3-Me | H | COOH |
| 3-Me | Et | COOH |
| 3-Cl | H | COOH |
| 3-Cl | Et | COOH |
| 3-OMe | H | COOH |
| 3-OMe | Et | COOH |
| 3,5-diSMe | H | COOH |
| 3,5-diSMe | Et | COOH |
| 1'-Me-3,4-methylenedioxy | H | COOH |
| 1'-Me-3,4-methylenedioxy | Et | COOH. |

9. A method of treating a condition in a mammal, the treatment of which is effected or facilitated by a decrease in endothelin mediated actions, comprising the administration, in an amount that is effective for antagonizing the effect of endothelin, of a compound of Structural Formula I as recited in claim 1.

10. The method as recited in claim 9, wherein the condition is selected from the group consisting of: hypertension, pulmonary hypertension, Raynaud's disease, myocardial infarction, angina pectoris, congestive heart failure, acute renal failure, cerebral infarction, cerebral vasospasm, arteriosclerosis, vascular restenosis, asthma, inflammatory bowel diseases, endotoxic shock, endotoxininduced multiple organ failure or disseminated intravascular coagulation, or cyclosporin-induced renal failure or hypertension.

11. The method as recited in claim 10, wherein the condition is hypertension.

12. The method as recited in claim 11, wherein the mammal is human.

13. A method of treating cardiovascular disorders by administering to a person in need of such treatment a therapeutically effective amount of a compound of Formula I as recited in claim 1.

14. A pharmaceutical formulation for treatment of a condition in a mammal, the treatment of which is effected or facilitated by a decrease in endothelin mediated actions, comprising, in an amount that is effective for antagonizing the effect of endothelin, the compound of formula I as recited in claim 1 and a pharmaceutically acceptable carrier.

15. A pharmaceutical formulation for the treatment of hypertension comprising a pharmaceutically acceptable carrier and an effective amount of the compound of claim 1.

16. A pharmaceutical formulation for the treatment of pulmonary hypertension comprising a pharmaceutically acceptable carrier and an effective amount of the compound of claim 1.

17. A pharmaceutical formulation for the treatment of asthma comprising a pharmaceutically acceptable carrier and an effective amount of the compound of claim 1.

* * * * *

UNITED STATES PATENT AND TRADEMARK OFFICE
CERTIFICATE OF CORRECTION

PATENT NO. : 5,391,566
DATED : February 21, 1995
INVENTOR(S) : Prasun K. Chakravarty, Elizabeth M. Naylor
James R. Tata and Thomas F. Walsh It is certified that error appears in the above-indentified patent and that said Letters Patent is hereby corrected as shown below:

At Column 70, in Claim 1, beginning at line 36, (xi) should read as follows:

(xi) $-CONR^7R^{11}$ or

At Column 70, in Claim 1, beginning at line 41, (a) should read as follows:

(a) -O-,

At Column 73, in Claim 2, beginning at line 39, (f) should read as follows:

(f) $-COOR^7$,

At Column 74, in Claim 2, beginning at line 19, (g) should read as follows:

(g) When $R^9$ and $R^{10}$ are on adjacent carbons, they can be joined to form a phenyl ring, Signed and Sealed this Thirteenth Day of June, 1995

*Attest:*

BRUCE LEHMAN

*Attesting Officer*          *Commissioner of Patents and Trademarks*